United States Patent [19]
Cheever et al.

[11] Patent Number: 5,876,712
[45] Date of Patent: Mar. 2, 1999

[54] IMMUNE REACTIVITY TO HER-2/NEU PROTEIN FOR DIAGNOSIS AND TREATMENT OF MALIGNANCIES IN WHICH THE HER-2/NEU ONCOGENE IS ASSOCIATED

[75] Inventors: Martin A. Cheever, Mercer Island; Mary L. Disis, Renton, both of Wash.

[73] Assignee: University of Washington, Seattle, Wash.

[21] Appl. No.: 468,545

[22] Filed: Jun. 6, 1995

Related U.S. Application Data

[63] Continuation of Ser. No. 414,417, Mar. 31, 1995, which is a continuation-in-part of Ser. No. 106,112, Aug. 12, 1993, abandoned, which is a continuation-in-part of Ser. No. 33,644, Mar. 17, 1993, abandoned.

[51] Int. Cl.$^6$ .............................. A61K 35/14; C12N 5/08
[52] U.S. Cl. .................... 424/93.7; 424/93.1; 424/93.71; 424/534; 435/325; 435/372; 435/372.3
[58] Field of Search .............................. 424/93.71, 93.1, 424/97.7, 534; 435/7.1, 325, 372, 372.3; 530/350

[56] References Cited

U.S. PATENT DOCUMENTS

| | | | |
|---|---|---|---|
| 3,766,162 | 10/1973 | Spector | 260/112 R |
| 3,791,932 | 2/1974 | Schuurs et al. | 195/103.5 R |
| 3,817,837 | 6/1974 | Rubenstein et al. | 195/103.5 R |
| 3,850,752 | 11/1974 | Schuurs et al. | 195/103.5 R |
| 3,901,654 | 8/1975 | Gross | 23/230 B |
| 3,935,074 | 1/1976 | Rubenstein et al. | 195/103.5 R |
| 3,984,533 | 10/1976 | Uzgiris | 424/12 |
| 3,996,345 | 12/1976 | Ullman et al. | 424/12 |
| 4,034,074 | 7/1977 | Miles | 424/1 |
| 4,098,876 | 7/1978 | Piasio et al. | 424/1 |
| 4,233,402 | 11/1980 | Maggio et al. | 435/7 |
| 4,452,901 | 6/1984 | Gordon et al. | 436/506 |
| 5,320,947 | 6/1994 | Cheever et al. | 435/29 |

FOREIGN PATENT DOCUMENTS

WO 91/02062   2/1991   WIPO .

OTHER PUBLICATIONS

Lichtenstein, Cellular Immunology 141: 219–232 Apr. 15 1992.
Ioannides, FASEB J. V.6: A1404, Feb. 26, 1992.
Kedar & Klein, Adv. in Cancer Res 59: 245 1992.
Strome et al, J. Hematotherapy 2:63–73, 1993.
Dermer, Bio/Technology 12: 320 Mar. 12, 1994.
Lotze, Cell Transplantation 2:33–47, 1993.
Whiteside, Cancer Immunol Immunother 39:15,1994.
Alper et al., "The Presence of c–erbB–2 Gene Product–related Protein in Culture Medium Conditioned by Breast Cancer Cell Line SK–BR–3," *Cell Growth & Differentiation* 1:591–599, 1990.
Bargmann et al., "The neu oncogene encodes an epidermal growth factor receptor–related protein," *Nature* 319: 226–230, 1986.

Bishop and Orosz, "Limiting Dilution Analysis For Alloreactive, TCGF–Secretory T Cells. Two Related LDA Methods That Discriminate Between Unstimulated Precursor T Cells and In Vivo–Alloactivated T Cells," *Transplantation* 47(4): 671–677, 1989.
Bowen–Pope et al., "Production of platelet–derived growth factor–like molecules and reduced expression of platelet–derived growth factor receptors accompany transformation by a wide spectrum of agents," *Proc. Natl. Acad. Sci. USA* 81:2396–2400, 1984.
Brooks et al., "Human lymphocyte markers defined by antibodies derived from somatic cell hybrids," *Clin. exp. Immunol.* 39: 477–485, 1980.
Brown et al., "Protein Antigens of Normal and Malignant Human Cells Identified by Immunoprecipitation with Monoclonal Antibodies," *Journal of Biological Chemistry* 255(11): 4980–4983, 1980.
Burnette et al., "Western Blotting: Electrophoretic Transfer of Proteins from Sodium Dodecyl Sulfate–Palyacrylamide Gels to Unmodified Nitrocellulose and Radiographic Detection with Antibody and Radioiodinated Protein A," *Analytical Biochemistry* 112: 195–203, 1981.
Dhut et al, "BCR–ABL and BCR Proteins: Biochemical Characterization and Localization," *Leukemia* 4(11): 745–750, 1990.
Falk et al., "Allele–specific motifs revealed by sequencing of self–peptides eluted from MHC molecules," *Nature* 351: 290–296, 1991.
Feller and de la Cruz, "Identifying antigenic T–cell sites," *Nature* 349: 720–721, 1991.
Iglehart et al., "Increased erbB–2 Gene Copies and Expression in Multiple Stages of Breast Cancer," *Cancer Research* 50: 6701–6707, 1990.
Ioannides et al., "T–Cell Recognition of Oncogene Products: A New Strategy for Immunotherapy," *Molecular Carcinogenesis* 6: 77–82, 1992.
Kallioniemi et al., "ERBB2 amplification in breast cancer analyzed by fluorescence in situ hybridization," *Proc. Natl. Acad. Sci.* 89: 5321–5325, 1992.
Kerns et al., "c–erbB–2 Expression In Breast Cancer Detected by Immunoblotting and Immunohistochemistry," *Journal of Histochemistry and Cytochemistry* 38(12): 1823–1830, 1990.

(List continued on next page.)

Primary Examiner—Toni R. Scheiner
Assistant Examiner—Nancy A. Johnson
Attorney, Agent, or Firm—Seed and Berry LLP

[57] ABSTRACT

Methods for the detection, monitoring and treatment of malignancies in which the HER-2/neu oncogene is associated are disclosed. Detection of specific T cell activation (e.g., by measuring the proliferation of T cells) in response to in vitro exposure to the HER-2/neu protein, or detection of immunocomplexes formed between the HER-2/neu protein and antibodies in body fluid, allows the diagnosis of the presence of a malignancy in which the HER-2/neu oncogene is associated. The present invention also discloses methods and compositions, including peptides, for treating such malignancies.

7 Claims, 21 Drawing Sheets

OTHER PUBLICATIONS

Laemmli, U., "Cleavage of Structural Proteins during the Assembly of the Head of Bacteriophage T4," *Nature* 227: 680–685, 1970.

Leitzel et al., "Elevated Soluble c–erbB2 Antigen Levels in the Serum and Effusions of a Proportion of Breast Cancer Patients," *Journal of Clinical Oncology* 10(9): 1436–1443, 1992.

Lippman, M., "Potential Contributions of Breast Cancer Biology to Management of Breast Cancer," *Advances in Oncology* 8(3): 26–28, 1992.

Maguire and Greene, "The neu (c–erbB–2) Oncogene," *Seminars in Oncology* 16(2): 148–155, 1989.

Margalit et al., "Prediction Of Immunodominant Helper T. Cell Antigenic Sites From The Primary Sequence," *Journal of Immunology* 138(7): 2213–2229, 1987.

McKenzie et al., "Induction of Antitumor Immunity by Immunization with a Vaccinia Virus Vector Expressing and Oncogene–encoded Product," in *Vaccines* 88, Cold Spring Harbor Laboratory, 1988, pp. 19–23.

Mietzner et al., "Purification and Characterization of the Major Iron–Regulated Protein Expressed By Pathogenic Neisseriae," *Journal of Experimental Medicine* 165: 1041–1057, 1987.

Mori et al., "In vitro and in vivo Release of Soluble erbB–2 Protein from Human Carcinoma Cells," *Japanese Journal of Cancer Research* 81: 489–494, 1990.

Paik et al., "Pathologic Findings From the National Surgical Adjuvant Breast and Bowel Project: Prognostic Significance of erbB–2 Protein Overexpression in Primary Breast Cancer," *Journal of Clinical Oncology* 8(1): 103–112, 1990.

Parker et al., "Sequence Motifs Important For Peptide Binding To The Human MHC Class I Molecule, HLA–A2," *Journal of Immunology* 149(11):3580–3587, 1992.

Press et al., "Expression of the HER–2/neu proto–oncogene in normal human adult and fetal tissues," *Oncogene* 5: 953–962, 1990.

Raines and Ross, "Platelet–derived Growth Factor. I. High Yields Purification and Evidence for Multiple Forms," *Journal of Biological Chemistry* 257(9): 5154–5159, 1982.

Riberdy and Cresswell, "The Antigen–Processing Mutant T2 Suggests a Role for MHC–Linked Genes in Class II Antigen Presentation," *Journal of Immunology* 148(8): 2586–2590, 1992.

Rothbard and Taylor, "A sequence pattern common to T cell epitopes," *EMBO Journal* 7(1) 93–100, 1988.

Spies et al., "A gene in the human major histocompatibility complex class II region controlling the class I antigen presentation pathway," *Nature* 348: 744–747, 1990.

Stern et al., "Oncogenic Activation of p185$^{neu}$ Stimulates Tyrosine Phosphorylation In Vivo," *Molecular and Cellular Biology* 8(9): 3969–3973, 1988.

Trowsdale et al., "Sequence encoded in the class II region of the MHC related to the 'ABC' superfamily of transporters," *Nature* 348: 741–744, 1990.

Wide, L., "Solid Phase Antigen–Antibody Systems," in *Radioimmunoassay Methods,* Kirkham and Hunter (eds.), 1973, pp. 405–412.

Zabrecky et al., "The Extracellular Domain of p185/neu Is Released from the Surface of Human Breast Carcinoma Cells, SK–BR–3," *Journal of Biological Chemistry* 266(3): 1716–1720, 1991.

Ioannides, C.G., et al., "Antigens Recognized by T Cells in Ovarian Cancer," Abstracts of the Fourth International Conference of Anticancer Research, 1992, p. 1870.

Ioannides, C.G., "Antigens and Vaccines of Female Genital Cancers," Society for Biological Therapy 1992 Annual Meeting, 1992, p. 27.

Ioannides, C.G., et al., "Cytotoxic T Cells Isolated From Ovarian Malignant Ascites Recognize a Peptide Derived From the HER–2/neu Proto–oncogene," *Cell. Immunol.* 151:225–234, 1993.

Disis, M.L., et al., "Existent T–Cell and Antibody Immunity to HER–2/neu Protein in Patients With Breast Cancer," *Cancer Res.* 54:16–20, 1994.

```
        5     10    15    20    25    30    35    40    45    50    55    60    65    70    75
MELAALCRWGLLLALLPPGAASTQVCTGTDMKLRLPASPETHLDMLRHLYQGCQVVQGNLELTYLPTNASLSFLQ 80    85    90    95   100   105   110   115   120   125   130   135   140   145   150
DIQEVQGYVLIAHNQVRQVPLQRLRIVRGTQLFEDNYALAVLDNGDPLNNTTPVTGASPGGLRELQLRSLTEILK 155   160   165   170   175   180   185   190   195   200   205   210   215   220   225
GGVLIQRNPQLCYQDTILWKDIFHKNNQLALTLIDTNRSRACHPCSPMCKGSRCWGESSEDCQSLTRTVCAGGCA 230   235   240   245   250   255   260   265   270   275   280   285   290   295   300
RCKGPLPTDCCHEQCAAGCTGPKHSDCLACLHFNHSGICELHCPALVTYNTDTFESMPNPEGRYTFGASCVTACP 305   310   315   320   325   330   335   340   345   350   355   360   365   370   375
YNYLSTDVGSCTLVCPLHNQEVTAEDGTQRCEKCSKPCARVCYGLGMEHLREVRAVTSANIQEFAGCKKIFGSLA 380   385   390   395   400   405   410   415   420   425   430   435   440   445   450
FLPESFDGDPASNTAPLQPEQLQVFETLEEITGYLYISAWPDSLPDLSVFQNLQVIRGRILHNGAYSLTLQGLGI 455   460   465   470   475   480   485   490   495   500   505   510   515   520   525
SWLGLRSLRELGSGLALIHHNTHLCFVHTVPWDQLFRNPHQALLHTANRPEDECVGEGLACHQLCARCHCWGPGP 530   535   540   545   550   555   560   565   570   575   580   585   590   595   600
TQCVNCSQFLRGQECVEECRVLQGLPREYVNARHCLPCHPECQPQNGSVTCFGPEADQCVACAHYKDPPFCVARC 605   610   615   620   625   630   635   640   645   650   655   660   665   670   675
PSGVKPDLSYMPIWKFPDEEGACQPCPINCTHSCVDLDDKGCPAEQRASPLTSIISAVVGILLVVVLGVVFGILI 680   685   690   695   700   705   710   715   720   725   730   735   740   745   750
KRRQQKIRKYTMRRLLQETELVEPLTPSGAMPNQAQMRILKETELRKVKVLGSGAFGTVYKGIWIPDGENVKIPV 755   760   765   770   775   780   785   790   795   800   805   810   815   820   825
AIKVLRENTSPKANKEILDEAYVMAGVGSPYVSRLLGICLTSTVQLVTQLMPYGCLLDHVRENRGRLGSQDLLNW 830   835   840   845   850   855   860   865   870   875   880   885   890   895   900
CMQIAKGMSYLEDVRLVHRDLAARNVLVKSPNHVKITDFGLARLLDIDETEYHADGGKVPIKWMALESILRRRFT 905   910   915   920   925   930   935   940   945   950   955   960   965   970   975
HQSDVWSYGVTVWELMTFGAKPYDGIPAREIPDLLEKGERLPQPPICTIDVYMIMVKCWMIDSECRPRFRELVSE 980   985   990   995  1000  1005  1010  1015  1020  1025  1030  1035  1040  1045  1050
FSRMARDPQRFVVIQNEDLGPASPLDSTFYRSLLEDDDMGDLVDAEEYLVPQQGFFCPDPAPGAGGMVHHRHRSS 1055  1060  1065  1070  1075  1080  1085  1090  1095  1100  1105  1110  1115  1120  1125
STRSGGGDLTLGLEPSEEEAPRSPLAPSEGAGSDVFDGDLGMGAAKGLQSLPTHDPSPLQRYSEDPTVPLPSETD 1130  1135  1140  1145  1150  1155  1160  1165  1170  1175  1180  1185  1190  1195  1200
GYVAPLTCSPQPEYVNQPDVRPQPPSPREGPLPAARPAGATLERPKTLSPGKNGVVKDVFAFGGAVENPEYLTPQ 1205  1210  1215  1220  1225  1230  1235  1240  1245  1250  1255
GGAAPQPHPPPAFSPAFDNLYYWDQDPPERGAPPSTFKGTPTAENPEYLGLDVPV
```

*Fig. 1*

ECD PROTEIN
ICD PROTEIN p110 →

← p75

A  B

FIGURE 7

IMMUNE REACTIVITY TO HER-2/NEU PROTEIN FOR DIAGNOSIS AND TREATMENT OF MALIGNANCIES IN WHICH THE HER-2/NEU ONCOGENE IS ASSOCIATED

CROSS-REFERENCE TO RELATED APPLICATIONS

This application is a continuation of U.S. patent application Ser. No. 08/414,417, filed Mar. 31, 1995, pending; which application is a continuation-in-part application to Ser. No. 08/106,112, filed Aug. 12, 1993, abandoned; which application is a continuation-in-part application to Ser. No. 08/033,644, filed Mar. 17, 1993, abandoned.

TECHNICAL FIELD

The present invention is generally directed toward the detection, monitoring, and treatment of malignancies, in which the HER-2/neu oncogene is associated, through the use of a cancer patient's own immune reactivity to the HER-2/neu protein expressed by the HER-2/neu gene.

BACKGROUND OF THE INVENTION

Despite enormous investments of financial and human resources, cancer remains one of the major causes of death. For example, cancer is the leading cause of death in women between the ages of 35 and 74. Breast cancer is the most common malignancy in women and the incidence for developing breast cancer is on the rise. One in nine women will be diagnosed with the disease. Standard approaches to cure breast cancer have centered around a combination of surgery, radiation and chemotherapy. These approaches have resulted in some dramatic successes in certain malignancies. However, breast cancer is most often incurable, when diagnosed beyond a certain stage. Alternative approaches to early diagnosis and therapy are necessary.

A common characteristic of malignancies is uncontrolled cell growth. Cancer cells appear to have undergone a process of transformation from the normal phenotype to a malignant phenotype capable of autonomous growth. Amplification and overexpression of somatic cell genes is considered to be a common primary event that results in the transformation of normal cells to malignant cells. The malignant phenotypic characteristics encoded by the oncogenic genes are passed on during cell division to the progeny of the transformed cells.

Ongoing research involving oncogenes has identified at least forty oncogenes operative in malignant cells and responsible for, or associated with, transformation. Oncogenes have been classified into different groups based on the putative function or location of their gene products (such as the protein expressed by the oncogene).

Oncogenes are believed to be essential for certain aspects of normal cellular physiology. In this regard, the HER-2/neu oncogene is a member of the tyrosine protein kinase family of oncogenes and shares a high degree of homology with the epidermal growth factor receptor. HER-2/neu presumably plays a role in cell growth and/or differentiation. HER-2/neu appears to induce malignancies through quantitative mechanisms that result from increased or deregulated expression of an essentially normal gene product.

HER-2/neu (p185) is the protein product of the HER-2/neu oncogene. The HER-2/neu gene is amplified and the HER-2/neu protein is overexpressed in a variety of cancers including breast, ovarian, colon, lung and prostate cancer. HER-2/neu is related to malignant transformation. It is found in 50%–60% of ductal in situ carcinoma and 20%–40% of all breast cancers, as well as a substantial fraction of adenocarcinomas arising in the ovaries, prostate, colon and lung. HER-2/neu is intimately associated not only with the malignant phenotype, but also with the aggressiveness of the malignancy, being found in one-fourth of all invasive breast cancers. HER-2/neu overexpression is correlated with a poor prognosis in both breast and ovarian cancer. HER-2/neu is a transmembrane protein with a relative molecular mass of 185 kd that is approximately 1255 amino acids (aa) in length. It has an extracellular binding domain (ECD) of approximately 645 aa, with 40% homology to epidermal growth factor receptor (EGFR), a highly hydrophobic transmembrane anchor domain (TMD), and a carboxyterminal cytoplasmic domain (CD) of approximately 580 aa with 80% homology to EGFR.

An approach to developing a diagnostic assay for malignancies, in which the HER-2/neu oncogene is associated, has been to attempt to quantify the protein expression product of the HER-2/neu oncogene in tissue or body fluids. However, there have been problems in the development of diagnostic assays based on direct detection of HER-2/neu protein.

Due to the difficulties in the current approaches to diagnosis and therapy of cancers in which the HER-2/neu oncogene is associated, there is a need in the art for improved methods and compositions. The present invention fills this need, and further provides other related advantages.

SUMMARY OF THE INVENTION

Briefly stated, the present invention provides a variety of methods for the detection of a malignancy in a warm-blooded animal, wherein a HER-2/neu oncogene is associated with the malignancy. The methods may be used on a one time basis when a malignancy is suspected or on a periodic basis, e.g., to monitor an individual with an elevated risk of acquiring or reacquiring a malignancy. In one embodiment, the method comprises the steps of: (a) isolating $CD4^+$ T cells from a warm-blooded animal; (b) incubating the T cells with HER-2/neu protein; and (c) detecting the presence or absence of specific activation of the T cells, thereby determining the presence or absence of the malignancy. In another embodiment, the method comprises the steps of: (a) isolating $CD8^+$ T cells from a warm-blooded animal; (b) incubating the T cells with HER-2/neu protein; and (c) detecting the presence or absence of specific activation of the T cells, thereby determining the presence or absence of the malignancy. In another embodiment, the method comprises the steps of: (a) contacting a body fluid, suspected of containing antibodies specific for HER-2/neu protein, with HER-2/neu protein; (b) incubating the body fluid under conditions and for a time sufficient to allow immunocomplexes to form; and (c) detecting the presence or absence of immunocomplexes formed between the HER-2/neu protein and antibodies in the body fluid specific for the HER-2/neu protein, thereby determining the presence or absence of the malignancy.

In another aspect, the present invention provides methods for monitoring the effectiveness of cancer therapy in a warm-blooded animal with a malignancy, wherein a HER-2/neu oncogene is associated with the malignancy. Uses of such methods include the early detection of relapse. In one embodiment, the method comprises the steps of: (a) contacting a first body fluid sample, taken from the warm-blooded animal prior to initiation of therapy, with HER-2/ neu protein; (b) incubating the body fluid under conditions and for a time sufficient to allow immunocomplexes to form; (c) detecting immunocomplexes formed between the HER-2/neu protein and antibodies in the body fluid specific for the HER-2/neu protein; (d) repeating steps (a), (b), and (c) on a second body fluid sample taken from the animal subsequent to the initiation of therapy; and (e) comparing the number of immunocomplexes detected in the first and second body fluid samples, thereby monitoring the effectiveness of the therapy in the animal.

The present invention is also directed toward methods for treating a malignancy in a warm-blooded animal, wherein a HER-2/neu oncogene is associated with the malignancy. In one embodiment, the method comprises the steps of: (a) isolating CD4+ T cells from a warm-blooded animal; (b) incubating the T cells in the presence of HER-2/neu protein, such that the T cells proliferate; and (c) administering to the warm-blooded animal an effective amount of the proliferated T cells. In another embodiment, the method comprises the steps of: (a) isolating CD8+ T cells from a warm-blooded animal; (b) incubating the T cells in the presence of HER-2/neu protein, such that the T cells proliferate; and (c) administering to the warm-blooded animal an effective amount of the proliferated T cells. In another embodiment, the method comprises the steps of: (a) isolating CD4+ T cells from a warm-blooded animal; (b) incubating the T cells in the presence of HER-2/neu protein, such that the T cells proliferate; (c) cloning one or more cells that proliferated in the presence of HER-2/neu protein; and (d) administering to the warm-blooded animal an effective amount of the cloned T cells. In another embodiment, the method comprises the steps of: (a) isolating CD8+ T cells from a warm-blooded animal; (b) incubating the T cells in the presence of HER-2/neu protein, such that the T cells proliferate; (c) cloning one or more cells that proliferated in the presence of HER-2/neu protein; and (d) administering to the warm-blooded animal an effective amount of the cloned T cells. In yet another embodiment, the method comprises immunizing the animal with a HER-2/neu peptide recognized by T cells, the peptide not being the extracellular domain of the protein expression product of a HER-2/neu oncogene.

Within a related aspect, the present invention provides anti-cancer therapeutic compositions comprising T cells proliferated in the presence of HER-2/neu protein, in combination with a pharmaceutically acceptable carrier or diluent. In addition, a variety of peptides designated for CD8+ T cell responses are provided which include peptides consisting essentially of:

His-Leu-Tyr-Gln-Gly-Cys-Gln-Val-Val (Seq. ID No. 1);
Pro-Leu-Gln-Pro-Glu-Gln-Leu-Gln-Val (Seq. ID No. 2);
Pro-Leu-Thr-Ser-Ile-Ile-Ser-Ala-Val (Seq. ID No. 3);
Ile-Leu-Leu-Val-Val-Val-Leu-Gly-Val (Seq. ID No. 4);
Leu-Leu-Val-Val-Val-Leu-Gly-Val-Val (Seq. ID No. 5);
Arg-Leu-Leu-Gln-Glu-Thr-Glu-Leu-Val (Seq. ID No. 6);
Cys-Leu-Thr-Ser-Thr-Val-Gln-Leu-Val (Seq. ID No. 7);
Asp-Leu-Ala-Ala-Arg-Asn-Val-Leu-Val (Seq. ID No. 8);
Val-Leu-Val-Lys-Ser-Pro-Asn-His-Val (Seq. ID No. 9);
Thr-Leu-Ser-Pro-Gly-Lys-Asn-Gly-Val (Seq. ID No. 10);
Val-Leu-Gly-Val-Val-Phe-Gly-Ile-Leu (Seq. ID No. 11);
Leu-Ile-Lys-Arg-Arg-Gln-Gln-Lys-Ile (Seq. ID No. 12);
Lys-Ile-Pro-Val-Ala-Ile-Lys-Val-Leu (Seq. ID No. 13);
Ile-Leu-Asp-Glu-Ala-Tyr-Val-Met-Ala (Seq. ID No. 14);
Gln-Leu-Met-Pro-Tyr-Gly-Cys-Leu-Leu (Seq. ID No. 15);
Gln-Ile-Ala-Lys-Gly-Met-Ser-Tyr-Leu (Seq. ID No. 16);
Leu-Leu-Asn-Trp-Cys-Met-Gln-Ile-Ala (Seq. ID No. 17);
Arg-Leu-Val-His-Arg-Asp-Leu-Ala-Ala (Seq. ID No. 18);
Asp-Ile-Asp-Glu-Thr-Glu-Tyr-His-Ala (Seq. ID No. 19);
Asp-Leu-Leu-Glu-Lys-Gly-Glu-Arg-Leu (Seq. ID No. 20);
Thr-Ile-Asp-Val-Tyr-Met-Leu-Met-Val (Seq. ID No. 21);
Met-Ile-Met-Val-Lys-Cys-Trp-Met-Ile (Seq. ID No. 22);
Asp-Leu-Val-Asp-Ala-Glu-Glu-Tyr-Leu (Seq. ID No. 23);
Gly-Leu-Glu-Pro-Ser-Glu-Glu-Glu-Ala (Seq. ID No. 24); or
Tyr-Leu-Thr-Pro-Gln-Gly-Gly-Ala-Ala (Seq. ID No. 25).

Similarly, a variety of peptides designated for CD4+ T cell responses are provided which include peptides consisting essentially of:

His-Leu-Asp-Met-Leu-Arg-His-Leu-Tyr-Gln-Gly-Cys-Gln-Val-Val (Seq. ID No. 30);
Pro-Leu-Gln-Arg-Leu-Arg-Ile-Val-Arg-Gly-Thr-Gln-Leu-Phe-Glu (Seq. ID No. 31);
Leu-Arg-Ser-Leu-Thr-Glu-Ile-Leu-Lys-Gly-Gly-Val-Leu-Ile-Gln (Seq. ID No. 32);
Val-Thr-Tyr-Asn-Thr-Asp-Thr-Phe-Glu-Ser-Met-Pro-Asn-Pro-Glu (Seq. ID No. 33);
His-Leu-Arg-Glu-Val-Arg-Ala-Val-Thr-Ser-Ala-Asn-Ile-Gln-Glu (Seq. ID No. 34);
Val-Arg-Ala-Val-Thr-Ser-Ala-Asn-Ile-Gln-Glu-Phe-Ala-Gly-Cys (Seq. ID No. 35);
Asn-Ile-Gln-Glu-Phe-Ala-Gly-Cys-Lys-Lys-Ile-Phe-Gly-Ser-Leu (Seq. ID No. 36);
Gln-Val-Phe-Glu-Thr-Leu-Glu-Glu-Ile-Thr-Gly-Tyr-Leu-Tyr-Ile (Seq. ID No. 37);
Gln-Glu-Cys-Val-Glu-Glu-Cys-Arg-Val-Leu-Gln-Gly-Leu-Pro-Arg (Seq. ID No. 38);
Val-Val-Val-Leu-Gly-Val-Val-Phe-Gly-Ile-Leu-Ile-Lys-Arg-Arg (Seq. ID No. 39);
Lys-Tyr-Thr-Met-Arg-Arg-Leu-Leu-Gln-Glu-Thr-Glu-Leu-Val-Glu (Seq. ID No. 40);
Gly-Ala-Met-Pro-Asn-Gln-Ala-Gln-Met-Arg-Ile-Leu-Lys-Glu-Thr (Seq. ID No. 41);
Val-Lys-Val-Leu-Gly-Ser-Gly-Ala-Phe-Gly-Thr-Val-Tyr-Lys-Gly (Seq. ID No. 42);
Ser-Pro-Lys-Ala-Asn-Lys-Glu-Ile-Leu-Asp-Glu-Ala-Tyr-Val-Met (Seq. ID No. 43);
Gly-Val-Gly-Ser-Pro-Tyr-Val-Ser-Arg-Leu-Leu-Gly-Ile-Cys-Leu (Seq. ID No. 44);
Ser-Arg-Leu-Leu-Gly-Ile-Cys-Leu-Thr-Ser-Thr-Val-Gln-Leu-Val (Seq. ID No. 45);
Gly-Ser-Gln-Asp-Leu-Leu-Asn-Trp-Cys-Met-Gln-Ile-Ala-Lys-Gly (Seq. ID No. 46);
Val-Lys-Ile-Thr-Asp-Phe-Gly-Leu-Ala-Arg-Leu-Leu-Asp-Ile-Asp (Seq. ID No. 47);
Thr-Val-Trp-Glu-Leu-Met-Thr-Phe-Gly-Ala-Lys-Pro-Tyr-Asp-Gly (Seq. ID No. 48);
Pro-Ala-Arg-Glu-Ile-Pro-Asp-Leu-Leu-Glu-Lys-Gly-Glu-Arg-Leu (Seq. ID No. 49);
Arg-Phe-Arg-Glu-Leu-Val-Ser-Glu-Phe-Ser-Arg-Met-Ala-Arg-Asp (Seq. ID No. 50);
Glu-Asp-Asp-Asp-Met-Gly-Asp-Leu-Val-Asp-Ala-Glu-Glu-Tyr-Leu (Seq. ID No. 51);

Gly-Met-Gly-Ala-Ala-Lys-Gly-Leu-Gln-Ser-Leu-Pro-Thr-His-Asp (Seq. ID No. 52);

Thr-Cys-Ser-Pro-Gln-Pro-Glu-Tyr-Val-Asn-Gln-Pro-Asp-Val-Arg (Seq. ID No. 53);

Thr-Leu-Glu-Arg-Pro-Lys-Thr-Leu-Ser-Pro-Gly-Lys-Asn-Gly-Val (Seq. ID No. 54);

Gly-Gly-Ala-Val-Glu-Asn-Pro-Glu-Tyr-Leu-Thr-Pro-Gln-Gly-Gly (Seq. ID No. 55);

Asn-Gln-Glu-Val-Thr-Ala-Glu-Asp-Gly-Thr-Gln-Arg-Cys-Glu-Lys (Seq. ID No. 56);

Gln-Val-Ile-Arg-Gly-Arg-Ile-Leu-His-Asn-Gly-Ala-Tyr-Ser-Leu (Seq. ID No. 57);

Leu-Gln-Val-Phe-Glu-Thr-Leu-Glu-Glu-Ile-Thr-Gly-Tyr-Leu-Tyr (Seq. ID No. 58);

Ala-Ser-Pro-Leu-Thr-Ser-Ile-Ile-Ser-Ala-Val-Val-Gly-Ile-Leu (Seq. ID No. 59);

Thr-Gln-Arg-Cys-Glu-Lys-Cys-Ser-Lys-Pro-Cys-Ala-Arg-Val-Cys-Tyr-Gly-Leu (Seq. ID No. 60);

Arg-Leu-Arg-Ile-Val-Arg-Gly-Thr-Gln-Leu-Phe-Glu-Asp-Asn-Tyr-Ala-Leu (Seq. ID No. 61);

Lys-Ile-Phe-Gly-Ser-Leu-Ala-Phe-Leu-Pro-Glu-Ser-Phe-Asp-Gly-Asp (Seq. ID No. 62);

Arg-Arg-Leu-Leu-Gln-Glu-Thr-Glu-Leu-Val-Glu-Pro-Leu-Thr-Pro-Ser (Seq. ID No. 63); or

Glu-Leu-Val-Ser-Glu-Phe-Ser-Arg-Met-Ala-Arg-Asp-Pro-Gln (Seq. ID No. 64).

Additional peptides are provided and include a peptide consisting essentially of the amino acid sequence of FIG. 1 from lysine, amino acid 676, to valine, amino acid 1255 (SEQ ID NO. 69).

These and other aspects of the present invention will become evident upon reference to the following detailed description and attached drawings.

BRIEF DESCRIPTION OF THE DRAWINGS

FIG. 1 shows that p185$^{HER-2/neu}$ protein contains multiple segments with amino acid sequences appropriate for binding to class II MHC molecules. Each outlined amino acid represents the center point of an 11-mer peptide with alpha-helical periodicity and amphipathicity. Each underlined amino acid segment represents an epitope corresponding to Rothbard and Taylor motifs.

FIG. 7 pictorially illustrates that some breast cancer patients have antibodies directed to both the extracellular and intracellular domain of the HER-2/neu protein. Sera of breast cancer patients is tested against the extracellular domain ("ECD protein") or the intracellular domain ("ICD protein"), in lanes A and B, respectively.

Control sera was derived from an animal immunized with adjuvant alone. Antibody responses titered with decreasing serum concentrations. Results were reproducible in 3 separately run assays.

Figure 10A:
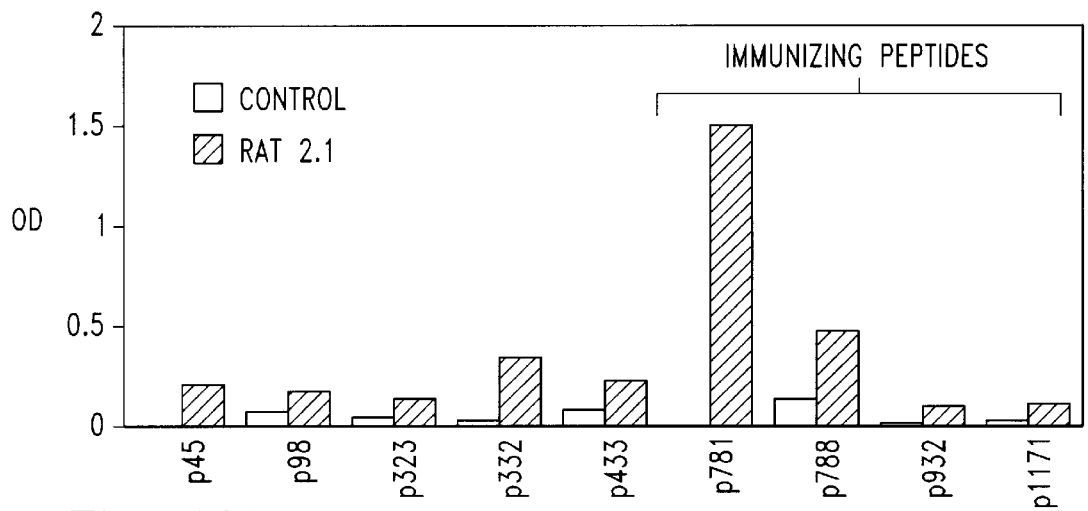
Figure 10B:
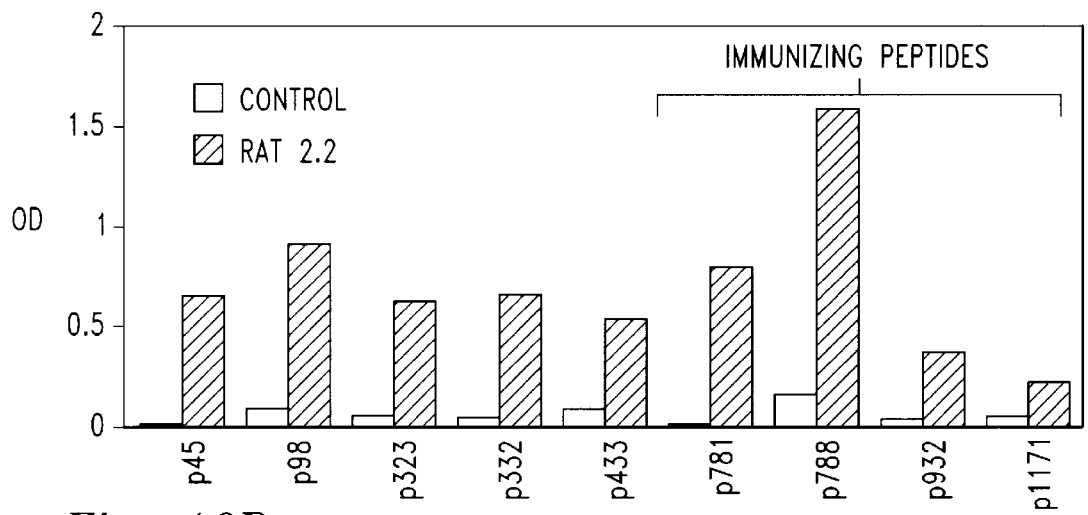
Figure 10C:
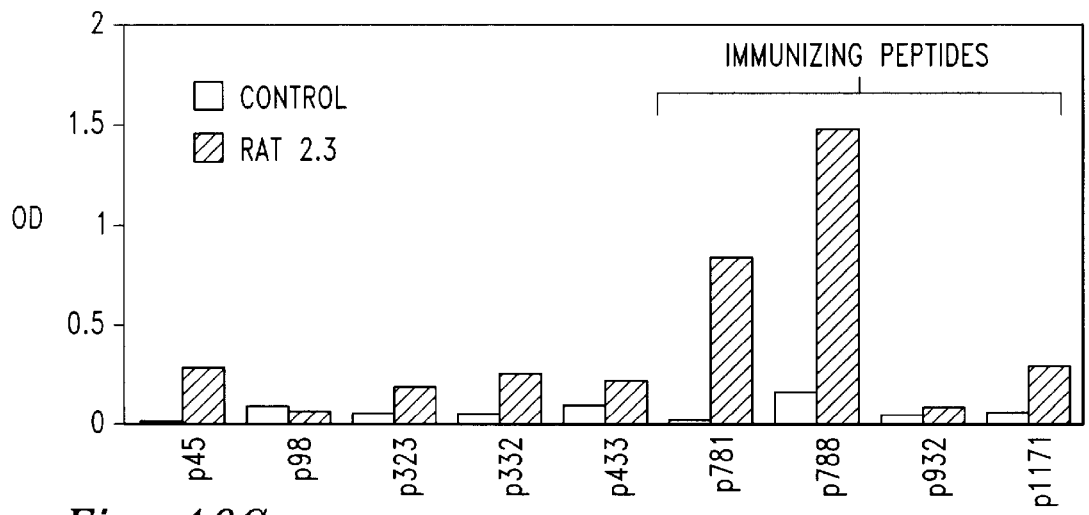

FIGS. 10A–10C graphically show that epitope analysis of ICD antibody responses demonstrates dominant B cell epitopes as well as "determinant spreading" between domains. ELISA analysis for peptide epitopes was performed. Each animal's sera (FIGS. 10A–10C) was evaluated at dilutions of 1:25, 1:50, 1:100, and 1:200 for each peptide analyzed. Antibody responses titered with decreasing serum concentrations. All data shown is at a rat sera concentration of 1:50. Control sera analyzed was pooled sera from 5 non-immunized animals. Results were reproducible in 3 separately run assays.

Figure 11A:
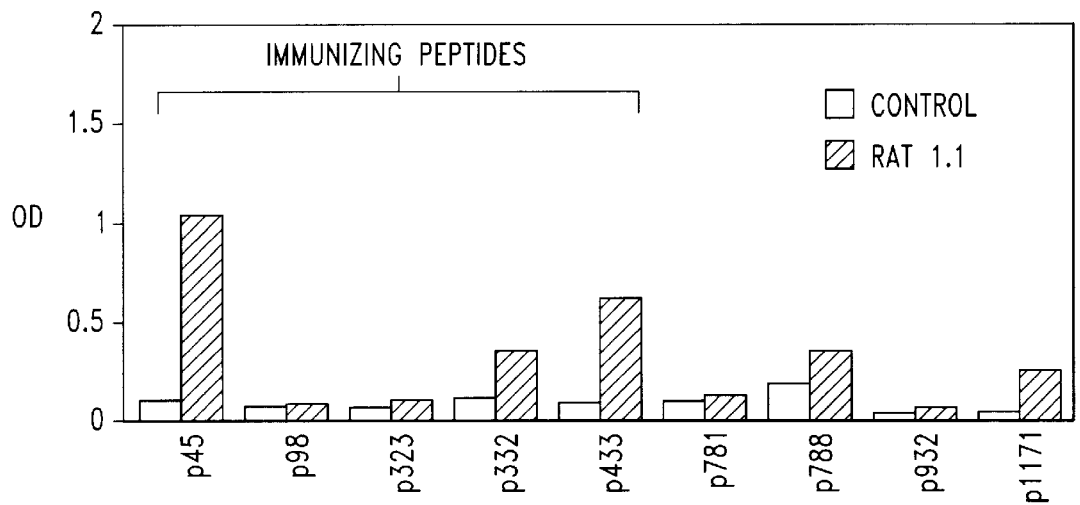
Figure 11B:
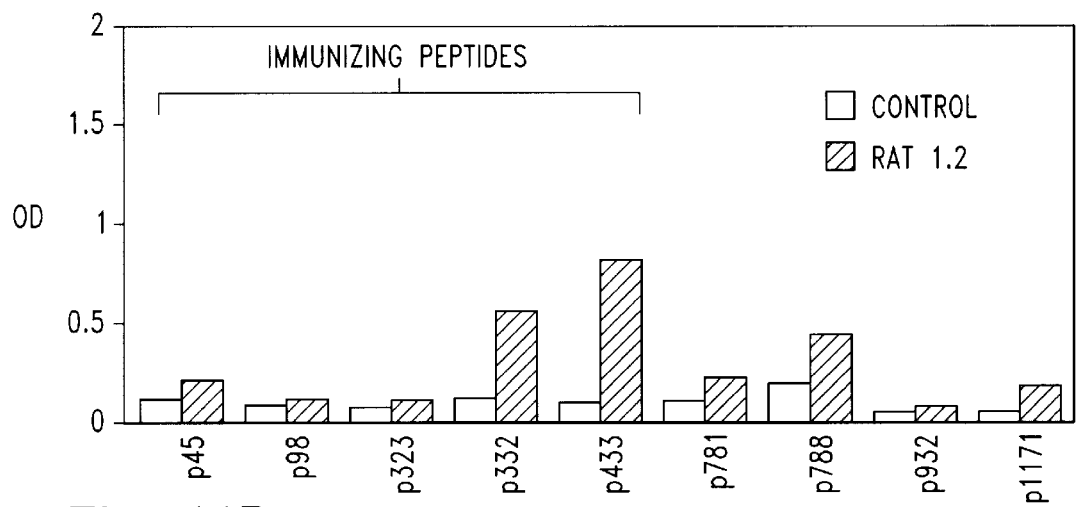
Figure 11C:
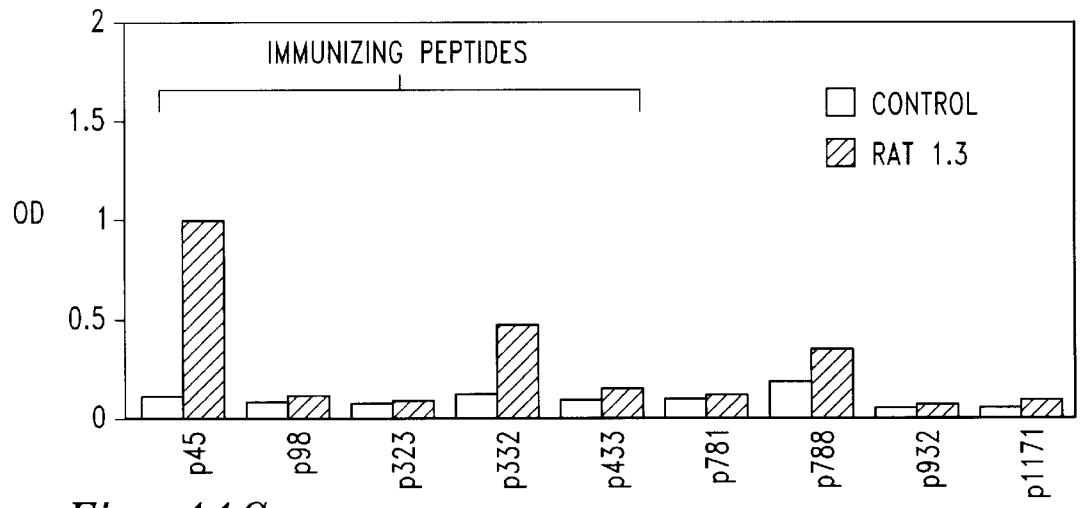

FIGS. 11A–11B and 11C graphically show that epitope analysis of ECD antibody responses demonstrates dominant B cell epitopes. ELISA analysis for peptide epitopes was performed. Each animal's sera was evaluated at dilutions of 1:25, 1:50, 1:100, and 1:200 for each peptide analyzed. Antibody responses titered with decreasing serum concentrations. All data shown is at a rat sera concentration of 1:50. Control sera analyzed was pooled sera from 5 non-immunized animals. Results were reproducible in 3 separately run assays.

Figure 12:
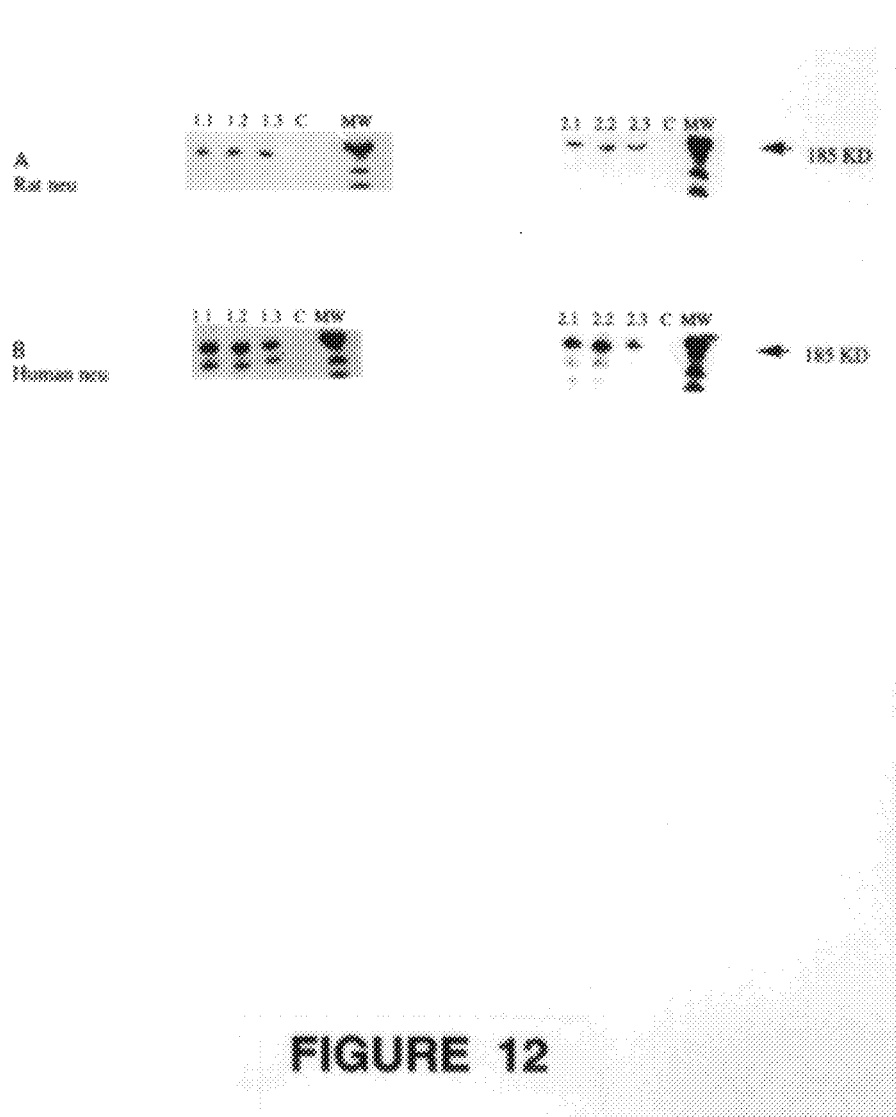

FIG. 12 pictorially illustrates that antibodies elicited by immunization to either ICD or ECD peptides are specific for and can immunoprecipitate both rat neu protein and human HER-2/neu protein. FIG. 12A shows the results of an immunoprecipitation experiment with immunized rat sera and lysates of DHFRG-8. Each sera was able to immunoprecipitate rat neu from the cell lysates. The immunoprecipitates were resolved on a 7.5% SDS-acrylamide gel and transferred to nitrocellulose. The blots were probed with primary antibody, c-neu-Ab-3, at a 1:1000 dilution. Control sera of an animal immunized with the adjuvant alone showed no evidence of reactivity to rat neu. FIG. 12B depicts the results of an immunoprecipitation experiment with immunized rat sera and lysates of SKBR3, a source of human neu. Immunoblotting was performed in an identical manner and all experimental animal sera were able to immunoprecipitate human neu. The control sera, again, showed no evidence of reactivity.

Figure 13:
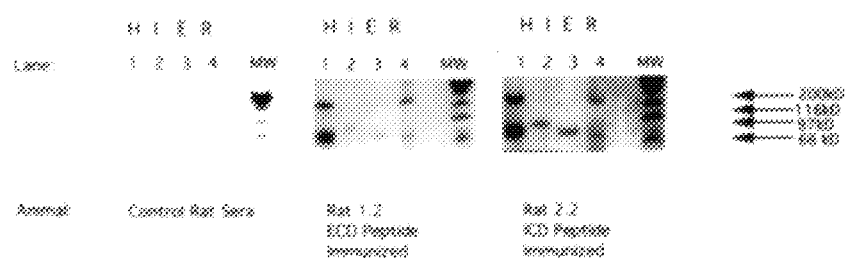

FIG. 13 pictorially illustrates that B cell epitopes that are cross reactive between human and rat neu are present in both domains of the protein. Shown here are the results of Western blot analysis of protein domain epitope mapping from representative animals in each immunized group. Animal 1.2 was immunized with the ECD group of peptides, animal 2.2 with the ICD group of peptides, and the control animal was immunized with adjuvant alone. Proteins were electrophoresed. After transfer to nitrocellulose the blots were incubated for 18 hours in rat sera at a 1:500 dilution. Antibody responses were detected with a second step goat anti-rat Ig HRP antibody at a dilution of 1:5000. Responses were detected to both human and rat neu as well as to both human ICD and ECD domain recombinant proteins. Antibody responses to these proteins could not be detected in the control animal which was immunized with adjuvant alone. Although data are shown here for animals 1.2, 2.2, and control, all animals in each group had the same pattern of response.

Figure 14A:
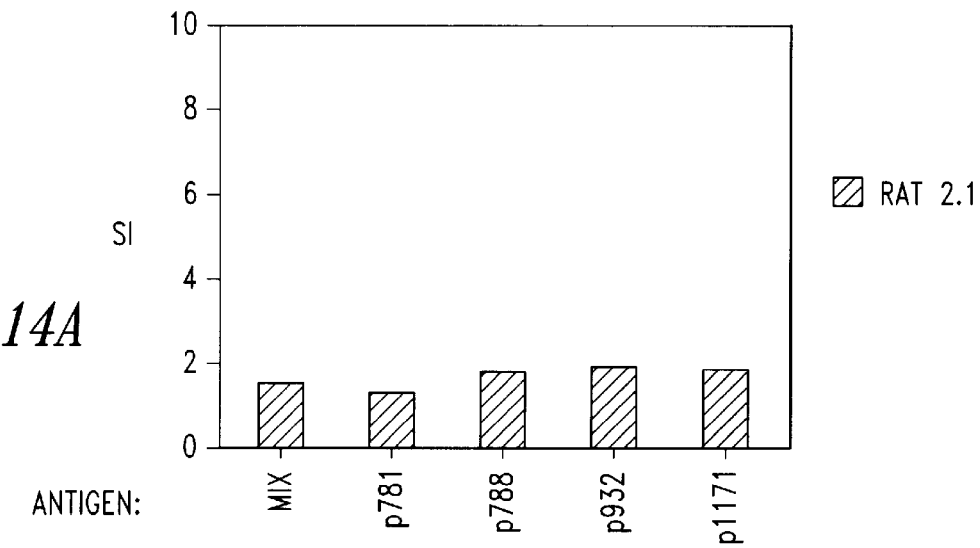
Figure 14B:
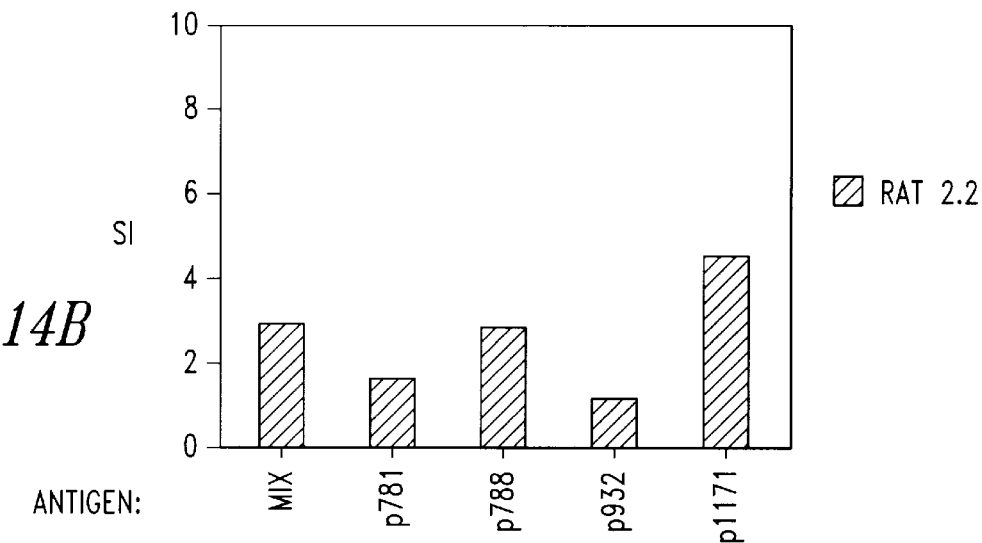
Figure 14C:
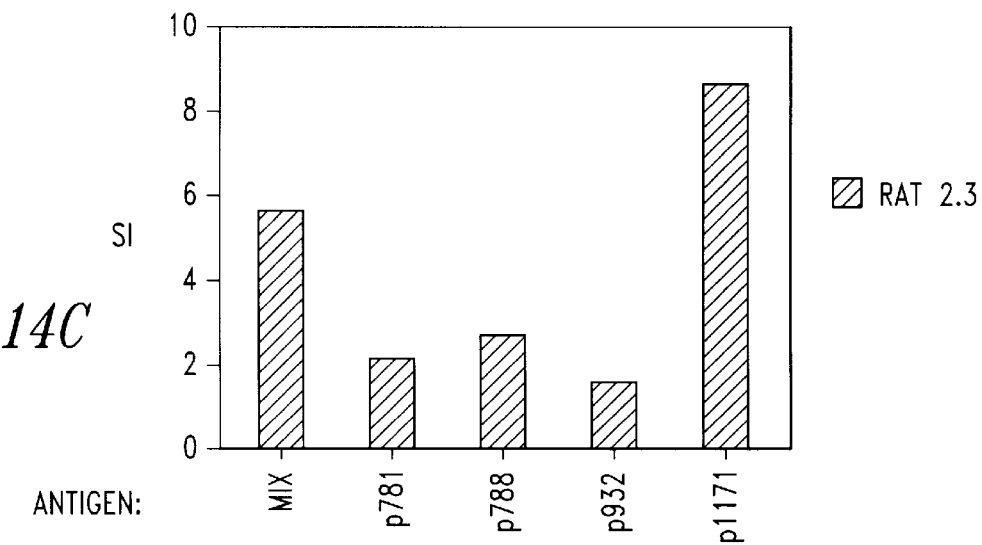

FIGS. 14A–14C graphically illustrate that immunization of rats with ICD peptides elicits neu peptide-specific T cell responses. $2\times10^5$ immunized spleen cells were incubated with 25 µg/ml of the various peptides. The "Mix" group consisted of 25 µg/ml each of the immunizing peptides. A proliferation assay was performed. Each experimental group was done in 6 well replicates. The data is expressed in terms of a stimulation index (SI) which is the mean of the experimental wells divided by the mean of the control (no antigen) wells. Stimulation indices greater than 2 are considered to be indicative of a primed response. Animals immunized with adjuvant alone showed no stimulation index greater than 0.9 to any of the tested peptides (data not shown).

Figure 15:
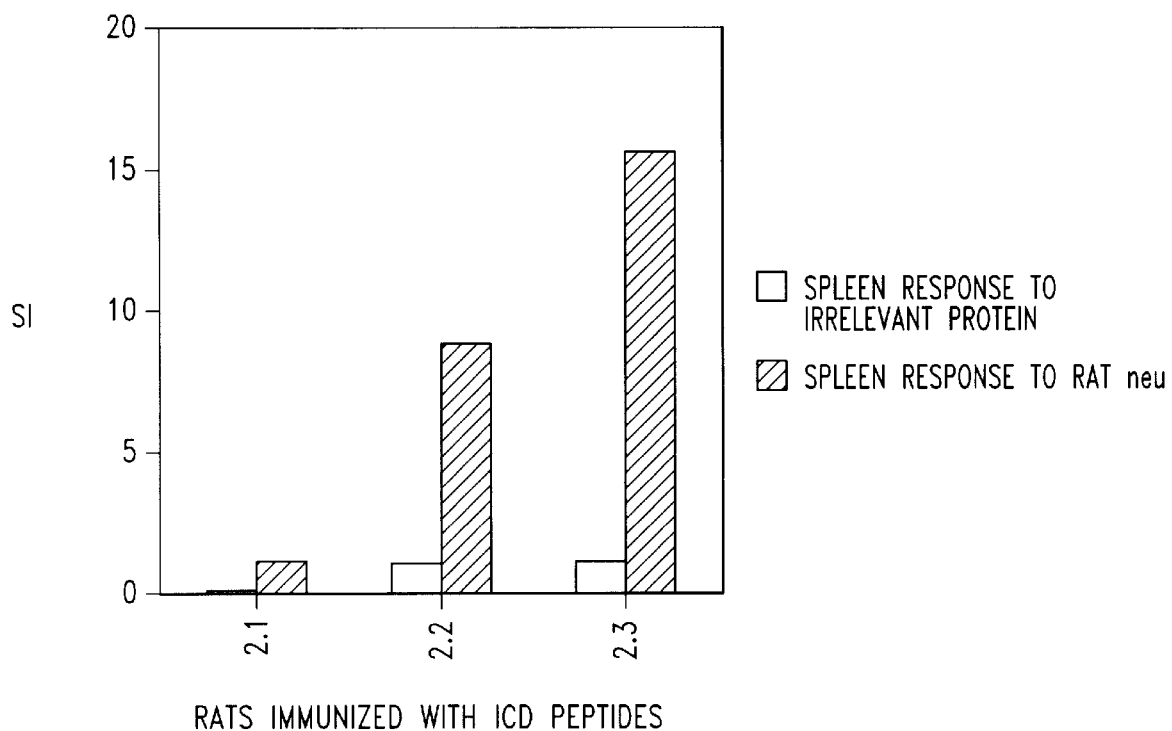

FIG. 15 graphically illustrates that immunization of rats with ICD peptides elicits neu protein-specific T cell responses. $1\times10^5$ cultured T cells derived from immunized spleen were incubated with $1\times10^5$ syngeneic spleen as APC (antigen presenting cells) and 1 µg/ml of purified rat neu protein. Each experimental group was done in 6 well replicates. The data is expressed in terms of a stimulation index which is the mean of the experimental wells divided by the mean of the control (no antigen) wells. Stimulation indices greater than 2 are considered to be indicative of a primed response. Wild type ras protein was the irrelevant protein used in the assay.

Figure 16A:
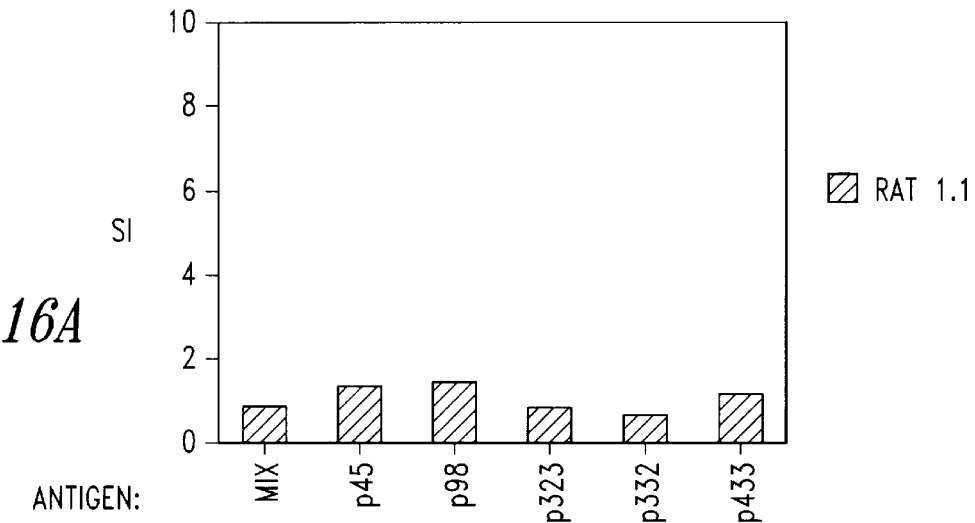
Figure 16B:
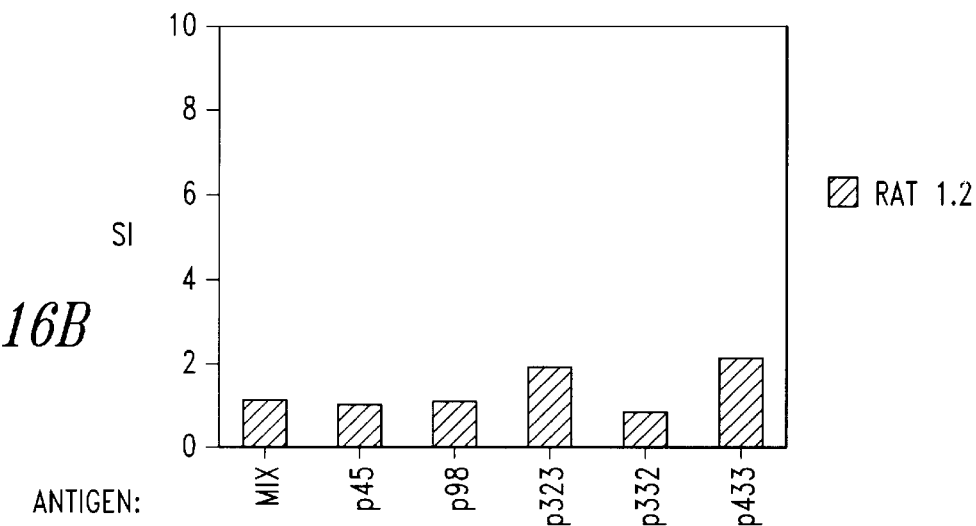
Figure 16C:
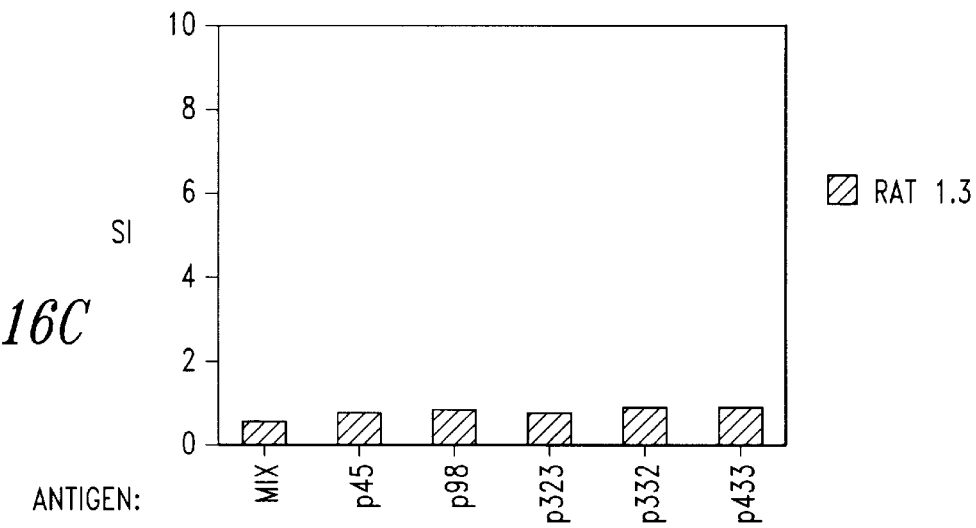

FIGS. 16A–16C graphically show that immunization of rats with ECD peptides elicits only weak peptide-specific T cell responses. $2\times10^5$ immunized spleen cells were incubated with 25 µg/ml of the various peptides. The "Mix" group consisted of 25 µg/ml each of the immunizing peptides. Each experimental group was done in 6 well replicates. The data is expressed in terms of a stimulation index which is the mean of the experimental wells divided by the mean of the control (no antigen) wells. Stimulation indices greater than 2 are considered to be indicative of a primed response. Animals immunized with adjuvant alone showed no stimulation index greater than 1.0 to any of the tested peptides (data not shown).

Figure 17:
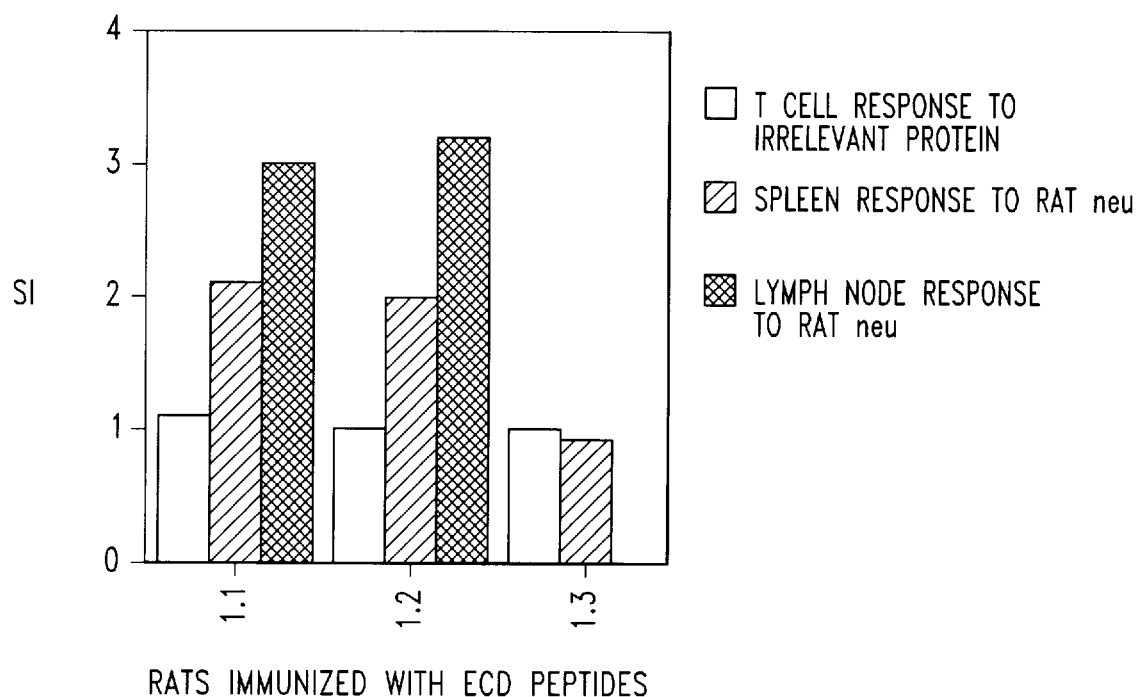

FIG. 17 graphically shows that immunization of rats with ECD peptides elicits weak, but positive, responses to neu protein. $1\times10^5$ cultured T cells derived from immunized spleen or lymph nodes were incubated with $1\times10^5$ syngeneic spleen as APC and 1 µg/ml of purified rat neu protein. Each experimental group was done in 6 well replicates. The data is expressed in terms of a stimulation index which is the mean of the experimental wells divided by the mean of the control (no antigen) wells. Stimulation indices greater than 2 are considered to be indicative of a primed response. Wild type ras protein was the irrelevant protein used in the assay.

DETAILED DESCRIPTION OF THE INVENTION

Prior to setting forth the invention, it may be helpful to an understanding thereof to set forth definitions of certain terms to be used hereinafter.

HER-2/neu Protein—as used herein, refers to the p185 protein (also known as c-erbB2) and peptides thereof which are recognized by helper T cells or cytotoxic T cells; and may be naturally derived, synthetically produced, genetically engineered, or a functional equivalent thereof, e.g., where one or more amino acids are replaced by other amino acid(s) or non-amino acid(s) which do not substantially affect function.

Proliferation of T cells—as used herein, includes the multiplication of T cells as well as the stimulation of T cells leading to multiplication, i.e., the initiation of events leading to mitosis and mitosis itself. Methods for detecting proliferation of T cells are discussed below.

As noted above, the present invention is directed toward methods and compositions for the diagnosis, monitoring and treatment of malignancies in a warm-blooded animal, wherein an amplified HER-2/neu gene is associated with the malignancies. Association of an amplified HER-2/neu gene with a malignancy does not require that the protein expression product of the gene be present on the tumor. For example, overexpression of the protein expression product may be involved with initiation of a tumor, but the protein expression may subsequently be lost. An effective autochthonous immune response may convert a HER-2/neu positive tumor to HER-2/neu negative, but existent immunity will be present and allow diagnosis.

More specifically, the disclosure of the present invention, in one aspect, shows that the protein expression product of the HER-2/neu gene can be recognized by thymus-dependent lymphocytes (hereinafter "T cells") and, therefore, the autochthonous immune T cell response can be utilized to diagnose, monitor and treat malignancies in which such a protein is or has been overexpressed. The disclosure of the present invention also shows, in another aspect, that sera of patients with a malignancy, in which an amplified HER-2/neu oncogene is associated, contain antibodies to HER-2/neu protein. The autochthonous antibody response can be used to diagnose, monitor and treat malignancies in which such a protein is overexpressed.

It is well known that the two major arms of the immune system are: (1) cell-mediated immunity with immune T cells and (2) humoral immunity with antibodies. Further, the immune system normally functions to recognize and destroy any foreign or aberrant cells in the body. Since the HER-2/neu protein is expressed by some normal cells, tolerance and/or anergy (i.e., diminished reactivity to a specific antigen) is expected. Thus, it is surprising that, as disclosed within the present invention, both T cell and antibody responses to HER-2/neu are detected.

In general, $CD4^+$ T cell populations are considered to function as helpers/inducers through the release of lymphokines when stimulated by a specific antigen; however, a subset of $CD4^+$ cells can act as cytotoxic T lymphocytes (CTL). Similarly, $CD8^+$ T cells are considered to function by directly lysing antigenic targets; however, under a variety of circumstances they can secrete lymphokines to provide helper or DTH function. Despite the potential of overlapping function, the phenotypic CD4 and CD8 markers are linked to the recognition of peptides bound to class II or class I MHC antigens. The recognition of antigen in the context of class II or class I MHC mandates that $CD4^+$ and $CD8^+$ T cells respond to different antigens or the same antigen presented under different circumstances. The binding of immunogenic peptides to class II MHC antigens most commonly occurs for antigens ingested by antigen presenting cells. Therefore, $CD4^+$ T cells generally recognize antigens that have been external to the tumor cells. By contrast, under normal circumstances, binding of peptides to class I MHC occurs only for proteins present in the cytosol and synthesized by the target itself, proteins in the external environment are excluded. An exception to this is the binding of exogenous peptides with a precise class I binding motif which are present outside the cell in high concentration. Thus, $CD4^+$ and $CD8^+$ T cells have broadly different functions and tend to recognize different antigens as a reflection of where the antigens normally reside.

As disclosed within the present invention, the protein product expressed by the HER-2/neu oncogene is recognized by T cells. Such a protein expression product "turns over" within cells, i.e., undergoes a cycle wherein a synthesized protein functions and then eventually is degraded and replaced by a newly synthesized molecule. During the protein life cycle, peptide fragments from the protein bind to major histocompatibility complex (MHC) antigens. By display of a peptide bound to MHC antigen on the cell surface and recognition by host T cells of the combination of peptide plus self MHC antigen, a malignant cell will be immunogenic to T cells. The exquisite specificity of the T cell receptor enables individual T cells to discriminate between protein fragments which differ by a single amino acid residue.

During the immune response to a peptide, T cells expressing a T cell receptor with high affinity binding of the peptide-MHC complex will bind to the peptide-MHC complex and thereby become activated and induced to proliferate. In the first encounter with a peptide, small numbers of immune T cells will secrete lymphokines, proliferate and differentiate into effector and memory T cells. The primary immune response will occur in vivo but has been difficult to detect in vitro. Subsequent encounter with the same antigen by the memory T cell will lead to a faster and more intense immune response. The secondary response will occur either in vivo or in vitro. The in vitro response is easily gauged by measuring the degree of proliferation, the degree of cytokine production, or the generation of cytolytic activity of the T cell population re-exposed in the antigen. Substantial proliferation of the T cell population in response to a particular antigen is considered to be indicative of prior exposure or priming to the antigen.

Within one aspect of the present invention, a malignancy in which a HER-2/neu oncogene is associated may be detected. Representative examples of such malignancies include breast, ovarian, colon, lung and prostate cancers. An immune response to the HER-2/neu protein, once generated, can be long-lived and can be detected long after immunization, regardless of whether the protein is present or absent in the body at the time of testing. In one embodiment, prior exposure of a warm-blooded animal, such as humans, to the HER-2/neu protein can be detected by examining for the presence or absence of specific activation of $CD4^+$ or $CD8^+$ T cells. More specifically, T cells isolated from an individual by routine techniques (such as by Ficoll/Hypaque density gradient centrifugation of peripheral blood lymphocytes) are incubated with HER-2/neu protein. For example, T cells may be incubated in vitro for 2–9 days (typically 4 days) at 37° C. with HER-2/neu protein (typically, 5 µg/ml of whole protein or 25 µg/ml of an appropriate peptide or graded numbers of cells synthesizing HER-2/neu protein). It may be desirable to incubate another aliquot of a T cell sample in the absence of HER-2/neu protein to serve as a control.

Specific activation of $CD4^+$ or $CD8^+$ T cells may be detected in a variety of ways. Methods for detecting specific T cell activation include detecting the proliferation of T cells, the production of cytokines (e.g., lymphokines), or the generation of cytolytic activity (i.e., generation of cytotoxic T cells specific for HER-2/neu protein). For $CD4^+$ T cells, a preferred method for detecting specific T cell activation is the detection of the proliferation of T cells. For $CD8^+$ T cells, a preferred method for detecting specific T cell activation is the detection of the generation of cytolytic activity.

Detection of the proliferation of T cells may be accomplished by a variety of known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to intact p185$^{HER-2/neu}$ protein or peptide may be quantified.

Intact p185$^{HER-2/neu}$ protein or peptides thereof which are recognized by cytotoxic T cells may be used within the present invention. The peptides may be naturally derived or produced based upon an identified sequence. The peptides for CD8$^+$ T cell responses are generally 8–10 amino acids in length and the peptides for CD4$^+$ T cell responses are longer, e.g., 15–18 amino acids in length. Peptides for CD8$^+$ T cell responses vary according to each individual's class I MHC molecules. An example of peptides appropriate for CD8$^+$ T cell responses (elicited by peptides presented by HLA-A2.1 class I MHC molecules) are peptides which are 8–10 amino acids in length and contain a leucine at position 2 and/or a leucine or valine at position 9. Examples of peptides (designated by one letter abbreviations for amino acids and followed in parentheses by which residues of p185 they correspond) suitable within the present invention for CD8$^+$ T cell responses in individuals that are HLA-A2.1 include peptides consisting essentially of: HLYQGCQVV (p48–56) (Seq. ID No. 1); QLFEDNYAL (p106–114) (Seq. ID No. 26); KIFGSLAFL (p369–377) (Seq. ID No. 27); PLQPEQLQV (p391–399) (Seq. ID No. 2); PLTSIISAV (p650–658) (Seq. ID No. 3); ILLVVVLGV (p661–669) (Seq. ID No. 4); LLVVVLGVV (p662–670) (Seq. ID No. 5); RLLQETELV (p689–697) (Seq. ID No. 6); ILDEAYVMAGV (p767–777) (Seq. ID No. 28); VMAGVGSPYV (p773–782) (Seq. ID No. 29); CLTSTVQLV (p789–797) (Seq. ID No. 7); DLAARNVLV (p845–853) (Seq. ID No. 8); VLVKSPNHV (p851–859) (Seq. ID No. 9); TLSPGKNGV (p1172–1180) (Seq. ID No. 10); VLGVVFGIL (p666–674) (Seq. ID No. 11); LIKRRQQKI (p674–682) (Seq. ID No. 12); KIPVAIKVL (p747–755) (Seq. ID No. 13); ILDEAYVMA (p767–775) (Seq. ID No. 14); QLMPYGCLL (p799–807) (Seq. ID No. 15); QIAKGMSYL (p829–836) (Seq. ID No. 16); LLNWCMQIA (p822–830) (Seq. ID No. 17); RLVHRDLAA (p840–848) (Seq. ID No. 18); DIDETEYHA (p871–879) (Seq. ID No. 19); DLLEKGERL (p933–941) (Seq. ID No. 20); TIDVYMLMV (p948–956) (Seq. ID No. 21); MIMVKCWMI (p953–961) (Seq. ID No. 22); DLVDAEEYL (p1016–1024) (Seq. ID No. 23); GLEPSEEEA (p1062–1070) (Seq. ID No. 24); or YLTPQGGAA (p1196–1204) (Seq. ID No. 25).

Peptides for CD4$^+$ T cell responses vary according to each individual's class II MHC molecules. Examples of peptides suitable within the present invention for CD4$^+$ T cell responses include peptides consisting essentially of: HLDMLRHLYQGCQVV (p42–56) (Seq. ID No. 30); PLQRLRIVRGTQLFE (p95–109) (Seq. ID No. 31); RLRIVRGTQLFEDNYAL (p98–114) (Seq. ID No. 61); LRSLTEILKGGVLIQ (p142–156) (Seq. ID No. 32); VTYNTDTFESMPNPE (p272–286) (Seq. ID No. 33); NQEVTAEDGTQRCEK (p319–333) (Seq. ID No. 56); TQRCEKCSKPCARVCYGL (p328–345) (Seq. ID No. 60); HLREVRAVTSANIQE (p349–363) (Seq. ID No. 34); VRAVTSANIQEFAGC (p353–367) (Seq. ID No. 35); NIQEFAGCKKIFGSL (p360–374) (Seq. ID No. 36); KIFGSLAFLPESFDGD (p369–384) (Seq. ID No. 62); LQVFETLEEITGYLY (p397–411) (Seq. ID No. 58); QVFETLEEITGYLYI (p398–412) (Seq. ID No. 37); QVIRGRILHNGAYSL (p429–443) (Seq. ID No. 57); QECVEECRVLQGLPR (p538–552) (Seq. ID No. 38); ASPLTSIISAVVGIL (p648–662) (Seq. ID No. 59); VVVLGVVFGILIKRR (p664–678) (Seq. ID No. 39); KYTMRRLLQETELVE (p684–698) (Seq. ID No. 40); RRLLQETELVEPLTPS (p688–703) (Seq. ID No. 63); GAMPNQAQMRILKET (p704–718) (Seq. ID No. 41); VKVLGSGAFGTVYKG (p723–737) (Seq. ID No. 42); SPKANKEILDEAYVM (p760–774) (Seq. ID No. 43); GVGSPYVSRLLGICL (p776–790) (Seq. ID No. 44); SRLLGICLTSTVQLV (p783–797) (Seq. ID No. 45); GSQDLLNWCMQIAKG (p818–832) (Seq. ID No. 46); VKITDFGLARLLDID (p859–873) (Seq. ID No. 47); TVWELMTFGAKPYDG (p911–925) (Seq. ID No. 48); PAREIPDLLEKGERL (p927–941) (Seq. ID No. 49); RFRELVSEFSRMARD (p968–982) (Seq. ID No. 50); ELVSEFSRMARDPQ (p971–984) (Seq. ID No. 64); EDDDMGDLVDAEEYL (p1010–1024) (Seq. ID No. 51); GMGAAKGLQSLPTHD (p1091–1105) (Seq. ID No. 52); TCSPQPEYVNQPDVR (p1132–1146) (Seq. ID No. 53); TLERPKTLSPGKNGV (p1166–1180) (Seq. ID No. 54); or GGAVENPEYLTPQGG (p1188–1202) (Seq. ID No. 55).

It will be evident to those of ordinary skill in the art that other peptides may be produced for use within the present invention, both for the HLA-A2.1 class I MHC molecule as well as for the other class I and class II molecules. A variety of techniques are well known for isolating or constructing peptides. Suitable peptides are readily identified based upon the disclosure provided herein. Additional suitable peptides include those which are longer in length. For example, another peptide has an amino acid sequence corresponding to that disclosed in FIG. 1 beginning at about the lysine residue at amino acid position 676 and extending to about the valine residue at amino acid position 1255. Such a peptide may be extended (e.g., by the addition of one or more amino acid residues selected, for example, from position 675 to about position 646 of FIG. 1) and/or truncated (e.g., by the deletion of one or more amino acid residues from the carboxyl terminus which is position 1255 of FIG. 1). Alternatively, suitable peptides may be variations on other preferred peptides disclosed herein. For example, variations on the peptide designated herein as p650–658 include the extension and/or truncation by the addition or deletion, respectively, of one or more amino acid residues beginning at either position 650 or position 658 or both positions. As an example, four amino acids are removed from the amino terminus of p650–658 and four amino acids, such as the four adjacent to position 658, are added to its carboxyl terminus. Although this particular peptide variation results in a peptide with the same number of total amino acids (nine), a peptide variation on a preferred peptide need not be identical in length. Variations in amino acid sequence that yield peptides having substantially the same desired biological activity are within the scope of the present invention.

For therapeutic purposes, CD4$^+$ or CD8$^+$ T cells that proliferate in the presence of HER-2/neu protein can be expanded in number either in vitro or in vivo. Proliferation of such T cells in vitro may be accomplished in a variety of ways. For example, the T cells can be re-exposed to HER-2/neu protein. It may be desirable to repeat the exposure of T cells to the HER-2/neu protein to induce proliferation. It may be further desirable to include T cell growth factors, such as interleukin-2, and/or stimulator cells which synthesize HER-2/neu protein. The addition of stimulator cells is preferred where generating CD8⁺ T cell responses. HER-2/neu protein-specific T cells can be grown to large numbers in vitro with retention of specificity in response to intermittent restimulation with the immunizing HER-2/neu protein. Briefly, for the primary in vitro stimulation (IVS), large numbers of lymphocytes (e.g., greater than $4\times10^7$) are placed in flasks with media containing human serum. HER-2/neu protein (e.g., peptide at 10 μg/ml) is added directly as well as 5 μg/ml tetanus toxoid. The flasks are incubated at 37° C. for 7 days. For the second IVS, at the end of the 7 days, T cells are harvested and placed in new flasks with $2-3\times10^7$ irradiated peripheral blood mononuclear cells. HER-2/neu protein (e.g., peptide at 10 μg/ml is added directly). The flasks are incubated at 37° C. for 7 days. On day 2 and day 4 after the second IVS, 2–5 units of interleukin-2 (IL-2) is added. For the third IVS, the T cells are placed in wells (e.g., 24 well plates). The T cells are stimulated with the individual's own EBV transformed B cells coated with the peptide. IL-2 is added on days 2 and 4 of each cycle. As soon as the cells are shown to be specific cytotoxic T cells, they are changed to a 10 day stimulation cycle with higher IL-2 (20 units) on days 2, 4 and 6 to expand them.

Alternatively, one or more T cells that proliferate in the presence of HER-2/neu protein can be expanded in number by cloning. Methods for cloning cells are well known in the art. For example, T cell lines may be established in vitro and cloned by limiting dilution. Responder T cells are purified from the peripheral blood of sensitized patients by density gradient centrifugation and sheep red cell resetting and established in culture by stimulating with the nominal antigen in the presence of irradiated autologous filler cells. In order to generate CD4⁺ T cell lines, HER-2/neu protein is used as the antigenic stimulus and autologous peripheral blood lymphocytes (PBL) or lymphoblastoid cell lines (LCL) immortalized by infection with Epstein Barr virus are used as antigen presenting cells. In order to generate CD8⁺ T cell lines, autologous antigen-presenting cells transfected with an expression vector which produces relevant HER-2/neu protein may be used as stimulator cells. Established T cell lines are cloned 2–4 days following antigen stimulation by plating stimulated T cells at a frequency of 0.5 cells per well in 96-well flat-bottom plates with $1\times10^6$ irradiated PBL or LCL cells and recombinant interleukin-2 (rIL2) (50 U/ml). Wells with established clonal growth are identified at approximately 2–3 weeks after initial plating and restimulated with appropriate antigen in the presence of autologous antigen-presenting cells, then subsequently expanded by the addition of low doses of rIL2(10 U/ml) 2–3 days following antigen stimulation. T cell clones are maintained in 24-well plates by periodic restimulation with antigen and rIL2 approximately every two weeks.

Regardless of how an individual's T cells are proliferated in vitro, the T cells may be administered to the individual as an anti-cancer composition in an amount effective for therapeutic attack against a tumor. Thus, a patient's own T cells (autochthonous T cells) can be used as reagents to mediate specific tumor therapy. Typically, about $1\times10^9$ to $1\times10^{11}$ T cells/M² will be administered intravenously or intracavitary, e.g., in pleural or peritoneal cavities, or in the bed of a resected tumor. It will be evident to those skilled in the art that the number and frequency of administration will be dependent upon the response of the patient. Pharmaceutically suitable carriers or diluents for T cells include physiological saline or sera. It will be recognized by one skilled in the art that the composition should be prepared in sterile form.

T cells may also be proliferated in vivo. For example, immunization of an individual with a HER-2/neu peptide (i.e., as a vaccine) can induce continued expansion in the number of T cells necessary for therapeutic attack against a tumor in which the HER-2/neu oncogene is associated. Typically, about 0.01 μg/kg to about 100 mg/kg body weight will be administered by the intradermal, subcutaneous or intravenous route. A preferred dosage is about 1 μg/kg to about 1 mg/kg, with about 5 μg/kg to about 200 μg/kg particularly preferred. It will be evident to those skilled in the art that the number and frequency of administration will be dependent upon the response of the patient. It may be desirable to administer the HER-2/neu peptide repetitively. It will be evident to those skilled in this art that more than one HER-2/neu peptide may be administered, either simultaneously or sequentially. For example, a combination of about 8–15 peptides may be used for immunization. Preferred peptides for immunization are those that include all or a portion of the amino acid sequence shown in FIG. 1 beginning at about the lysine residue at amino acid position 676 and extending to about the valine residue at amino acid position 1255. One or more peptides from other portions of the amino acid sequence shown in FIG. 1 may be added to one or more of the preferred peptides. Neither intact p185$^{HER-2/neu}$ protein nor a peptide having the amino acid sequence of its entire extracellular domain (i.e., a peptide having an amino acid sequence of the entire amino acid sequence shown in FIG. 1 up to amino acid position 650, plus or minus about one to five positions, and with or without the first 21 amino acid positions) are used alone for immunization.

In addition to the HER-2/neu peptide (which functions as an antigen), it may be desirable to include other components in the vaccine, such as a vehicle for antigen delivery and immunostimulatory substances designed to enhance the protein's immunogenicity. Examples of vehicles for antigen delivery include aluminum salts, water-in-oil emulsions, biodegradable oil vehicles, oil-in-water emulsions, biodegradable microcapsules, and liposomes. Examples of immunostimulatory substances (adjuvants) include N-acetylmuramyl-L-alanine-D-isoglutamine (MDP), lipopoly-saccharides (LPS), glucan, IL-12, GM-CSF, gamma interferon and IL-15. It will be evident to those skilled in this art that a HER-2/neu peptide may be prepared synthetically or that a portion of the protein (naturally-derived or synthetic) may be used. When a peptide is used without additional sequences, it may be desirable to couple the peptide hapten to a carrier substance, such as keyhole limpet hemocyanin.

The present invention also discloses that HER-2/neu protein, in addition to being immunogenic to T cells, appears to stimulate B-cells to produce antibodies capable of recognizing HER-2/neu protein. Detection of such antibodies provides another way to diagnose a malignancy in which a HER-2/neu oncogene is associated with the malignancy. Antibodies specific (i.e., which exhibit a binding affinity of about 10⁷ liters/mole or better) for HER-2/neu protein may be found in a variety of body fluids including sera and ascites. Briefly, a body fluid sample is isolated from a warm-blooded animal, such as a human, for whom it is desired to determine whether antibodies specific for HER-2/neu are present. The body fluid is incubated with HER-2/neu protein under conditions and for a time sufficient to permit immunocomplexes to form between the protein and antibodies specific for the protein. For example, a body fluid and HER-2/neu protein may be incubated at 4° C. for 24–48 hours. Following the incubation, the reaction mixture is tested for the presence of immunocomplexes. Detection of one or more immunocomplexes formed between HER-2/neu protein and antibodies specific for HER-2/neu protein may be accomplished by a variety of known techniques, such as radioimmunoassays (RIA) and enzyme linked immunosorbent assays (ELISA).

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods,* E. and S. Livingstone, Edinburgh, 1970); the "western blot" method of Gordon et al. (U.S. Pat. No. 4,452,901); immunoprecipitation of labeled ligand (Brown et al., *J. Biol. Chem.* 255: 4980–4983, 1980); enzyme-linked immunosorbent assays as described by, for example, Raines and Ross (*J. Biol. Chem.* 257: 5154–5160, 1982); immunocytochemical techniques, including the use of fluorochromes (Brooks et al., *Clin. Exp. Immunol.* 39: 477, 1980); and neutralization of activity [Bowen-Pope et al., *Proc. Natl. Acad. Sci. USA* 81: 2396–2400 (1984)], all of which are hereby incorporated by reference. In addition to the immunoassays described above, a number of other immunoassays are available, including those described in U.S. Pat. Nos.: 3,817,827; 3,850,752; 3,901,654; 3,935,074; 3,984,533; 3,996,345; 4,034,074; and 4,098,876, all of which are herein incorporated by reference.

For detection purposes, HER-2/neu protein ("antigen") may either be labeled or unlabeled. When unlabeled, the antigen find use in agglutination assays. In addition, unlabeled antigen can be used in combination with labeled molecules that are reactive with immunocomplexes, or in combination with labeled antibodies (second antibodies) that are reactive with the antibody directed against HER-2/neu protein, such as antibodies specific for immunoglobulin. Alternatively, the antigen can be directly labeled. Where it is labeled, the reporter group can include radioisotopes, fluorophores, enzymes, luminescers, or dye particles. These and other labels are well known in the art and are described, for example, in the following U.S. Pat. Nos.: 3,766,162; 3,791,932; 3,817,837; 3,996,345; and 4,233,402.

Typically in an ELISA assay, antigen is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1%–5.0% by weight) of protein, such as BSA, NGS, or BLOTTO. After incubating for a sufficient length of time to allow specific binding to occur, the well is washed to remove unbound protein and then incubated with an anti-species specific immunoglobulin antibody labeled with a reporter group. The reporter group can be chosen from a variety of enzymes, including horseradish peroxidase, beta-galactosidase, alkaline phosphatase, and glucose oxidase. Sufficient time is allowed for specific binding to occur, then the well is again washed to remove unbound conjugate, and the substrate for the enzyme is added. Color is allowed to develop and the optical density of the contents of the well is determined visually or instrumentally.

In one preferred embodiment of this aspect of the present invention, a reporter group is bound to HER-2/neu protein. The step of detecting immunocomplexes involves removing substantially any unbound HER-2/neu protein and then detecting the presence or absence of the reporter group.

In another preferred embodiment, a reporter group is bound to a second antibody capable of binding to the antibodies specific for HER-2/neu protein. The step of detecting immunocomplexes involves (a) removing substantially any unbound antibody, (b) adding the second antibody, (c) removing substantially any unbound second antibody and then (d) detecting the presence or absence of the reporter group. Where the antibody specific for HER-2/neu protein is derived from a human, the second antibody is an anti-human antibody.

In a third preferred embodiment for detecting immunocomplexes, a reporter group is bound to a molecule capable of binding to the immunocomplexes. The step of detecting involves (a) adding the molecule, (b) removing substantially any unbound molecule, and then (c) detecting the presence or absence of the reporter group. An example of a molecule capable of binding to the immunocomplexes is protein A.

It will be evident to one skilled in the art that a variety of methods for detecting the immunocomplexes may be employed within the present invention. Reporter groups suitable for use in any of the methods include radioisotopes, fluorophores, enzymes, luminescers, and dye particles.

In a related aspect of the present invention, detection of immunocomplexes formed between HER-2/neu protein and antibodies in body fluid which are specific for HER-2/neu protein may be used to monitor the effectiveness of cancer therapy for a malignancy in which the HER-2/neu oncogene is associated. Samples of body fluid taken from an individual prior to and subsequent to initiation of therapy may be analyzed for the immunocomplexes by the methodologies described above. Briefly, the number of immunocomplexes detected in both samples are compared. A substantial change in the number of immunocomplexes in the second sample (post-therapy initiation) relative to the first sample (pre-therapy) reflects successful therapy.

The following examples are offered by way of illustration and not by way of limitation.

EXAMPLES

Example 1

CD4+ T Cells Responsive to p185(HER-2/neu) Protein and Peptides Can Be Detected in Higher Frequency in Patients with Breast Cancer than Normal Individuals A. p185(HER-2/neu) protein contains multiple segments with amino acid sequences appropriate for binding to class II MHC molecules Soluble proteins are classically processed in the class II MHC pathway. $p185^{HER-2/neu}$ protein is a transmembrane protein present at the cell surface. When overexpressed, it has been found to be soluble and in the extracellular environment both in vitro and in vivo. In vitro studies of human breast cancer cell lines found the extracellular domain of $p185^{HER-2/neu}$ in culture media of rapidly growing cells (Alper et al., *Cell Growth and Differentiation* 1: 591–599, 1990; Zabrecky et al., *J. Biol. Chem.* 266: 1716–1720, 1991). In vivo studies identified circulating portions of the protein in the sera of patients with breast cancer (Leitzel et al., *J. Clin. Oncol.* 10: 1436–1443, 1992; Mori et al., *Jpn. J. Cancer Res.* 81: 489–494, 1990).

Peptide segments of the parental HER-2/neu protein with a motif with theoretical potential to bind to class II MHC molecules were identified herein. Locating potential T cell epitopes was aided by computer analysis. A protein sequence analysis package, T Sites, that incorporates several computer algorithms designed to distinguish potential sites for T cell recognition was used (Feller and de la Cruz, Nature 349: 720–721, 1991). Two searching algorithms were used: (1) the AMPHI algorithm described by Margalit (Feller and de la Cruz, Nature 349: 720–721, 1991; Margalit et al., J. Immunol. 138: 2213–2229, 1987) identified epitope motifs according to alpha-helical periodicity and amphipathicity; (2) the Rothbard and Taylor algorithm identified epitope motifs according to charge and polarity pattern (Rothbard and Taylor, EMBO 7: 93–100, 1988). Segments with both motifs are most appropriate for binding to class II MHC molecules, with the caveat that each particular MHC molecule has a particular binding motif. Using this analysis, more than 40 potential T cell epitopes in the HER-2/neu protein corresponding to the AMPHI and the Rothbard motifs that would have the potential for binding to class II MHC molecules were identified (FIG. 1).

Peptides, each 15 amino acids in length, that encompass both the AMPHI and Rothbard motifs were constructed. The optimal peptide length for class II MHC binding depends upon the particular MHC molecule and may be shorter than 15 amino acids. However, class II MHC responses to exogenous peptides allow for endocytosis and intracellular processing of longer peptides. One of the synthetic peptides (p42–56), HLDMLRHLYQGCQVV (Seq. ID No. 30), is located in the extracellular domain and has 33% homology to epidermal growth factor receptor (EGFR). Two other synthetic peptides, SRLLGICLTSTVQLV (p783–797) (Seq. ID No. 45) and TLERPKTLSPGKNGV (p1166–1180) (Seq. ID No. 54) are both located in the intracellular domain and have 87% and 7% homology to EGFR respectively. The peptides as well as partially purified whole protein (p185$^{HER-2/neu}$) were used in subsequent defined experiments to detect CD4+ T cell proliferation responses (Section C below).

B. p185(HER-2/neu) protein can be obtained and purified from the human breast adenocarcinoma cell line SKBR3

Purified p185 for T cell proliferation studies and antibody detection studies was obtained from the cell line SKBR3. SKBR3 has been reported on extensively in the literature as a commonly used standard cell line with increased HER-2/neu gene copy number and HER-2/neu protein overexpression. In one study, SKBR3 cells were found to contain a mean HER-2/neu oncogene copy number of 43 copies/cell compared with 2.5 copies/cell for MCF-7, a breast cancer cell line considered to be a standard cell line without HER-2/neu gene amplification (Kallionieme et al., Proc. Natl. Acad. Sci. USA 89: 5321–5325, 1992). SKBR3 is reported to be one of the highest known expressors of p185$^{HER-2/neu}$ protein by immunohistochemistry, 4+ compared to 1+ in MCF-7 (Kerns et al., J. Histochem. & Cytochem. 38: 1823–1830, 1990). The same HER-2/neu bands as described in the literature were validated in the present experiments by Western analysis. Bands detected included p185, p105 (extracellular domain), and several smaller bands that presumably represent fragments of phosphorylated protein (Alper et al., Cell Growth and Differentiation 1: 591–599, 1990; Zabrecky et al., J. Biol. Chem. 266: 1716–1720, 1991; Stern et al., Mol. Cell. Biol. 8: 3969–3973, 1988).

The antibodies used for detecting the HER-2/neu protein immunoblotting were commercially prepared by Oncogene Science (Manhasset, N.Y.). The antibody most commonly used in the present experiments was c-neu Ab-3; derived by immunization of BALB/c mice with a peptide sequence, TAENPEYLGLDVPV (Seq. ID No. 65), from the carboxyl domain of human c-neu gene product, and fusion of mouse splenocytes with SP2/0 myeloma cells. A second antibody, c-neu AB-1, gave very faint bands when compared with c-neu Ab-3. This antibody was a polyclonal rabbit affinity purified antibody against the peptide sequence, LARLL-DIDETEYAD (Seq. ID No. 66), from the kinase domain of the human c-neu gene product.

Transmembrane p185$^{HER-2/neu}$ protein was purified from the cell membrane fraction of SKBR3 by modifications of described methods for other membrane-associated proteins (Dhut et al, Leukemia 4: 745–750, 1990; Mietzner et al., J. Exp. Med. 165: 1041–1057, 1987). Three×10$^6$ SKBR3 cells were harvested and suspended in phosphate buffered saline (PBS) with the following protease inhibitors; 1 mM PMSF, 1 mM benzamidine, 5 µg/ml aprotinin. All procedures were done on ice or at 4° C. The cells were then disrupted by sonication at 75 W for a total of 1 minute using a high intensity sonifier equipped with a microtip (Branson Instruments, Inc., Stamford, Conn.). The resulting suspension was then centrifuged for 1 hour at 35,000 rpm to sediment membranes from cytosolic fraction. The membrane pellet was washed in ice cold PBS with protease inhibitors and the cycle of sonication/centrifugation was repeated twice. All cytosolic (supernatant) and membranous fractions were tested for the presence of p185$^{HER-2/neu}$ by Western analysis. The protein was noted to be strongly concentrated in the membrane fraction.

Protein concentration of one of these enriched membrane pellets was determined to be 2625 µg/ml (Protein BioRad assay). p185$^{HER-2/neu}$ is an estimated 8% of membrane protein in SKBR3 (Leitzel et al., J. Clin. Oncol. 10: 1436–1443, 1992); therefore, an estimated 210 µg of p185$^{HER-2/neu}$ were present in the membrane pellet from 3×10$^6$ SKBR3 cells.

If desired, the membrane preparation may be further enriched for p185$^{HER-2/neu}$, e.g., by immunoprecipitation. Briefly, 1 µg of c-neu 3 antibody and 15 µl protein A agarose were added to the sonicated membrane pellet. The mixture was incubated at 4° C. on a rocker for 24 hours. The immunoprecipitate was collected by centrifugation in a micro-centrifuge at 2500 rpm for 15 minutes at 4° C., and the resulting pellet was washed several times with PBS, 1% Trition X-100, 0.5% sodium deoxycholate, and 0.1% sodium dodecyl sulfate. Silver stain and Western analysis showed increased concentration of p$_{185}$$^{HER-2/neu}$ protein and decreases in extraneous membrane proteins when compared to membrane enriched pellets alone.

C. CD4+ T cells reactive to p185(HER-2/neu) protein can be elicited from PBL of normal individuals by using an assay designed for detecting low frequency lymphocyte precursors Three assays were used for the detection of CD4+ responses: a standard proliferation assay, a screening method for low frequency events, and a limiting dilution assay (LDA). Conventional proliferative assays are capable of readily detecting primed responses. The proliferative response stimulation index provides a rough correlation with precursor frequency of antigen-reactive T cells. Any specific proliferative response detected from PBL is considered to be a primed response.

To provide a more quantitative interpretation of CD4+ T cell responses, the assay system developed for detecting low lymphocyte precursor frequency responses (described below) is used. This assay is simple and cost-effective. In circumstances in which more precision is needed, the precursor frequency is validated by limiting dilution assays (Bishop and Orosz, Transplantation 47: 671–677, 1989).

Responses greater than detected in normal individuals are defined as a primed response and imply existent immunity.

Low responses, detectable only by LDA conditions are considered to be unprimed responses. An absent response by LDA or a response lower than that defined by the normal population analysis is considered to be tolerance/anergy.

In general, primed CD4+ T cell responses can be detected in conventional proliferative assays, whereas unprimed responses are not detectable in the same assays. Detection of small numbers of unprimed T cells is limited by confounding background thymidine uptake including the autologous mixed lymphocyte response (AMLR) to self MHC antigen plus responses to processed self serum proteins and exogenously added serum proteins.

To elicit and detect unprimed T cells, an assay system for low frequency responses based on Poisson sampling statistics was used (In: *Pinnacles*, Chiron Corporation, 1: 1–2, 1991). This type of analysis applies specifically to low frequency events in that, if the precursor frequency is less than the number of cells in one replicate culture, many replicates are required to detect a statistically significant number of positives. Theoretically, the analysis will correct for autologous responses by setting up a known positive control (such as PHA or tetanus toxoid) and known negative control (no antigen) and evaluating all data points from lowest to highest irrespective of the experimental group to which they belong. A cutoff value is calculated based on the equation cutoff=M+(F+SD), where M=arithmetic mean, F=3.29, a factor from tables of standardized normal distribution chosen so not more than 0.1% of the "true negatives" of a normally distributed background will be above the cutoff, and SD=standard deviation. In this screening assay, wells above the cutoff are considered true positives that potentially contain a lymphocyte that is specifically proliferating to the antigen of interest. Although estimations of lymphocyte precursor frequency is possible using this method, precise determination requires formal LDA analysis.

Figure 2:
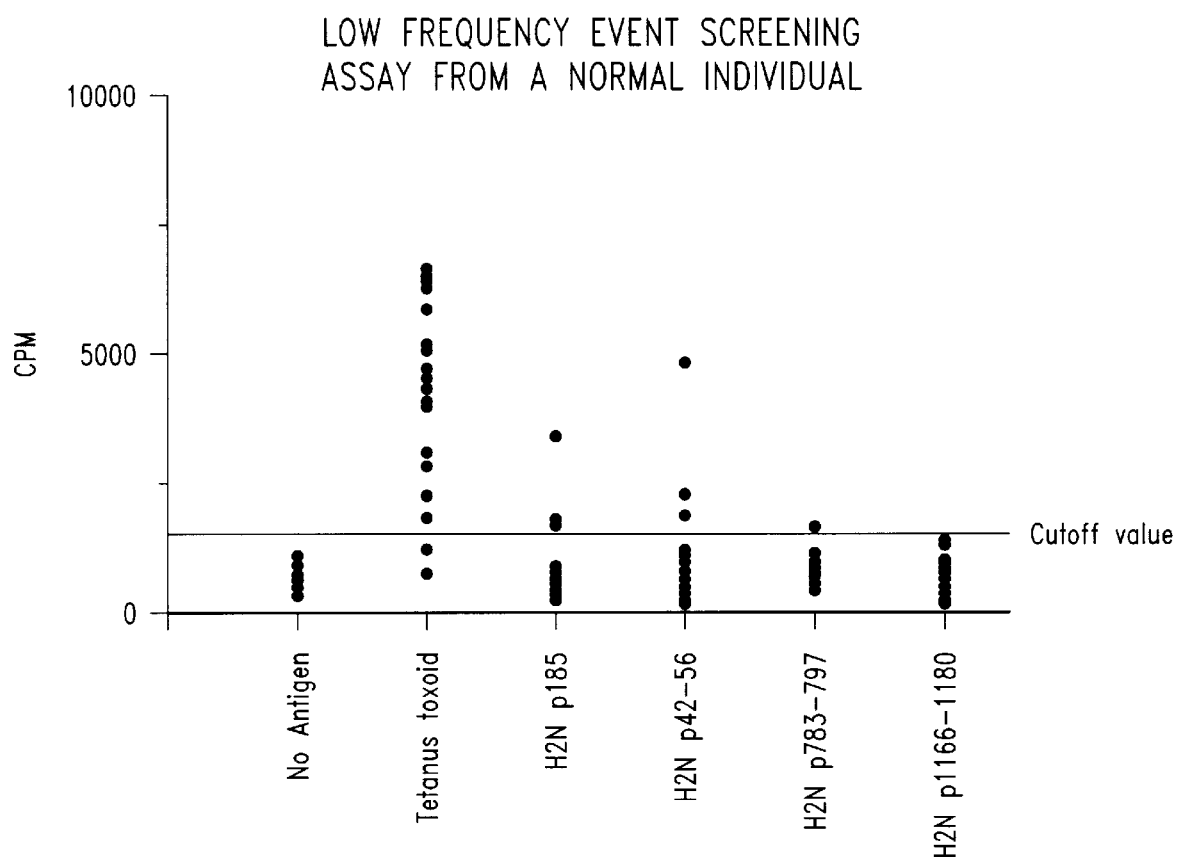
FIG. 2 graphically illustrates the results of a low frequency event screening from a normal individual indicating that a CD4$^+$ T cell response can be detected against p185$^{HER-2/neu}$ and peptides derived from its amino acid sequence. The graph represents the data from one normal individual analyzed with the low frequency screening assayed described further below. Positive responses to the intact protein and two peptides were detected.
Figure 3A:
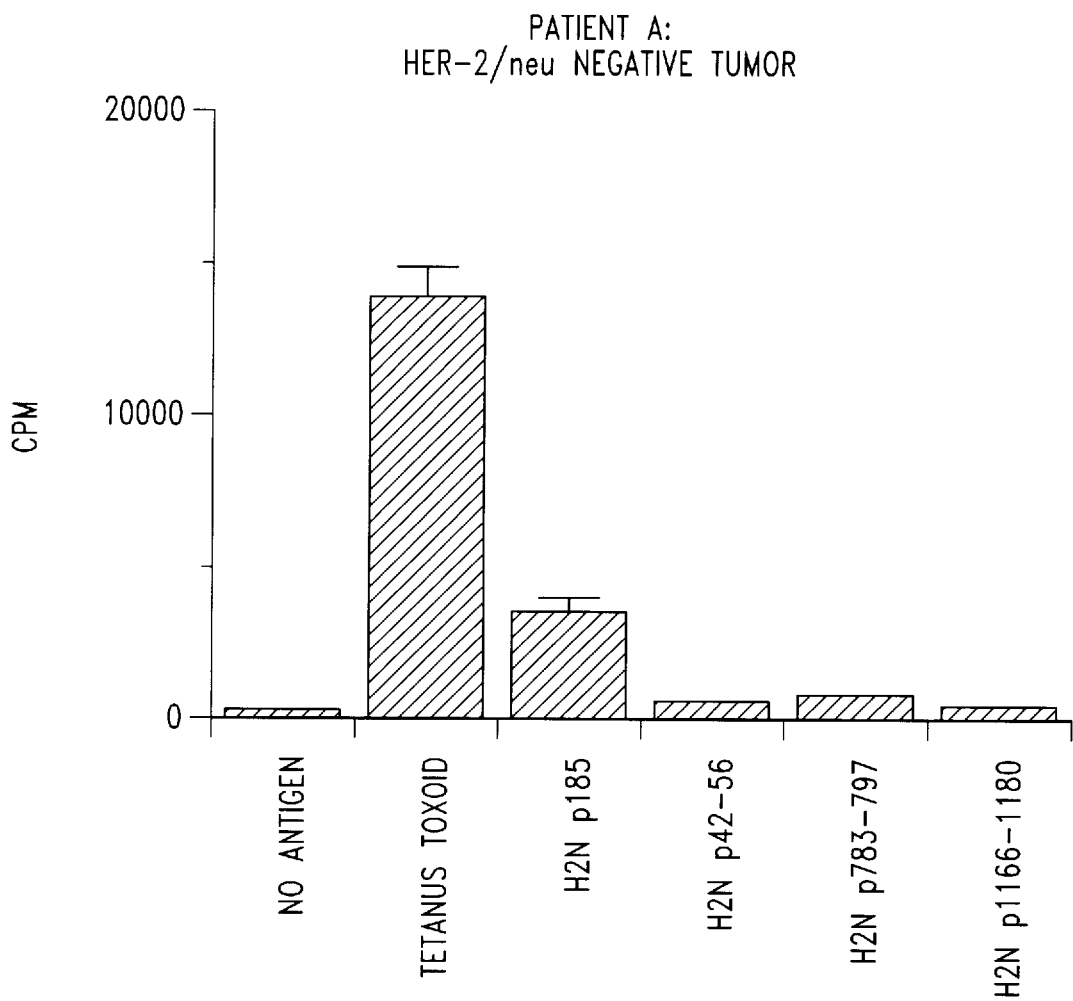
FIGS. 3A–3D graphically illustrate that CD4$^+$ T cells reactive to p185$^{HER-2/neu}$ protein and peptides can be detected in high frequency from patients with HER-2/neu positive breast cancer and can also be detected in some patients with tumors that test negatively for expression of p185$^{HER-2/neu}$ protein. All four breast cancer patients represented here, patient A (FIG. 3A), patient B (FIG. 3B), patient C (FIG. 3C), and patient D (FIG. 3D), were premenopausal women. Patient A had a primary tumor that tested negatively for overexpression of p185$^{HER-2/neu}$. The other three patients had HER-2/neu positive tumors. A proliferation assay was performed using purified peripheral blood mononuclear cells (PBMC) as described below, with each experimental group done in 24 well replicate. Two×10$^5$ PBMC/well were incubated with no antigen, tetanus toxoid (5 µg/ml), p185$^{HER-2/neu}$ (5 µg/ml), or HER-2/neu derived peptides (50 µg/ml) as described further below. After 4 days, wells were pulsed with 1 µCi of tritiated thymidine ($^3$H-TdR) for 6–8 hours and then counted. The data represents the mean of 24 determinations of the c.p.m. with standard error bars expressed.
Figure 3B:
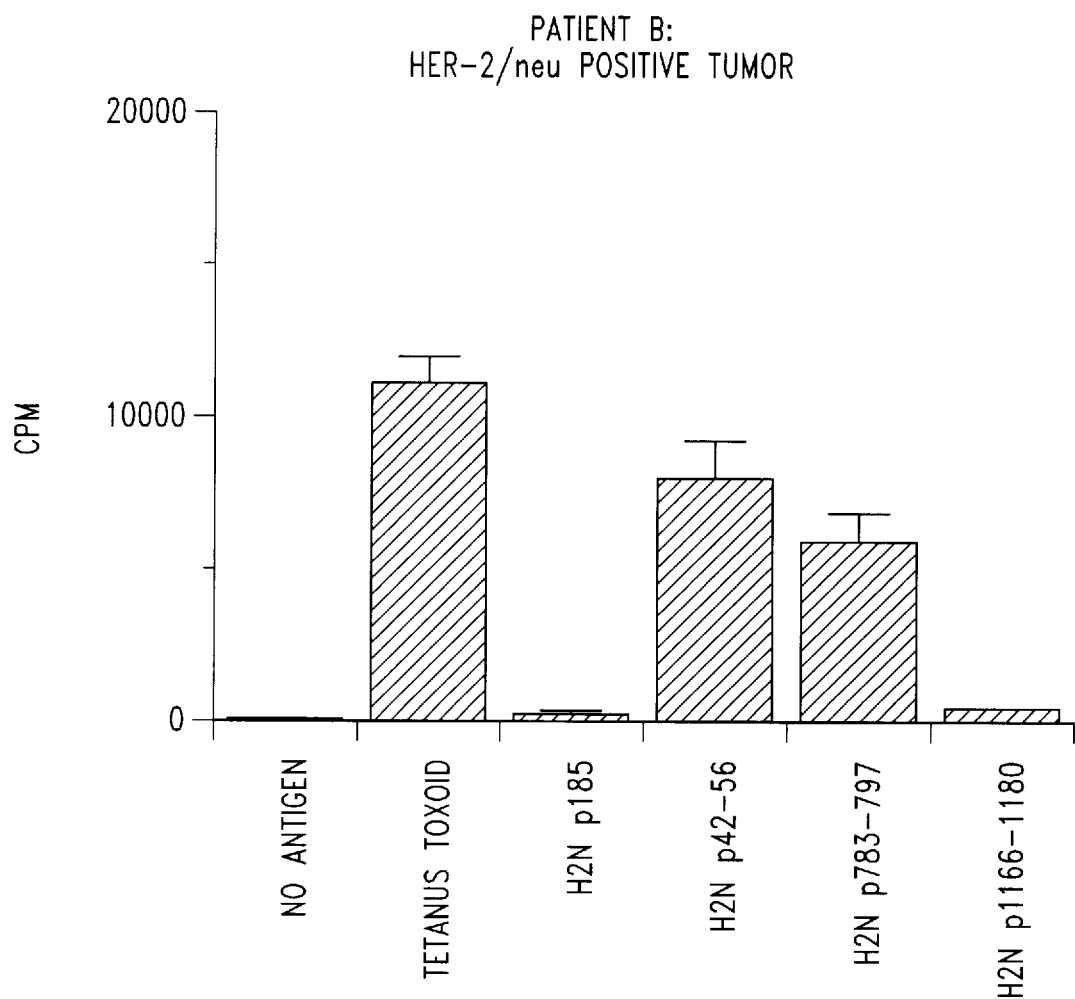
Figure 3C:
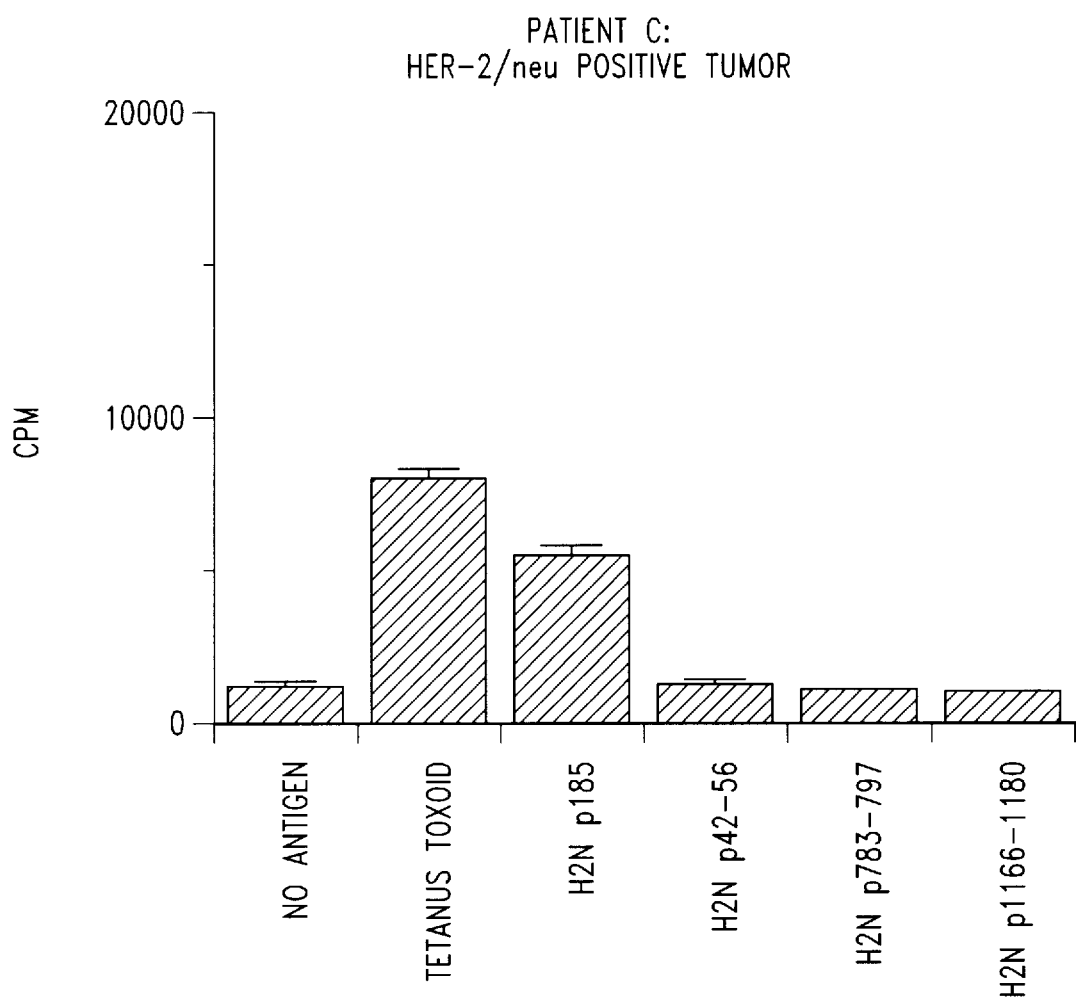
Figure 3D:
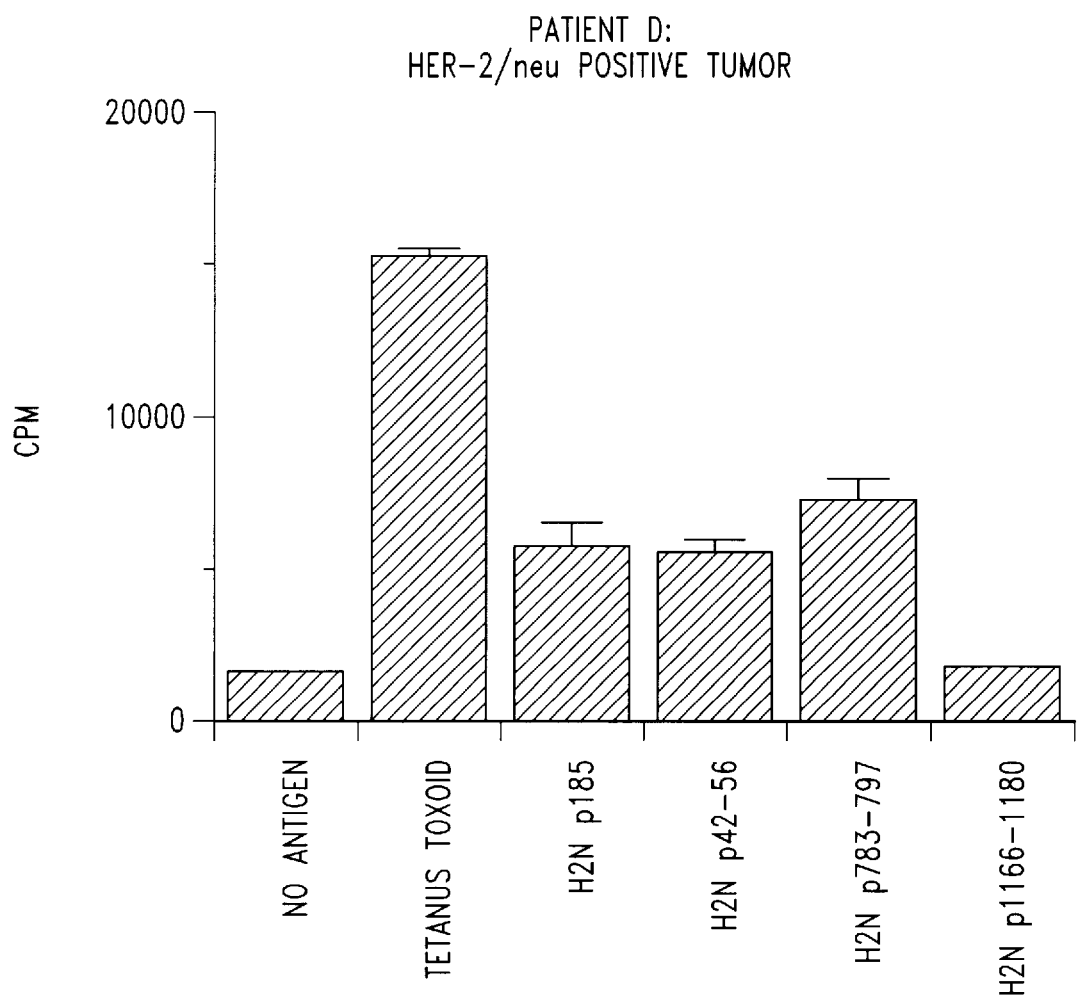

Analysis of PBL from normal individuals for HER-2/neu peptide and protein-specific T cells revealed the presence of a low level frequency of proliferative responses. A representative assay is described in FIG. 2. Seven normal subjects were analyzed, 4 males and 3 females. Of the seven individuals evaluated, 57% had a response to whole protein and 29% had a response to at least one individual peptide. The two individuals that responded to peptide also had responses to parental protein. Three males and one female had detectable responses to the whole protein. Two males responded to one of the four peptides. Similar methods can be used to elicit HER-2/neu reactive T cells from patients with HER-2/neu positive malignancies, but no prior priming in vivo. Alternatively, the methods can be used to assess the efficacy of priming to HER-2/neu in vivo and the procurement of immune T cells to be expanded for therapy.

D. CD4+ T cells reactive to p185(HER-2/neu) and peptide can be detected in the peripheral blood of patients with HER-2/neu positive breast cancer in levels consistent with a primed response Four breast cancer patients with known HER-2/neu tumor status have been evaluated in a standard proliferation assay. Three patients had tumors which overexpressed the HER-2/neu protein. Proliferation to antigen was consistent with a primed response (FIG. 3) (i.e., proliferation was detectable in a standard proliferation assay with a Stimulation Index (S.I.) greater than 2). One patient was HER-2/neu negative and had a response towards intact HER-2/neu, but no response to HER-2/neu-derived peptides. The patients tested and chosen had different stages of disease and were in different stages of treatment. Five normal individuals' responses were analyzed in the same fashion, and none had an S.I. greater than 2 to any HER-2/neu protein or peptide (Table 1).

TABLE 1

(a) Breast Cancer patients

| Patient | HER-2/neu Status | Tetanus Toxoid | p185 | p42–56 | p783–797 | p1166–1180 |
|---|---|---|---|---|---|---|
| A | Negative | 52 | 13 | 2 | 2 | 2 |
| B | Positive | 36 | <2 | 26 | 19 | 2 |
| C | Positive | 7 | 4 | <2 | <2 | <2 |
| D | Positive | 10 | 4 | 4 | 5 | <2 |

(b) Normal Individuals

| Normal | Tetanus Toxoid | p185 | p42–56 | p783–797 | p1166–1180 |
|---|---|---|---|---|---|
| 1 | 6 | 2 | 2 | <2 | <2 |
| 2 | 7 | <2 | 2 | <2 | <2 |
| 3 | 7 | <2 | <2 | <2 | <2 |
| 4 | 10 | 2 | ND | ND | <2 |
| 5 | 11 | 2 | ND | ND | 2 |

Example 2

CD8+ CTL Specific for HER-2/neu Peptides Can Be Generated from PBL of Normal Individuals by Primary In Vitro Immunization to Synthetic Peptides Derived from the Normal Amino Acid Sequence of p185(HER-2/neu) Protein A. p185(HER-2/neu) protein contains multiple segments with an amino acid sequence motif appropriate for binding the class I MHC molecule HLA-A2.1

CD8+ T cells recognize peptide bound to class I MHC molecules. In general, peptide determinants are derived from endogenously synthesized proteins. The rules which determine the ability of a protein to be processed and complexed with class I MHC molecules are not completely understood. Recently, however, it has been determined that peptides binding to particular MHC molecules share discernible sequence motifs (Falk et al., *Nature* 351: 290–296, 1991). A peptide motif for binding in the groove of HLA-A2.1 has been defined by Edman degradation of peptides stripped from HLA-A2.1 molecules of a cultured cell line (Table 2, from Falk et al., supra). The method identified the typical or average HLA-A2.1 binding peptide as being 9 amino acids in length with dominant anchor residues occurring at positions 2 (L) and 9 (V). Commonly occurring strong binding residues have been identified at positions 2 (M), 4 (E,K), 6 (V), and 8 (K). The identified motif represents the average of many binding peptides.

TABLE 2

The HLA-A2.1 Restricted Motif

| | Amino Acid Position | | | | | | | | | Point Assignment |
|---|---|---|---|---|---|---|---|---|---|---|
| | 1 | 2 | 3 | 4 | 5 | 6 | 7 | 8 | 9 | |
| Dominant Binding Anchor Residue | | L | | | | | | | V | +3 |
| Strong Binding Residue | | M | | E K | | V | | K | | +2 |
| Weak Binding | I | | A | G | I | I | A | E | L | +1 |

TABLE 2-continued

The HLA-A2.1 Restricted Motif

| | Amino Acid Position | | | | | | | | | Point Assignment |
|---|---|---|---|---|---|---|---|---|---|---|
| | 1 | 2 | 3 | 4 | 5 | 6 | 7 | 8 | 9 | |
| Residue | L | | Y | P | K | L | Y | S | | |
| | F | | F | D | Y | T | H | | | |
| | K | | | P | T | N | | | | |
| | M | | | M | G | | | | | |
| | Y | | | S | V | | | | | |
| | | | | | H | | | | | |

The derived peptide motif as currently defined is not particularly stringent. Some HLA-A2.1 binding peptides do not contain both dominant anchor residues and the amino acids flanking the dominant anchor residues play major roles in allowing or disallowing binding. Not every peptide with the current described binding motif will bind, and some peptides without the motif will bind. However, the current motif is valid enough to allow identification of some peptides capable of binding.

According to the current motif, the p185$^{HER-2/neu}$ protein contains a substantial number of peptides with amino acid sequences possibly appropriate for binding to the class I MHC antigen HLA-A2.1. Evaluation of the 1255 aa structure of p185$^{HER-2/neu}$ revealed at least 19 peptide segments of 9 aa in length that contained at least one of the dominant anchor residues. Of note, the current HLA-A2.1 motif places 6 amino acids between the dominant anchor amino acids at residues 2 and 9. Recent studies show that alterations in secondary structure of peptides can sometimes allow for additional intervening residues, and thus longer binding peptides. In the present experiment, 9-mer peptides were evaluated. The 10 peptides with both dominant residues were considered. The arbitrary scoring system awarded +3 for a dominant anchor residue, +2 for a strong binding residue, and +1 for a weak binding residue. Emphasis was placed on presence or absence of dominant anchor residues as they appear to be of prime importance for peptide binding to HLA-A2 (Parker et al., J. Immunol. 148: 3580–3587, 1992). Four peptides were synthesized (Table 3). One is located in the extracellular domain of the protein and three are located in the intracellular domain. Homology to EGFR ranges from 11% to 89% (Bargmann et al., Nature 319: 226–230, 1986).

B. Four of four peptides with a motif theoretically appropriate for binding to HLA-A2.1 can be shown to actually bind to HLA-A2.1 in a class I MHC molecule stabilization assay Having identified and synthesized peptides with a theoretical likelihood of binding to HLA-A2.1, the constructed peptides were evaluated as to whether in fact they could bind, the sine quo non of cytotoxic T lymphocytes (CTL) generation. Of the four peptides constructed, all could be shown to bind to HLA-A2 in an assay utilizing the mutant cell line T2. T2 is a human T-B cell hybrid that has a large homozygous deletion within the MHC gene region (Riberdy and Cresswell, J. Immunol. 148: 2586–2590, 1992; Trousdale et al., Nature 348: 741–744, 1990; Spies et al., Nature 348: 744–747, 1990). The use of T2 to determine HLA-A2.1 binding peptides has been well defined. T2 does not appropriately process endogenous antigen for presentation with class I MHC molecules. Consequently, cell surface expression of class I MHC molecules is markedly reduced. However, provision of exogenous peptides which bind to and stabilize class I MHC in the presence of B2 microglobulin results in increased levels of class I at cell surface which can be easily detected by immunofluorescent staining. T2 without exogenous peptide has low expression of HLA-A2 (30%–50%). When incubated with peptides able to bind A2, the level of class I MHC stabilizes on the cell surface and can be measured by immunofluorescent staining. Thus, the T2 line fails to present internal proteins in the class I pathway, but can bind exogenous peptides, providing that the exogenous peptides have the appropriate HLA-A2.1 binding motif.

In this experiment, 1×10$^6$ T2 cells were incubated with individual peptides at a concentration of 25 µg/ml for 18 hours at 37° C. Binding of peptides to HLA-A2 was determined by immunofluorescent staining with a mouse monoclonal HLA-A2 antibody followed by rabbit antimouse IgG-FITC conjugate. The peptides which bound HLA-A2 increased class I surface expression to 60%–85% (10–15 percentage points over baseline).

C. CD8$^+$ CTL specific for HER-2/neu p48–56 and p789–797 can be generated by primary in vitro immunization In general, detection of T cell responses in vitro implies prior priming has occurred in vivo. It has been difficult and rare to generate CTL in vitro from unprimed populations.

Conditions for detecting immunity to standard recall antigens were used and no peptide-specific CTL could be detected. A set of conditions were derived which have allowed priming to 4 of 4 of the binding peptides tested to

TABLE 3 p185$^{HER-2/neu}$ Peptides Constructed for Binding in HLA-A2.1 Motif

| p185$^{HER-2/neu}$ Peptides | Amino Acid Position | | | | | | | | | Score | Location | Homology to EGFR |
|---|---|---|---|---|---|---|---|---|---|---|---|---|
| | 1 | 2 | 3 | 4 | 5 | 6 | 7 | 8 | 9 | | | |
| p48–56$^{HER-2/neu}$ (Seq. ID No. 1) | H | L | Y | Q | G | C | Q | V | V | 8* | Extracellular | 33% |
| p789–797$^{HER-2/neu}$ (Seq. ID No. 7) | C | L | T | S | T | V | Q | L | V | 9* | Intracellular | 89% |
| p851–859$^{HER-2/neu}$ (Seq. ID No. 9) | V | L | V | K | S | P | N | H | V | 9* | Intracellular | 78% |
| p1172–1180$^{HER-2/neu}$ (Seq. ID No. 10) | T | L | S | P | G | K | N | G | V | 9* | Intracellular | 11% |

*Peptide contains both dominant anchor residues date. The conditions were derived by empiric experimentation but are consistent with the current paradigm. Conditions include: (1) large numbers of T cells; (2) a concurrent stimulated primed CD4+ T cell response; (3) IL-2 added late to culture in very small amounts; and (4) multiple restimulations.

Initial experiments examined response to p48–56 which is normally present in the extracellular domain and p789–797 which is normally present in the intracellular domain, both of which were found to bind to HLA-A2.1. Four of four peptides with a motif theoretically appropriate for binding to HLA-A2.1 are shown to actually bind to HLA-A2.1 in a class I MHC molecule stabilization assay (Table 4). T2 cells were incubated for 18 hours with the depicted synthetic p185$^{HER-2/neu}$ peptides. Cells were then washed and stained with antihuman HLA-A2 antibody (3%), a second step FITC-conjugated antibody (3%) was then added. The % increase of class I on cell surface as measured by increased fluorescent intensity of cells incubated with peptide compared to cells incubated in medium alone is indicated.

TABLE 4

| p185$^{HER-2/neu}$ Peptides | % Increase of class I stabilization on T2 |
|---|---|
| p48–56 | 20% |
| p789–797 | 20% |
| p851–859 | 12% |
| p1172–1180 | 10% |

After leukapheresis of a normal homozygous HLA-A2 individual, bulk cultures of lymphocytes (3×10$^7$) were incubated with peptide in a concentration of 10 μg peptide/ml. An individual homozygous for HLA-A2.1 was used on the presumption that a double dose of the MHC/peptide complex would allow more effective priming. Large numbers of lymphocytes were used to overcome the presumed low frequency of precursors. Generation of CD8+ CTL responses has long been known to require concurrent stimulation of CD4+ T cell responses to provide help/amplification. Both peptides used were chosen for class I MHC binding, and presumably could not stimulate CD4+ helper T cells. To provide T cell help, low concentrations (5 μg/ml) of tetanus toxoid were added to culture along with peptide. So as not to overwhelm or dominate the culture with the tetanus toxoid response, titrations of tetanus toxoid had previously been assessed in a standard proliferation assay with the donor's lymphocytes and the concentration of tetanus toxoid that provided the lowest detectable stimulation index was used.

Figure 4A:
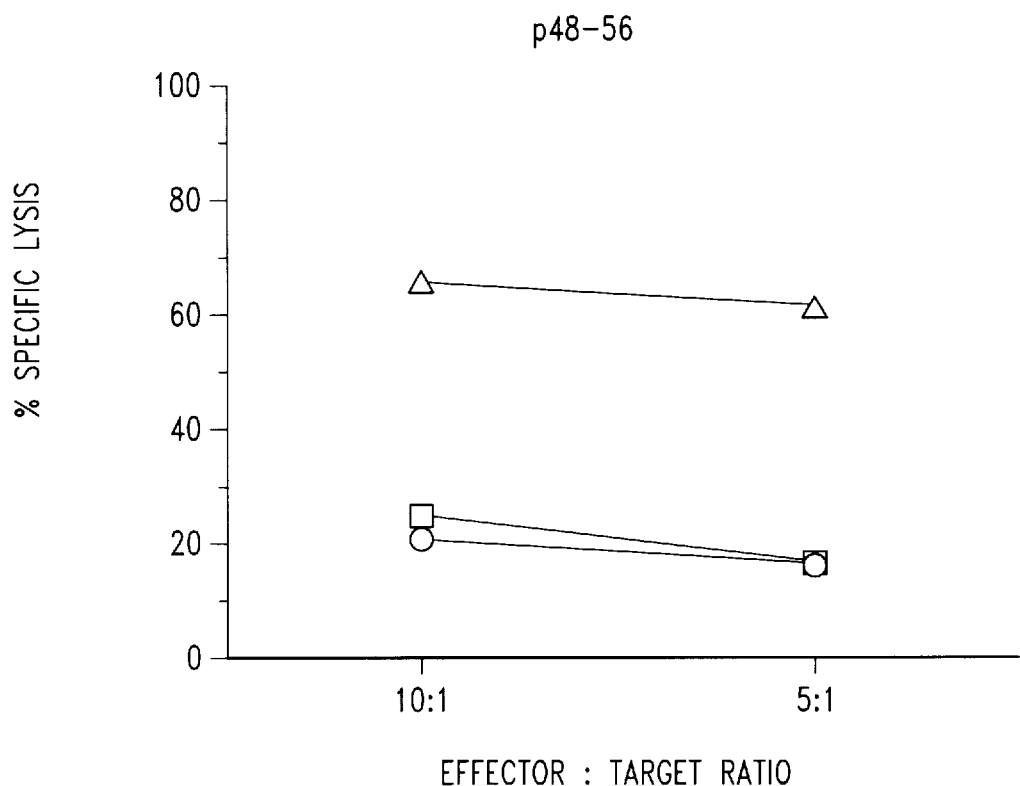
FIGS. 4A–4B graphically illustrate that CD8$^+$ CTL specific for HER-2/neu peptides 48–56 and 789–797 can be generated by in vitro immunization. Three×10$^7$ PBMC from a homozygous HLA-A2 normal donor were incubated with p48–56 or p789–797$^{HER-2/neu}$ peptides at concentrations of 10 µg/ml. The lymphocytes were tested for lytic activity after 10 in vitro sensitizations (IVS). Data is depicted after the tenth IVS with p48–56 (FIG. 4A) or with p789–797 (FIG. 4B). Target cells consisted of $^{51}$Cr-labeled autologous EBV transformed B lymphocytes which had been incubated with p48–56 or p789–797$^{HER-2/neu}$ or an irrelevant peptide for 2 hours prior to use. A four hour chromium release assay (CRA) was performed. The results represent the percent specific lysis at the indicated effector:target (E:T) ratio. Target controls of $^{51}$Cr-labeled K562 and Daudi cells were also included to evaluate NK and LAK activity. The execution of the CRA is as described. The results represent the percent specific lysis at the indicated effector:target (E:T) ratio.
Figure 4B:
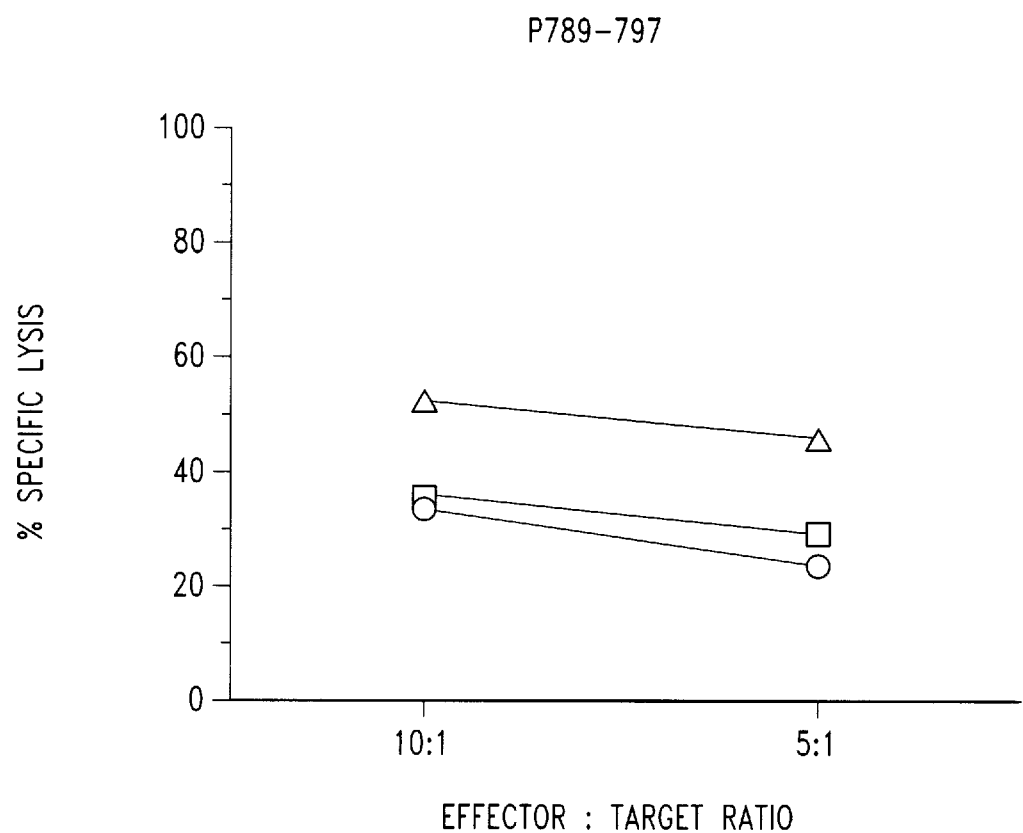

Low doses of IL-2 added late to culture were used to maintain lymphocyte proliferation. Within the present disclosure, standard conditions for expanding in vivo primed CTL following secondary sensitization in vitro usually have included IL-2 at 5–10 U/ml on day 2 of stimulation. Under primary in vitro immunization conditions, similar concentrations of IL-2 induced expansion of non-specifically lytic NK and T cells, presumably due to the predominance of NK cells and AMLR responsive cells relative to peptide-specific CTL. For in vitro priming, the T cell culture received no IL-2 for the first 10 days, with only 1 unit/ml administered on day +2 after the second IVS. Thereafter, IL-2 at 2 U/ml could be administered on day +2 and day +4 of the 7 day stimulation cycle. T cells were stimulated with peptide on irradiated PBL as APC every 7 days. Evaluation for specific lytic function was performed after the fourth IVS and revealed specific lytic activity but substantial non-specific lytic NK and T cell activity. Routine $^{51}$Cr release assay performed after the tenth IVS (FIG. 4) revealed greater than 50% lysis for both bulk T cell lines. Lysis against control targets of K562 and Daudi was less than 2%.

Example 3

Antibodies Directed Against HER-2/neu Protein Can Be Detected in the Sera of Patients with Breast Cancer A. Antibodies directed against p185(HER-2/neu) protein and p105(HER-2/neu) extracellular domain were detected in the sera of some breast cancer patients The sera of 20 patients with breast cancer were analyzed. The 20 patients were participants from the Fred Hutchinson Cancer Research Center, Division of Epidemiology WISH study. The patient population consisted of women recently diagnosed with breast cancer, generally less than 3 months from surgery. Their age was less than 55 and their HER-2/neu tumor status was unknown. Anti-p185 antibody was found in 55% of the group as evidenced by bands corresponding to the positive control.

Figure 5:
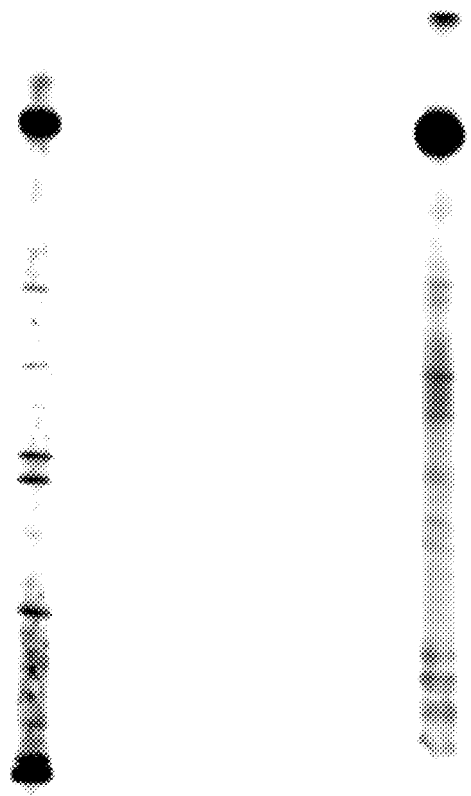
FIG. 5 pictorially illustrates that antibodies are detectable against p185$^{HER-2/neu}$ in the sera of a breast cancer patient. Lane 1 represents the immunoblot of p185 using a HER-2/neu positive breast cancer patient's sera (1:1000 dilution) as primary antibody. The blot was analyzed as described further below. Lane 2 represents the control strip from that experiment developed with c-neu antibody.

Antibody analysis was based on a modification of standard Western blotting techniques (Laemmli, *Nature* 227: 680–685, 1970; Burnett, *Anal. Biochem.* 112: 195–203, 1981). A 7.5% SDS polyacrylamide gel was poured with a single 12 cm long comb in the stacking gel to create a "trough." Two immunoprecipitated SKBR3 membrane preparations, described above, were dissolved in loading buffer and layered across the trough. The gel was then run in standard fashion resulting in a band of equally distributed proteins across the gel. The protein was transferred to nitrocellulose (Amersham Hybond) for subsequent immunoblotting and development by chemiluminescence methods (Amersham ECL). Once protein transfer was complete, the nitrocellulose was cut lengthwise into 25 equal strips and placed in a 25 well incubation tray. The nitrocellulose strips were then blocked with Tris buffered saline and 1% bovine serum albumin (TBS BSA) for 1 hour. This allows for analysis of 23 patients with 2 control strips. Patient sera is used as primary antibody, and after blocking, the strips are incubated for 24 hours at 4° C. with sera diluted 1:200 and 1:400 in TBS BSA. The second antibody is a goat antihuman HRP conjugate which will interact with the chemiluminescent developing reagent (Amersham ECL) resulting in light emission which can be photographed. A control strip is developed with c-neu Ab3 antibody previously described in a similar fashion with this assay both IgA and IgG antibody specific for p185 were detected. Patient sera identified the same p185 band (FIG. 5) as did the known HER-2/neu-specific antibody, providing evidence that some patients have existent antibody immunity to HER-2/neu.

Figure 6:
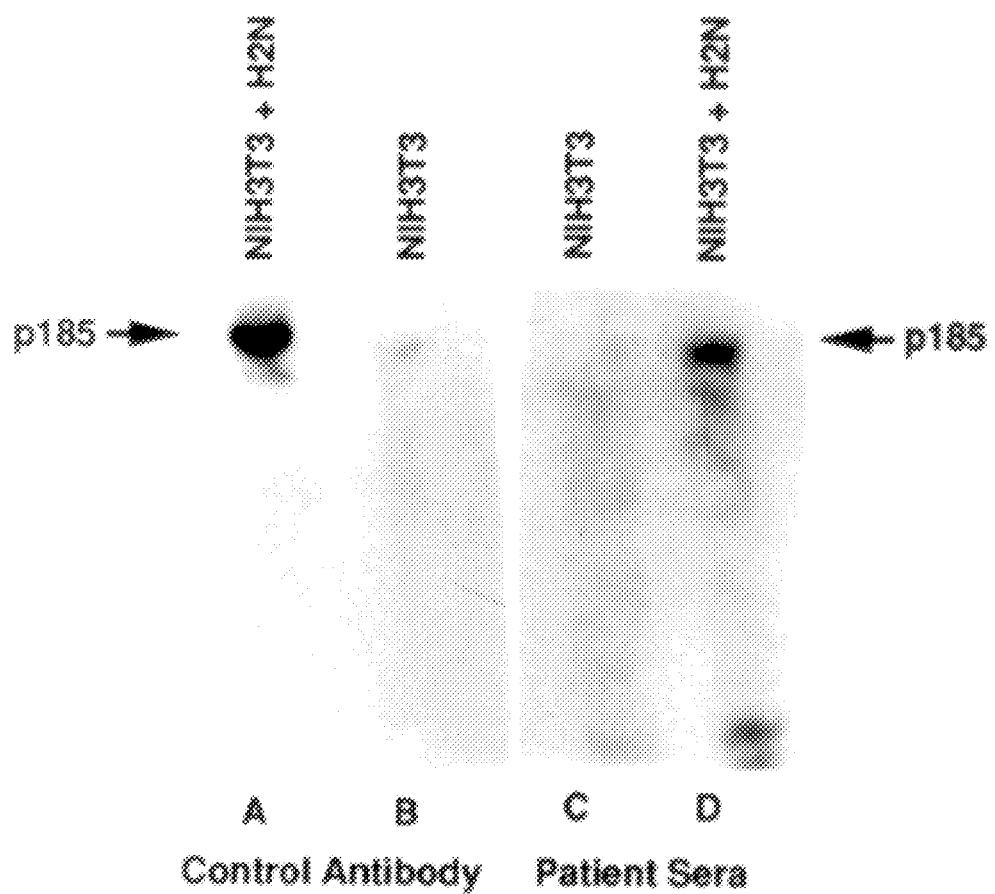
FIG. 6 pictorially shows that antibodies in the sera of a breast cancer patient identify the same p185 band as does a known HER-2/neu-specific antibody ("control antibody"). A membrane preparation from NIH3T3 cells (a murine cell line) that had been transfected with HER-2/neu cDNA ("NIH3T3+H2N") was tested against control antibody (lane A) or patient sera (lane D). Similarly, a membrane preparation from untransfected cells ("NIH3T3") was tested against control antibody (lane B) or patient sera (lane C).

To validate these responses patient sera was tested against a murine cell line (NIH 3T3) that had been transfected with HER-2/neu cDNA. As a negative control, untransfected cells were used. Membrane preparations were prepared from the two cell lines and patient sera was used as primary antibody as previously described. The patient sera identified the same p185 band as did the known HER-2/neu-specific antibody. That band was present in the cells that contained HER-2/neu, but undetectable in the cells that did not contain HER-2/neu (FIG. 6).

Figure 7:
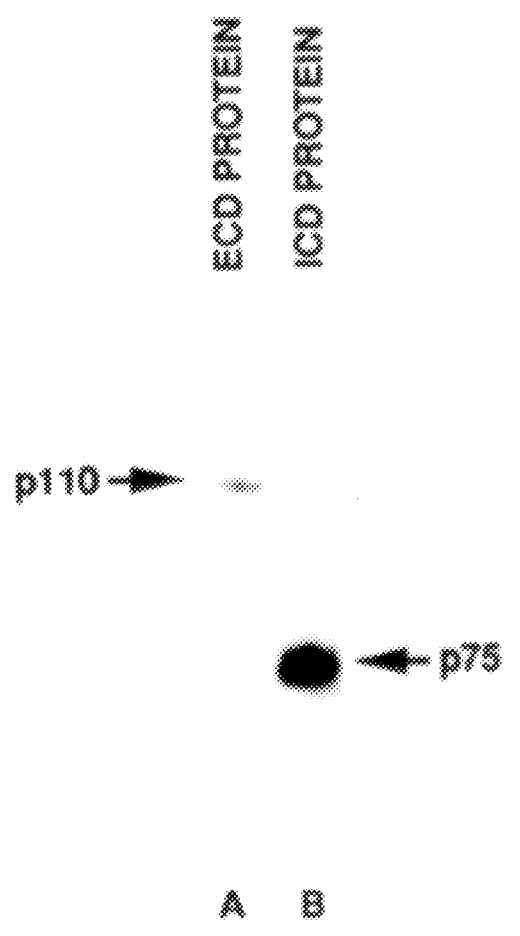

Recombinant proteins of the extracellular and intracellular domain portions of HER-2/neu were obtained. The extracellular protein (110 kD) and intracellular protein (75 kD) were resolved on a 7.5% SDS-PAG gel and incubated with patient sera as primary antibody as previously described. The sera identified both proteins proving that some patients have antibodies directed to both the extracellular and intracellular domain of the HER-2/neu protein (FIG. 7).

B. Seven normal individuals showed no evidence of antibody to HER-2/neu protein

In studies to determine the extent to which detection of antibody to HER-2/neu is specific for malignancy, sera from seven normal individuals was obtained and analyzed in identical fashion as described above. There was no evidence of antibodies directed toward any HER-2/neu protein.

C. The sera of three patients with known HER-2/neu positive tumors contained antibodies against p185 and p105

Sera from breast cancer patients whose HER-2/neu tumor status is known was collected and analyzed to determine the extent to which antibody to HER-2/neu correlates with the presence of HER-2/neu-positive tumors. Three patients with overexpression of $p_{185}$HER-2/neu protein in their primary tumor were analyzed. Antibodies against p185 were detected in all three. The antibody detected in our studies was IgG. Immunoglobulin class switch from IgM to IgG or IgA require T cell help often directed against different epitopes on the same protein molecule.

Example 4

Peptide Based Vaccines Elicit Immunity to HER-2/neu

A. Materials and Methods

1. Animals

Rats used in this study were Fischer strain 344 (CDF (F-344)/CrlBR) (Charles River Laboratories, Portage Mich.). Animals were maintained at the University of Washington Animal facilities under specific pathogen free conditions and routinely used for experimental studies between 3 and 4 months of age.

2. Antigens

Nine peptides were constructed, derived from the amino acid sequence of the rat neu protein. The peptides, 15–18 amino acids in length, were highly homologous to the human HER-2/neu peptide sequence. These peptides were chosen based on an increased probability of interaction with human Class II MHC molecules. This theoretical potential was evaluated by the use of a protein sequence analysis package, TSites, that incorporates several computer algorithms designed to distinguish potential sites for T cell recognition (Feller and de la Cruz, Nature 349: 720–721, 1991). Several peptides identified from the rat sequence were predicted to have potential for class II interaction with both human and murine MHC. Nine peptides were chosen for immunization of the rats (Table 5). Eight of the nine were in areas of 100% homology with human neu. The remaining peptide had greater than 80% homology with human neu (Yamamoto et al., Nature 319: 230–234, 1986). The peptides were synthesized and purified by H. Zabrowski (University of Washington, Seattle, Wash.), then dissolved in phosphate-buffered saline (PBS), pH 7.4, to give 2 mg/ml stock solutions. Prior to aliquoting, peptides were sterile filtered, then stored at −70° C.

TABLE 5

Peptides from the Rat neu Protein for Immunization

| Rat Sequence | Amino Acids | Protein Domain | Homology to Human neu |
| --- | --- | --- | --- |
| p45–59 | HLDMLRHLYQGCQVV (Seq. ID No. 30) | ECD | 100% |
| p98–112 | PLQRLRIVRGTQLFE (Seq. ID No. 31) | ECD | 100% |
| p323–337 | NQEVTAEDGTQRCEK (Seq. ID No. 56) | ECD | 100% |

TABLE 5-continued

Peptides from the Rat neu Protein for Immunization

| Rat Sequence | Amino Acids | Protein Domain | Homology to Human neu |
| --- | --- | --- | --- |
| p332–349 | TQRCEKCSKPCARVCYGL (Seq. ID No. 60) | ECD | 100% |
| p433–447 | RIIRGRILHDGAYSL (Seq. ID No. 67) | ECD | 80% |
| p781–795 | GVGSPYVSRLLGICL (Seq. ID No. 44) | ICD | 100% |
| p788–802 | SRLLGICLTSTVQLV (Seq. ID No. 45) | ICD | 100% |
| p932–946 | PAREIPDLLEKGERL (Seq. ID No. 49) | ICD | 100% |
| p1171–1185 | TLERPKTLSPGKNGV (Seq. ID No. 54) | ICD | 100% |

ECD = extracellular domain
ICD = intracellular domain

3. Immunization

One group of rats was immunized with a mixture of extraceasllular domain (ECD) peptides and one group with a mixture of intracellular domain (ICD) peptides. The final group received adjuvant alone. Peptides were administered at a final concentration of 100 μg each in a total volume of 200 μl. The animals underwent 3 immunizations each 14–16 days apart with either CFA or IFA as adjuvant (Sigma ImmunoChemicals, St. Louis, Mo.). 16 days after the third immunization sera was obtained for assessment of immune response.

4. Cell Lines

Two cell lines were used as a source of neu proteins. SKBR3, a human breast cancer cell line that is a marked overexpressor of HER-2/neu (American Type Culture Collection, Rockville, Md.), was maintained in culture in 10% fetal bovine serum (FBS) (Gemini Bioproducts, Inc., Calabasas, Calif.) and RPMI. DHFR-G8, an NIH/3T3 cell line cotransfected with cneu-p and pSV2-DHFR (American Type Culture Collection, Rockville, Md.), was used as a source of non-transforming rat neu protein (Bernards et al., Proc. Natl. Acad. Sci. USA 84: 6854–6858, 1987). This cell line was maintained in 10% FBS and Dulbecco's modified Eagle's medium with 4.5 g/L glucose. DHFR-G8 cells were passaged through the same medium supplemented with 0.3 μM methotrexate at every third passage to maintain the neu transfectant.

5. Preparation of Cell Lysates

Lysates of both SKBR3 and DHFR-G8 were prepared and used as a source of protein for both ELISA and immuno-precipitation studies. Briefly, a lysis buffer consisting of tris base, sodium chloride and Triton-X (1%) pH 7.5 was prepared. Protease inhibitors were added; aprotinin (1 μg/ml), benzamidine (1 mM) and PMSF (1 mM). 1 ml of the lysis buffer was used to suspend $10^7$ cells. The cells were vortexed for 15 seconds every 10 minutes for an hour until disrupted. All procedures were performed on ice in a 4° C. cold room. After disruption the cells were microfuged at 4° C. for 20 minutes. Supernatant was removed from cell debris and stored in small aliquots at −70° C. until used. Presence of human and rat neu in the lysates was documented by Western blot analysis.

6. ELISA for rat antibody responses 96 well Immulon 4 plates (Baxter SP, Redmond, Wash.: Dynatech Laboratories) were incubated overnight at 4° C. with an IgG2a murine monoclonal antibody directed against rat neu (kindly provided by Dr. M. Green) at a concentration of 10 μg antibody per ml. After incubation, all wells were blocked with PBS and 1% bovine serum albumin (BSA) (Sigma Chemical Co., St. Louis, Mo.), 100 μl/well for 4 hours at room temperature. The plate was washed with PBS/0.5% Tween and protein was added. Rows of wells were coated with alternating PBS/1%BSA and DHFR-G8 lysate ($10^8$ cells/20 ml PBS), 50 μl/well, overnight at 4° C. After washing, the plate was incubated with rat sera at the following dilutions: 1:25, 1:50, 1:100, 1:200. The sera was diluted in PBS/1%BSA/1% FBS/25 μg/ml mouse IgG/0.01% $NaN_3$ and then serially into PBS/1% BSA. 50 μl of diluted sera was added/well and incubated 1 hour at room temperature. Sheep anti-rat Ig horseradish peroxidase (HRP) was added to the wells at a 1:7,500 dilution in PBS/1%BSA and incubated for 45 minutes at room temperature (Amersham Co., Arlington Heights, Ill.). Isotype assays were performed similarly with rabbit anti-rat IgG and sheep anti-rat IgM HRP antibodies as the second step antibody at a concentration of 1:5000 (Serotec Ltd., Oxford, England). Control wells consisting of varying dilutions of c-neu-Ab-1, a rabbit polyclonal antibody directed against the kinase portion of human neu which also has reactivity to rat neu (Oncogene Science, Uniondale, N.Y.), were used as a positive control. These wells received a second step antibody of goat-anti rabbit HRP at a 1:5000 dilution (Amersham Co.). Following the final wash, TMB (Kirkegaard and Perry Laboratories, Gaithersburg, Md.) developing reagent was added. Color reaction was read at an optical density of 640 nm until the positive control wells reached 0.3 OD. The reaction was stopped with 1N HCl and the optical density was read at 450 nm. The OD of each serum dilution was calculated as the OD of the neu coated wells minus the OD of the PBS/1%BSA coated wells. A pool of 5 normal rat sera was run on each plate as a negative control.

7. Immunoprecipitation

Experimental rat sera was used to immunoprecipitate human neu from the SKBR3 cell line and rat neu from the DHFR-G8 cell line. A commercially prepared IgG1 mouse monoclonal antibody, c-neu-Ab-3, which cross reacts with both human and rat neu, was used as the positive control antibody in the immunoprecipitation (Oncogene Science). Sera from 5 pooled normal rats and 2 rats immunized with adjuvant alone and no peptide antigens were used as 2 negative controls. 1 ml of DHFR-G8 or SKBR3 lysate was incubated with 75 μl of rat sera or 10 μl (1 μg) of neu specific monoclonal antibody and 15 μl of protein A+G (Oncogene Science). The solution was rocked gently overnight at 4° C. After this incubation, the agarose was pelleted and washed twice in a tris HCl/EDTA buffer (1M Tris HCl pH 7.5, 0.25M EDTA, and 5M NaCl), then twice in the same buffer with NP-40 added to a 0.5% concentration. The immunoprecipitates were analyzed by Western blot as described above using c-neu-Ab-1 (Oncogene Science) as the primary antibody. This antibody is a neu specific polyclonal rabbit antibody which cross reacts with both human and rat neu.

8. ELISA for peptide epitope analysis 96 well Immulon 4 plates (Dynatech Laboratories) were incubated overnight at 4° C. with peptides at a concentration of 10 μg/well diluted in PBS alternating with rows of PBS/1%BSA. After incubation, all wells were blocked with PBS/1%BSA, 100 μl/well for 4 hours at room temperature. The plate was washed with PBS/0.5% Tween. After washing, the plate was incubated with rat sera at the following dilutions: 1:50 and 1:100. The sera was diluted in PBS/1%BSA/1% FBS/25 μg/ml mouse IgG/0.01% $NaN_3$ and then serially into PBS/1%BSA. 50 μl of diluted sera was added/well and incubated 1 hour at room temperature. Sheep anti-rat HRP was added to the wells at a 1:7,500 dilution in PBS/1%BSA and incubated for 45 minutes at room temperature. Following the final wash, the TMB developing reagent was added. Color reaction was read at an optical density of 640 nm until the reading on the most reactive well reached 0.3 OD. The reaction was stopped with 1N HCl and the optical density was read at 450 nm. The OD of each serum dilution was calculated as the OD of the peptide coated wells minus the OD of the PBS/1%BSA coated wells. A pool of 5 normal rat sera was run with each peptide at the same dilutions as the experimental sera as a negative control.

9. Western Blot analysis for rat antibody responses

Immunoprecipitates of SKBR3 and DHFR-G8 were used as a source of human and rat neu proteins in the Western assays. Recombinant human ECD and ICD (kindly provided by Drs. B. Groner and N. Lydon) were used to evaluate antibody responses to the neu domains. 7.5% polyacrylamide gels were electrophoresed in the Pharmacia Phast System (Pharmacia LKB Biotechnology AB, Uppsala, Sweden). After transfer to nitrocellulose (Hybond-C, Amersham Co.) the neu proteins were identified by immunoblot in a similar manner. All control blots were developed by using the IgG1 mouse monoclonal primary antibody, c-neu-Ab-3 (Oncogene Science). This antibody cross reacts with both rat and human neu. The primary antibody was used in a 1:1000 dilution with tris-buffered saline/1% BSA/0.1% Nonidet P-40. A polyclonal rabbit antimouse HRP-conjugated second antibody (Amersham Co.) was used in a 1:10,000 dilution. The blot was then developed using a chemiluminescent reaction (Amersham ECL). Identically run experimental blots were analyzed with rat sera as primary antibody. The sera were used in a 1:500 dilution with tris-buffered saline/1% BSA/0.1% Nonidet P-40 in an overnight incubation with the blot a 4° C. Secondary antibody, goat-anti rat HRP conjugate (Amersham Co.) was used at a 1:5000 dilution. The blots were developed with ECL detection reagents and exposed to Hyperfilm-ECL (Amersham Co.). The film was developed and examined for reaction to human and rat neu as well as the ICD and ECD domains of the protein. Sera from 5 pooled normal rats and 2 rats immunized with adjuvant alone and no peptide antigens were used as 2 negative controls.

10. T cell proliferation assays

For analysis of neu peptide specific responses: Fresh spleen or lymph node cells were harvested by mechanical disruption and passage through wire mesh and washed. $2 \times 10^5$ spleen cells/well and $1 \times 10^5$ lymph node cells/well were plated into 96-well round bottom microtiter plates (Corning, Corning, N.Y.) with 6 replicates per experimental group. The media used consisted of EHAA 120 (Biofluids) with L-glutamine, penicillin/streptomycin, 2-mercaptoethanol, and 5% FBS. Cells were incubated with 25 μg/ml of the various peptides. The group incubated with the peptide mix received 25 μg of each of the peptides. After 4 days, wells were pulsed with 1 μCi of [$^3$H]thymidine for 6–8 hours and counted. Data is expressed as a stimulation index (SI) which is defined as the mean of the experimental wells divided by the mean of the control wells (no antigen). For analysis of neu protein specific responses: Spleen or lymph node cells were cultured for 3 in vitro stimulations. At the time of analysis $1 \times 10^5$ cultured spleen or lymph node T cells were plated into 96 well microtiter plates as described above. Cells were incubated with 1 μg/ml immunoaffinity column purified rat neu (from DHFR-G8 cells as the source of rat neu). After 4 days, wells were pulsed with 1 μCi of [$^3$H]thymidine for 6–8 hours and counted. Data is expressed as a stimulation index which is defined as the mean of the experimental wells divided by the mean of the control wells (no antigen).

11. Rat T cell culture

Spleen and lymph nodes from immunized rats were harvested into single cell suspensions. PBMC were isolated by Ficoll/Hypaque density gradient centrifugation (Histopaque-1083, Sigma Diagnostics, St. Louis, Mo.). Cells were washed and resuspended in bulk culture of $3 \times 10^7$ cells in 6 well plates. The media used consisted of EHAA 120 (Biofluids) with L-glutamine, penicillin/streptomycin, 2-mercaptoethanol, and 10% FBS. A mix of the immunizing peptides were added directly to culture at a concentration of 10 µg/ml of each peptide. The cultures were restimulated on the peptide mix every 14 days with syngeneic spleen that had been preincubated with the peptide mix for 2 hours, irradiated to 1000 rads, and then washed. Stimulator to effector ratio was 1:1 in each culture. After the second week in culture, media was supplemented with 50% Con A conditioned media. At the end of 3 in vitro stimulations, cells were >98% CD3+.

Figure 8:
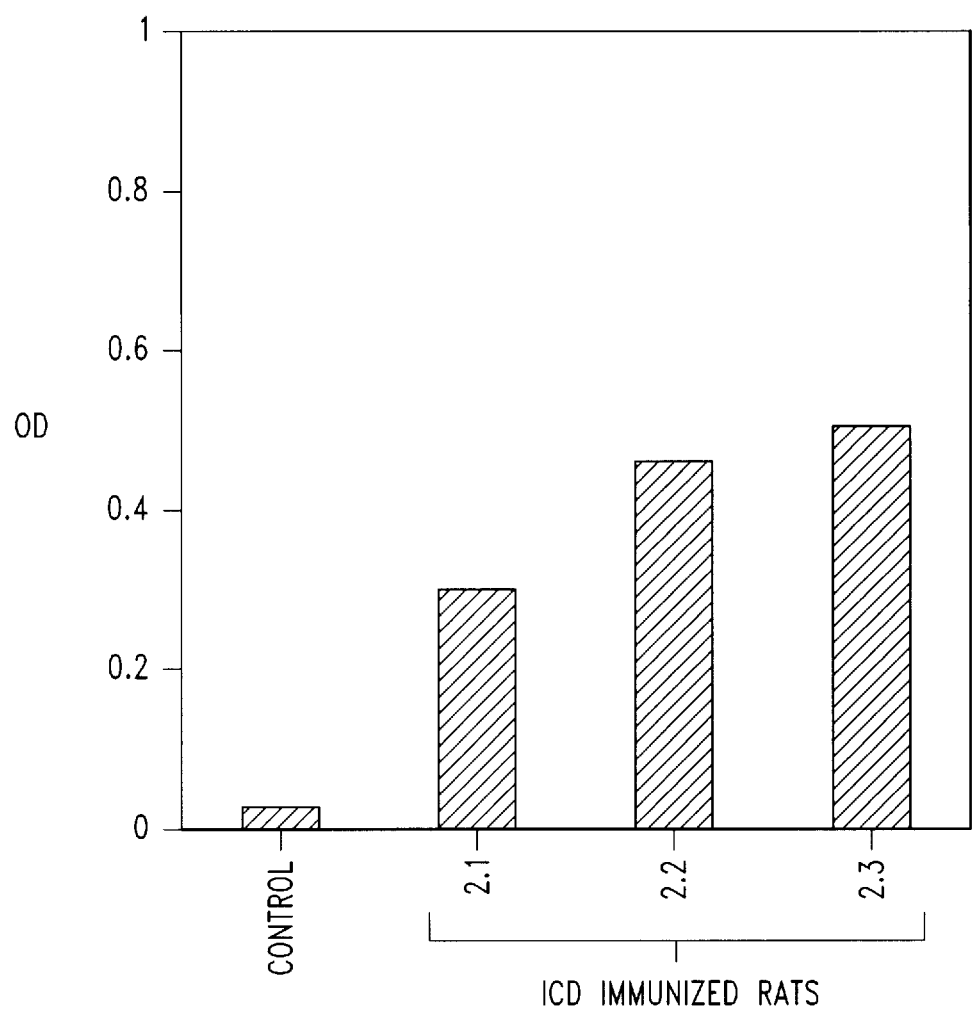
FIG. 8 graphically illustrates that rats immunized with peptides derived from the intracellular domain (ICD) portion of rat neu protein develop antibody responses to neu protein. An ELISA was performed to evaluate peptide immunized animals for antibody responses to non-transforming rat neu protein. Each sera was analyzed at a 1:25, 1:50, 1:100, and 1:200 dilution. The OD value shown is that of the background wells subtracted from the wells coated with neu protein. All data shown is at a rat sera concentration of 1:25. Control sera was derived from an animal immunized with adjuvant alone. Antibody responses titered with decreasing serum concentrations. Results were reproducible in 3 separately run assays.

B. Rats immunized with peptides derived from the ICD portion of rat neu protein develop antibody responses to neu protein Rats were immunized with mixtures of either 4 ICD peptides or 5 ECD peptides. Following the third immunization, serum and T cells from immunized rats were assessed for immunity to neu peptides and protein. Initial experiments assessed rats immunized with ICD peptides for antibody responses to whole neu protein. Serum antibody responses were analyzed by ELISA (FIG. 8). The results demonstrate that immunization to ICD peptides elicited antibody to whole neu protein. Sera was analyzed at 1:25, 1:50, 1:100, and 1:200 dilution. Results at the 1:25 dilution are depicted (FIG. 8). Neu specific antibody responses titered rapidly and at a 1:200 dilution the experimental sera demonstrated the same level of response as control. Isotype analysis revealed that the antibody responses were predominantly IgG (data not shown).

Figure 9:
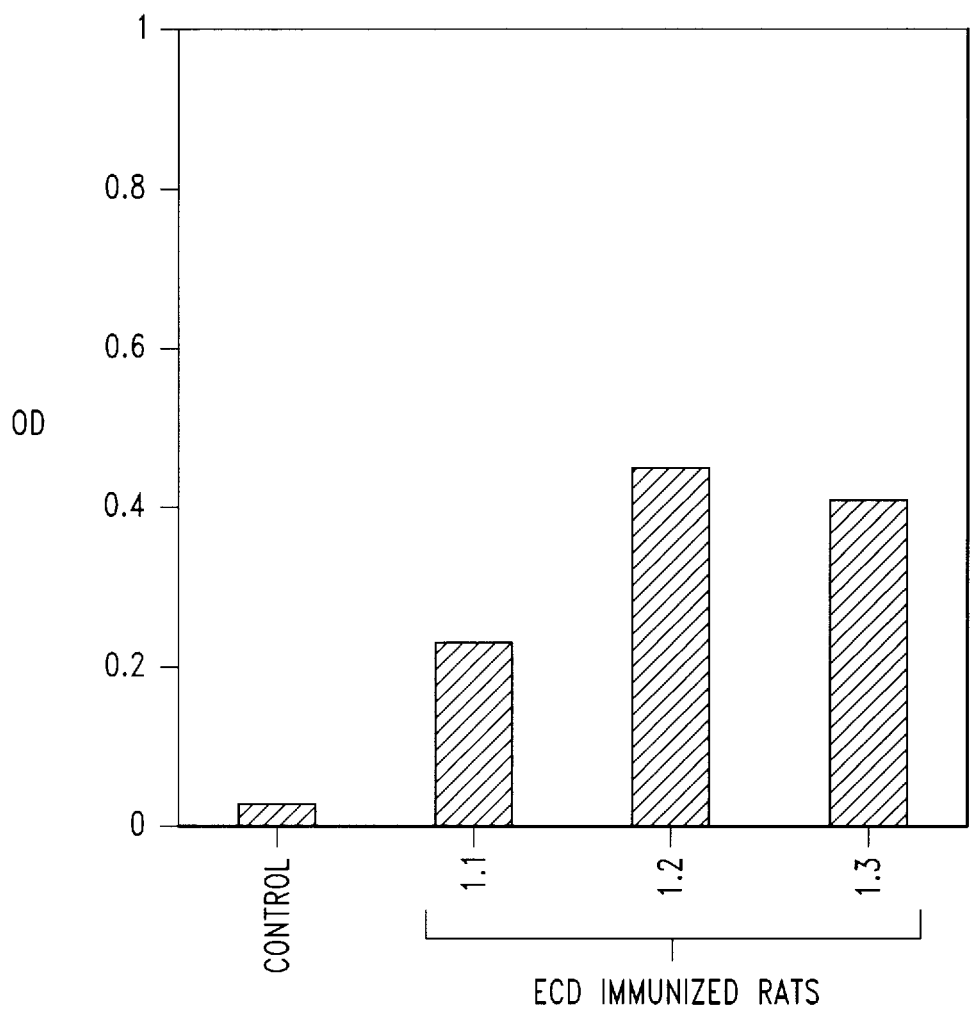
FIG. 9 graphically illustrates that rats immunized with peptides derived from the extracellular domain (ECD) portion of rat neu protein develop antibody responses to neu protein. ELISA evaluation was performed as described in FIG. 8. All data shown is at a rat sera concentration of 1:25.

C. Rats immunized with peptides derived from the ECD portion of rat neu protein develop antibody responses to neu protein Immunizations with ECD peptides were performed in an identical fashion as with ICD peptides. ELISA performed on sera from rats immunized with ECD peptides revealed the generation of antibody responses to whole neu protein (FIG. 9). The responses were equivalent to responses elicited by immunization with ICD peptides. These responses were predominantly of the IgG subtype (data not shown).

D. Epitope analysis of ICD antibody responses demonstrates dominant B cell epitopes as well as "determinant spreading" between domains Mixtures of peptides had been used above for immunization. To determine which peptides in the mixture were the predominant B cell epitopes, sera from rats immunized with ICD peptides was analyzed by ELISA for responses to individual peptides. Responses to both ICD and ECD peptides were evaluated with the presumption that responses to the ECD peptides would be non-existent. Results (FIG. 10) revealed different responses in each rat. All rats had marked antibody responses to the overlapping p781 and p788 ICD peptides, although the relative levels of responses varied between animals. Responses to p932 and p1171 were observed, but were relatively weak. Surprisingly, rats immunized to the mixture of ICD peptides displayed significant antibody responses to ECD peptides. Responses in individual rats varied. Rat 2.2 had substantial responses to all five ECD peptides evaluated. Rats 2.1 and 2.3 had weaker responses. Thus, immunization to ICD peptides elicited antibody responses to ICD peptides as well as "determinant spreading" with the generation of antibody responses to the ECD portion of the molecule. Rats immunized with adjuvant alone did not develop T cell responses to any tested peptide.

E. Epitope analysis of ECD antibody responses demonstrates dominant B cell epitopes Determination of the dominant B cell epitopes in ECD peptide immunized animals was performed in an identical fashion. Again, the relative responses to individual peptides differed between each animal. Rats immunized with ECD peptides developed substantial responses to p45, p332, and p433 and minimal responses to p98 and p323 (FIG. 11). The dominant epitope was p45 in rats 1.1 and 1.3, but was p433 in rat 1.2. As with immunization to ECD peptides, determinant spreading was observed. All rats developed antibody to p788 in the ICD and rats 1.1 and 1.2 responded to p1171. The magnitude and extent of "determinant spreading" appeared to be less in the animals immunized with the ECD peptides than those immunized with the ICD peptides. However, only a limited number of potential epitopes were examined.

F. Antibodies elicited by immunization to either ICD or ECD peptides are specific for and can immunoprecipitate both rat neu protein and human HER-2/neu protein The above experiments showed that immunization to neu peptides could elicit antibody responses to whole rat protein and peptides, as determined by ELISA. Verification of the antibody responses to protein observed by ELISA was performed by assessing the ability of immune sera to immunoprecipitate rat neu protein from lysates of DHFRG-8, an NIH-3T3 cell line transfected with non-transforming rat neu. Results showed that sera from rats immunized with either ECD or ICD peptides could immunoprecipitate rat neu (FIG. 12, Panel A).

The immunizing rat neu peptides were homologous with the human HER-2/neu protein sequence. Thus, the anti-peptide antibodies elicited should be reactive to both rat and human peptides. To determine whether the antibodies elicited were also specific for human HER-2/neu protein, experiments evaluated the ability of sera from peptide immunized rats to immunoprecipitate HER-2/neu from lysates of SKBR3, a human breast cancer cell line that overexpresses HER-2/neu. Sera from all rats immunized with ICD or ECD peptides could immunoprecipitate HER-2/neu protein while the control sera did not (FIG. 12, Panel B).

G. B cell epitopes that are cross reactive between human and rat neu are present in both domains of the protein Antibody elicited by immunization to ICD and ECD peptides immunoprecipitated both rat and human neu protein. To further evaluate the protein domains recognized, sera from rats immunized with ICD and ECD peptides was evaluated by Western analysis for reactivity against human recombinant ECD and ICD as well as whole human and rat neu immunoprecipitated protein. Sera from animals immunized with either ICD or ECD peptides recognized both domains and whole protein from both species (FIG. 13). Control animals had no evidence of antibodies directed against either domain. These results verify not only the phenomenon of "determinant spreading" suggested in the peptide epitope analysis, but also demonstrate human and rat cross reactive epitopes in both domains.

H. Immunization of rats with ICD peptides elicits neu peptide-specific T cell responses The above-detected antibody responses were IgG implying that T cell help was present and operative in immunoglobulin class switch. Spleen and lymph nodes cells were evaluated for proliferative responses to the immunizing peptides. Proliferative T cell responses to the immunizing peptides were observed, but the relative responses between individual rats were varied (FIG. 14). A stimulation index of >2 was arbitrarily chosen as the cut off of significance. Rat 2.1 did not have any proliferative response greater than SI of 2 to the mixture of immunizing ICD peptides or to individual peptides. Rats 2.2 and 2.3 had SI>2 to the mixture of ICD peptides with the dominant response to p1171 in both rats.

I. Immunization of rats with ICD peptides elicits neu protein-specific T cell responses Peptide specific T cell lines were derived by repeated in vitro stimulation of spleen cells from peptide immunized mice by a mixture of the immunizing peptides. After 40 days the cultured cells were greater than 98% CD3+. The cultured T cells from 2 of the 3 immunized rats demonstrated substantial responses to protein with SIs of 9 and 16 (FIG. 15). The SI from the third rat was >2. No responses to control protein were observed.

J. Immunization of rats with ECD peptides elicits only weak peptide-specific T cell responses A similar analysis was performed with T cells derived from animals immunized with the ECD peptides. Unlike the responses observed from the animals immunized with the mixture of ICD peptides, animals immunized with ECD peptides exhibited only weak proliferative responses to the mixture of ECD peptides as well as to individual peptides (FIG. 16). Only one of three rats displayed SI of 2.0 or greater to peptides.

K. Immunization of rats with ECD peptides elicits weak, but positive responses to neu protein Both splenic and lymph node T cells derived from ECD peptide immunized rats were analyzed for responses to rat neu protein (FIG. 17). Splenic T cells exhibited low level responses, whereas responses were greater for lymph node derived T cells. Proliferative responses were not the same for all animals tested. The maximum SI for spleen derived T cell lines was 2.1, whereas the maximum SI for lymph node derived T cells was 3.

From the foregoing, it will be evident that, although specific embodiments of the invention have been described herein for purposes of illustration, various modifications may be made without deviating from the spirit and scope of the invention.

What is claimed is:

1. A method for treating a malignancy in a warm-blooded animal, wherein a HER-2/neu oncogene is associated with the malignancy, comprising the steps of:
   (a) obtaining peripheral blood cells from said warm-blooded animal;
   (b) incubating said cells in the presence of HER-2/neu protein, such that T cells proliferate; and
   (c) administering to said warm-blooded animal said proliferated T cells in an amount effective to prolong the survival time of said warm-blooded animal.

2. The method of claim 1 wherein a HER-2/neu oncogene is associated with a malignancy selected from the group consisting of breast, ovarian, colon, lung and prostate cancer.

3. The method of claim 1 wherein the step of incubating the T cells is repeated one or more times.

4. The method of claim 1 wherein step (a) further comprises separating T cells from the peripheral blood cells, and the cells incubated in step (b) are the T cells.

5. The method of claim 1 wherein step (a) further comprises separating $CD4^+$ cells or $CD8^+$ T cells from the peripheral blood cells, and the cells proliferated in step (b) are $CD4^+$ or $CD8^+$ T cells.

6. The method of any one of claims 1, 4 or 5 wherein step (b) further comprises cloning one or more T cells that proliferated in the presence of HER-2/neu protein, and the T cells administered in step (c) are the cloned T cells.

7. A composition for prolonging the survival time of a warm-blooded animal with a malignancy wherein a HER-2/neu oncogene is associated with the malignancy, comprising T cells proliferated in response to HER-2/neu protein, in combination with a pharmaceutically acceptable carrier or diluent.

* * * * *

SEQUENCE LISTING ( 1 ) GENERAL INFORMATION:

( i i i ) NUMBER OF SEQUENCES: 69

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:1:

```
His  Leu  Tyr  Gln  Gly  Cys  Gln  Val  Val
1                     5
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:2:

```
Pro  Leu  Gln  Pro  Glu  Gln  Leu  Gln  Val
1                     5
```

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:3:

```
Pro  Leu  Thr  Ser  Ile  Ile  Ser  Ala  Val
1                     5
```

( 2 ) INFORMATION FOR SEQ ID NO:4:

( i ) SEQUENCE CHARACTERISTICS:
        ( A ) LENGTH: 9 amino acids
        ( B ) TYPE: amino acid ( D ) TOPOLOGY: linear ( x i ) SEQUENCE DESCRIPTION: SEQ ID NO:4:

Ile Leu Leu Val Val Val Leu Gly Val
1               5

( 2 ) INFORMATION FOR SEQ ID NO:5:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:5:

Leu Leu Val Val Val Leu Gly Val Val
1               5

( 2 ) INFORMATION FOR SEQ ID NO:6:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:6:

Arg Leu Leu Gln Glu Thr Glu Leu Val
1               5

( 2 ) INFORMATION FOR SEQ ID NO:7:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:7:

Cys Leu Thr Ser Thr Val Gln Leu Val
1               5

( 2 ) INFORMATION FOR SEQ ID NO:8:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:8:

Asp Leu Ala Ala Arg Asn Val Leu Val
1               5

( 2 ) INFORMATION FOR SEQ ID NO:9:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:9:

Val Leu Val Lys Ser Pro Asn His Val
1               5

( 2 ) INFORMATION FOR SEQ ID NO:10:

( i ) SEQUENCE CHARACTERISTICS:
    ( A ) LENGTH: 9 amino acids
    ( B ) TYPE: amino acid
    ( D ) TOPOLOGY: linear ( x i ) SEQUENCE DESCRIPTION: SEQ ID NO:10:

Thr Leu Ser Pro Gly Lys Asn Gly Val
1               5

( 2 ) INFORMATION FOR SEQ ID NO:11:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:11:

Val Leu Gly Val Val Phe Gly Ile Leu
1               5

( 2 ) INFORMATION FOR SEQ ID NO:12:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:12:

Leu Ile Lys Arg Arg Gln Gln Lys Ile
1               5

( 2 ) INFORMATION FOR SEQ ID NO:13:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:13:

Lys Ile Pro Val Ala Ile Lys Val Leu
1               5

( 2 ) INFORMATION FOR SEQ ID NO:14:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:14:

Ile Leu Asp Glu Ala Tyr Val Met Ala
1               5

( 2 ) INFORMATION FOR SEQ ID NO:15:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:15:

Gln Leu Met Pro Tyr Gly Cys Leu Leu
1               5

( 2 ) INFORMATION FOR SEQ ID NO:16:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:16:

Gln Ile Ala Lys Gly Met Ser Tyr Leu
1               5

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:17:

Leu Leu Asn Trp Cys Met Gln Ile Ala
1               5

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:18:

Arg Leu Val His Arg Asp Leu Ala Ala
1               5

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:19:

Asp Ile Asp Glu Thr Glu Tyr His Ala
1               5

( 2 ) INFORMATION FOR SEQ ID NO:20:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:20:

Asp Leu Leu Glu Lys Gly Glu Arg Leu
1               5

( 2 ) INFORMATION FOR SEQ ID NO:21:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:21:

Thr Ile Asp Val Tyr Met Leu Met Val
1               5

( 2 ) INFORMATION FOR SEQ ID NO:22:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:22:

Met Ile Met Val Lys Cys Trp Met Ile
1               5

( 2 ) INFORMATION FOR SEQ ID NO:23:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:23:

Asp Leu Val Asp Ala Glu Glu Tyr Leu
    1                5

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:24:

Gly Leu Glu Pro Ser Glu Glu Glu Ala
    1                5

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:25:

Tyr Leu Thr Pro Gln Gly Gly Ala Ala
    1                5

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:26:

Gln Leu Phe Glu Asp Asn Tyr Ala Leu
    1                5

( 2 ) INFORMATION FOR SEQ ID NO:27:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:27:

Lys Ile Phe Gly Ser Leu Ala Phe Leu
    1                5

( 2 ) INFORMATION FOR SEQ ID NO:28:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( x i ) SEQUENCE DESCRIPTION: SEQ ID NO:28:

Ile Leu Asp Glu Ala Tyr Val Met Ala Gly Val ( 2 ) INFORMATION FOR SEQ ID NO:29:

( i ) SEQUENCE CHARACTERISTICS:
      ( A ) LENGTH: 10 amino acids
      ( B ) TYPE: amino acid
      ( C ) STRANDEDNESS:
      ( D ) TOPOLOGY: linear ( x i ) SEQUENCE DESCRIPTION: SEQ ID NO:29:

Val Met Ala Gly Val Gly Ser Pro Tyr Val
   1               5                   10

( 2 ) INFORMATION FOR SEQ ID NO:30:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:30:

His Leu Asp Met Leu Arg His Leu Tyr Gln Gly Cys Gln Val Val
   1               5                   10                  15

( 2 ) INFORMATION FOR SEQ ID NO:31:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:31:

Pro Leu Gln Arg Leu Arg Ile Val Arg Gly Thr Gln Leu Phe Glu
   1               5                   10                  15

( 2 ) INFORMATION FOR SEQ ID NO:32:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:32:

Leu Arg Ser Leu Thr Glu Ile Leu Lys Gly Gly Val Leu Ile Gln
   1               5                   10                  15

( 2 ) INFORMATION FOR SEQ ID NO:33:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:33:

Val Thr Tyr Asn Thr Asp Thr Phe Glu Ser Met Pro Asn Pro Glu
   1               5                   10                  15

( 2 ) INFORMATION FOR SEQ ID NO:34:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:34:

His Leu Arg Glu Val Arg Ala Val Thr Ser Ala Asn Ile Gln Glu
   1               5                   10                  15

( 2 ) INFORMATION FOR SEQ ID NO:35:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:35:

```
Val Arg Ala Val Thr Ser Ala Asn Ile Gln Glu Phe Ala Gly Cys
1               5                   10                  15
```

( 2 ) INFORMATION FOR SEQ ID NO:36:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:36:

```
Asn Ile Gln Glu Phe Ala Gly Cys Lys Lys Ile Phe Gly Ser Leu
1               5                   10                  15
```

( 2 ) INFORMATION FOR SEQ ID NO:37:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:37:

```
Gln Val Phe Glu Thr Leu Glu Glu Ile Thr Gly Tyr Leu Tyr Ile
1               5                   10                  15
```

( 2 ) INFORMATION FOR SEQ ID NO:38:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:38:

```
Gln Glu Cys Val Glu Glu Cys Arg Val Leu Gln Gly Leu Pro Arg
1               5                   10                  15
```

( 2 ) INFORMATION FOR SEQ ID NO:39:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:39:

```
Val Val Val Leu Gly Val Val Phe Gly Ile Leu Ile Lys Arg Arg
1               5                   10                  15
```

( 2 ) INFORMATION FOR SEQ ID NO:40:

( i ) SEQUENCE CHARACTERISTICS:
      ( A ) LENGTH: 15 amino acids
      ( B ) TYPE: amino acid
      ( D ) TOPOLOGY: linear ( x i ) SEQUENCE DESCRIPTION: SEQ ID NO:40:

```
Lys Tyr Thr Met Arg Arg Leu Leu Gln Glu Thr Glu Leu Val Glu
1               5                   10                  15
```

(2) INFORMATION FOR SEQ ID NO:41:

(i) SEQUENCE CHARACTERISTICS:
(A) LENGTH: 15 amino acids
(B) TYPE: amino acid
(D) TOPOLOGY: linear (xi) SEQUENCE DESCRIPTION: SEQ ID NO:41:

| Gly | Ala | Met | Pro | Asn | Gln | Ala | Gln | Met | Arg | Ile | Leu | Lys | Glu | Thr |
|-----|-----|-----|-----|-----|-----|-----|-----|-----|-----|-----|-----|-----|-----|-----|
| 1   |     |     |     | 5   |     |     |     |     | 10  |     |     |     |     | 15  |

(2) INFORMATION FOR SEQ ID NO:42:

(i) SEQUENCE CHARACTERISTICS:
(A) LENGTH: 15 amino acids
(B) TYPE: amino acid
(D) TOPOLOGY: linear (xi) SEQUENCE DESCRIPTION: SEQ ID NO:42:

| Val | Lys | Val | Leu | Gly | Ser | Gly | Ala | Phe | Gly | Thr | Val | Tyr | Lys | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

(2) INFORMATION FOR SEQ ID NO:43:

(i) SEQUENCE CHARACTERISTICS:
(A) LENGTH: 15 amino acids
(B) TYPE: amino acid
(D) TOPOLOGY: linear (xi) SEQUENCE DESCRIPTION: SEQ ID NO:43:

| Ser | Pro | Lys | Ala | Asn | Lys | Glu | Ile | Leu | Asp | Glu | Ala | Tyr | Val | Met |
|-----|-----|-----|-----|-----|-----|-----|-----|-----|-----|-----|-----|-----|-----|-----|
| 1   |     |     |     | 5   |     |     |     |     | 10  |     |     |     |     | 15  |

(2) INFORMATION FOR SEQ ID NO:44:

(i) SEQUENCE CHARACTERISTICS:
(A) LENGTH: 15 amino acids
(B) TYPE: amino acid
(D) TOPOLOGY: linear (xi) SEQUENCE DESCRIPTION: SEQ ID NO:44:

| Gly | Val | Gly | Ser | Pro | Tyr | Val | Ser | Arg | Leu | Leu | Gly | Ile | Cys | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

(2) INFORMATION FOR SEQ ID NO:45:

(i) SEQUENCE CHARACTERISTICS:
(A) LENGTH: 15 amino acids
(B) TYPE: amino acid
(D) TOPOLOGY: linear (xi) SEQUENCE DESCRIPTION: SEQ ID NO:45:

| Ser | Arg | Leu | Leu | Gly | Ile | Cys | Leu | Thr | Ser | Thr | Val | Gln | Leu | Val |
|-----|-----|-----|-----|-----|-----|-----|-----|-----|-----|-----|-----|-----|-----|-----|
| 1   |     |     |     | 5   |     |     |     |     | 10  |     |     |     |     | 15  |

(2) INFORMATION FOR SEQ ID NO:46:

(i) SEQUENCE CHARACTERISTICS:
(A) LENGTH: 15 amino acids
(B) TYPE: amino acid
(D) TOPOLOGY: linear (xi) SEQUENCE DESCRIPTION: SEQ ID NO:46:

| Gly | Ser | Gln | Asp | Leu | Leu | Asn | Trp | Cys | Met | Gln | Ile | Ala | Lys | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

(2) INFORMATION FOR SEQ ID NO:47:

( i ) SEQUENCE CHARACTERISTICS:
 ( A ) LENGTH: 15 amino acids
 ( B ) TYPE: amino acid
 ( D ) TOPOLOGY: linear ( x i ) SEQUENCE DESCRIPTION: SEQ ID NO:47:

| Val | Lys | Ile | Thr | Asp | Phe | Gly | Leu | Ala | Arg | Leu | Leu | Asp | Ile | Asp |
|---|---|---|---|---|---|---|---|---|---|---|---|---|---|---|
| 1 |  |  |  | 5 |  |  |  |  | 10 |  |  |  |  | 15 |

( 2 ) INFORMATION FOR SEQ ID NO:48:

( i ) SEQUENCE CHARACTERISTICS:
  ( A ) LENGTH: 15 amino acids
  ( B ) TYPE: amino acid
  ( D ) TOPOLOGY: linear ( x i ) SEQUENCE DESCRIPTION: SEQ ID NO:48:

| Thr | Val | Trp | Glu | Leu | Met | Thr | Phe | Gly | Ala | Lys | Pro | Tyr | Asp | Gly |
|---|---|---|---|---|---|---|---|---|---|---|---|---|---|---|
| 1 |  |  |  | 5 |  |  |  |  | 10 |  |  |  |  | 15 |

( 2 ) INFORMATION FOR SEQ ID NO:49:

( i ) SEQUENCE CHARACTERISTICS:
  ( A ) LENGTH: 15 amino acids
  ( B ) TYPE: amino acid
  ( D ) TOPOLOGY: linear ( x i ) SEQUENCE DESCRIPTION: SEQ ID NO:49:

| Pro | Ala | Arg | Glu | Ile | Pro | Asp | Leu | Leu | Glu | Lys | Gly | Glu | Arg | Leu |
|---|---|---|---|---|---|---|---|---|---|---|---|---|---|---|
| 1 |  |  |  | 5 |  |  |  |  | 10 |  |  |  |  | 15 |

( 2 ) INFORMATION FOR SEQ ID NO:50:

( i ) SEQUENCE CHARACTERISTICS:
  ( A ) LENGTH: 15 amino acids
  ( B ) TYPE: amino acid
  ( D ) TOPOLOGY: linear ( x i ) SEQUENCE DESCRIPTION: SEQ ID NO:50:

| Arg | Phe | Arg | Glu | Leu | Val | Ser | Glu | Phe | Ser | Arg | Met | Ala | Arg | Asp |
|---|---|---|---|---|---|---|---|---|---|---|---|---|---|---|
| 1 |  |  |  | 5 |  |  |  |  | 10 |  |  |  |  | 15 |

( 2 ) INFORMATION FOR SEQ ID NO:51:

( i ) SEQUENCE CHARACTERISTICS:
  ( A ) LENGTH: 15 amino acids
  ( B ) TYPE: amino acid
  ( D ) TOPOLOGY: linear ( x i ) SEQUENCE DESCRIPTION: SEQ ID NO:51:

| Glu | Asp | Asp | Asp | Met | Gly | Asp | Leu | Val | Asp | Ala | Glu | Glu | Tyr | Leu |
|---|---|---|---|---|---|---|---|---|---|---|---|---|---|---|
| 1 |  |  |  | 5 |  |  |  |  | 10 |  |  |  |  | 15 |

( 2 ) INFORMATION FOR SEQ ID NO:52:

( i ) SEQUENCE CHARACTERISTICS:
  ( A ) LENGTH: 15 amino acids
  ( B ) TYPE: amino acid
  ( D ) TOPOLOGY: linear ( x i ) SEQUENCE DESCRIPTION: SEQ ID NO:52:

| Gly | Met | Gly | Ala | Ala | Lys | Gly | Leu | Gln | Ser | Leu | Pro | Thr | His | Asp |
|---|---|---|---|---|---|---|---|---|---|---|---|---|---|---|
| 1 |  |  |  | 5 |  |  |  |  | 10 |  |  |  |  | 15 |

( 2 ) INFORMATION FOR SEQ ID NO:53:

( i ) SEQUENCE CHARACTERISTICS:
  ( A ) LENGTH: 15 amino acids (B) TYPE: amino acid
(D) TOPOLOGY: linear (xi) SEQUENCE DESCRIPTION: SEQ ID NO:53:

Thr Cys Ser Pro Gln Pro Glu Tyr Val Asn Gln Pro Asp Val Arg
1               5                   10                  15

(2) INFORMATION FOR SEQ ID NO:54:

(i) SEQUENCE CHARACTERISTICS:
    (A) LENGTH: 15 amino acids
    (B) TYPE: amino acid
    (D) TOPOLOGY: linear (xi) SEQUENCE DESCRIPTION: SEQ ID NO:54:

Thr Leu Glu Arg Pro Lys Thr Leu Ser Pro Gly Lys Asn Gly Val
1               5                   10                  15

(2) INFORMATION FOR SEQ ID NO:55:

(i) SEQUENCE CHARACTERISTICS:
    (A) LENGTH: 15 amino acids
    (B) TYPE: amino acid
    (D) TOPOLOGY: linear (xi) SEQUENCE DESCRIPTION: SEQ ID NO:55:

Gly Gly Ala Val Glu Asn Pro Glu Tyr Leu Thr Pro Gln Gly Gly
1               5                   10                  15

(2) INFORMATION FOR SEQ ID NO:56:

(i) SEQUENCE CHARACTERISTICS:
    (A) LENGTH: 15 amino acids
    (B) TYPE: amino acid
    (C) STRANDEDNESS:
    (D) TOPOLOGY: linear (xi) SEQUENCE DESCRIPTION: SEQ ID NO:56:

Asn Gln Glu Val Thr Ala Glu Asp Gly Thr Gln Arg Cys Glu Lys
1               5                   10                  15

(2) INFORMATION FOR SEQ ID NO:57:

(i) SEQUENCE CHARACTERISTICS:
    (A) LENGTH: 15 amino acids
    (B) TYPE: amino acid
    (C) STRANDEDNESS:
    (D) TOPOLOGY: linear (xi) SEQUENCE DESCRIPTION: SEQ ID NO:57:

Gln Val Ile Arg Gly Arg Ile Leu His Asn Gly Ala Tyr Ser Leu
1               5                   10                  15

(2) INFORMATION FOR SEQ ID NO:58:

(i) SEQUENCE CHARACTERISTICS:
    (A) LENGTH: 15 amino acids
    (B) TYPE: amino acid
    (C) STRANDEDNESS:
    (D) TOPOLOGY: linear (xi) SEQUENCE DESCRIPTION: SEQ ID NO:58:

Leu Gln Val Phe Glu Thr Leu Glu Glu Ile Thr Gly Tyr Leu Tyr
1               5                   10                  15

(2) INFORMATION FOR SEQ ID NO:59:

(i) SEQUENCE CHARACTERISTICS:

(A) LENGTH: 15 amino acids
        (B) TYPE: amino acid
        (C) STRANDEDNESS:
        (D) TOPOLOGY: linear (xi) SEQUENCE DESCRIPTION: SEQ ID NO:59:

Ala  Ser  Pro  Leu  Thr  Ser  Ile  Ile  Ser  Ala  Val  Val  Gly  Ile  Leu
1                   5                        10                       15

(2) INFORMATION FOR SEQ ID NO:60:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:60:

Thr  Gln  Arg  Cys  Glu  Lys  Cys  Ser  Lys  Pro  Cys  Ala  Arg  Val  Cys  Tyr
1                   5                        10                       15

Gly  Leu (2) INFORMATION FOR SEQ ID NO:61:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:61:

Arg  Leu  Arg  Ile  Val  Arg  Gly  Thr  Gln  Leu  Phe  Glu  Asp  Asn  Tyr  Ala
1                   5                        10                       15

Leu (2) INFORMATION FOR SEQ ID NO:62:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO:62:

Lys  Ile  Phe  Gly  Ser  Leu  Ala  Phe  Leu  Pro  Glu  Ser  Phe  Asp  Gly  Asp
1                   5                        10                       15

(2) INFORMATION FOR SEQ ID NO:63:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO:63:

Arg  Arg  Leu  Leu  Gln  Glu  Thr  Glu  Leu  Val  Glu  Pro  Leu  Thr  Pro  Ser
1                   5                        10                       15

(2) INFORMATION FOR SEQ ID NO:64:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:64:

```
       Glu  Leu  Val  Ser  Glu  Phe  Ser  Arg  Met  Ala  Arg  Asp  Pro  Gln
       1              5                        10
```

(2) INFORMATION FOR SEQ ID NO:65:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:65:

```
       Thr  Ala  Glu  Asn  Pro  Glu  Tyr  Leu  Gly  Leu  Asp  Val  Pro  Val
       1              5                        10
```

(2) INFORMATION FOR SEQ ID NO:66:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:66:

```
       Leu  Ala  Arg  Leu  Leu  Asp  Ile  Asp  Glu  Thr  Glu  Tyr  Ala  Asp
       1              5                        10
```

(2) INFORMATION FOR SEQ ID NO:67:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:67:

```
       Arg  Ile  Ile  Arg  Gly  Arg  Ile  Leu  His  Asp  Gly  Ala  Tyr  Ser  Leu
       1              5                        10                       15
```

(2) INFORMATION FOR SEQ ID NO:68:

(i) SEQUENCE CHARACTERISTICS:
        (A) LENGTH: 1255 amino acids
        (B) TYPE: amino acid
        (D) TOPOLOGY: linear (xi) SEQUENCE DESCRIPTION: SEQ ID NO:68:

```
       Met  Glu  Leu  Ala  Ala  Leu  Cys  Arg  Trp  Gly  Leu  Leu  Leu  Ala  Leu  Leu
       1              5                        10                       15

Pro  Pro  Gly  Ala  Ala  Ser  Thr  Gln  Val  Cys  Thr  Gly  Thr  Asp  Met  Lys
                      20                       25                       30

Leu  Arg  Leu  Pro  Ala  Ser  Pro  Glu  Thr  His  Leu  Asp  Met  Leu  Arg  His
                 35                            40                       45

Leu  Tyr  Gln  Gly  Cys  Gln  Val  Val  Gln  Gly  Asn  Leu  Glu  Leu  Thr  Tyr
            50                       55                            60

Leu  Pro  Thr  Asn  Ala  Ser  Leu  Ser  Phe  Leu  Gln  Asp  Ile  Gln  Glu  Val
       65                       70                       75                      80

Gln  Gly  Tyr  Val  Leu  Ile  Ala  His  Asn  Gln  Val  Arg  Gln  Val  Pro  Leu
                                85                       90                      95

Gln  Arg  Leu  Arg  Ile  Val  Arg  Gly  Thr  Gln  Leu  Phe  Glu  Asp  Asn  Tyr
                           100                           105                     110

Ala  Leu  Ala  Val  Leu  Asp  Asn  Gly  Asp  Pro  Leu  Asn  Asn  Thr  Thr  Pro
                      115                      120                      125

Val  Thr  Gly  Ala  Ser  Pro  Gly  Gly  Leu  Arg  Glu  Leu  Gln  Leu  Arg  Ser
                 130                           135                      140
```

```
Leu  Thr  Glu  Ile  Leu  Lys  Gly  Gly  Val  Leu  Ile  Gln  Arg  Asn  Pro  Gln
145                 150                           155                      160

Leu  Cys  Tyr  Gln  Asp  Thr  Ile  Leu  Trp  Lys  Asp  Ile  Phe  His  Lys  Asn
                    165                      170                      175

Asn  Gln  Leu  Ala  Leu  Thr  Leu  Ile  Asp  Thr  Asn  Arg  Ser  Arg  Ala  Cys
               180                      185                      190

His  Pro  Cys  Ser  Pro  Met  Cys  Lys  Gly  Ser  Arg  Cys  Trp  Gly  Glu  Ser
          195                      200                      205

Ser  Glu  Asp  Cys  Gln  Ser  Leu  Thr  Arg  Thr  Val  Cys  Ala  Gly  Gly  Cys
     210                      215                      220

Ala  Arg  Cys  Lys  Gly  Pro  Leu  Pro  Thr  Asp  Cys  Cys  His  Glu  Gln  Cys
225                      230                      235                      240

Ala  Ala  Gly  Cys  Thr  Gly  Pro  Lys  His  Ser  Asp  Cys  Leu  Ala  Cys  Leu
                    245                      250                      255

His  Phe  Asn  His  Ser  Gly  Ile  Cys  Glu  Leu  His  Cys  Pro  Ala  Leu  Val
               260                      265                      270

Thr  Tyr  Asn  Thr  Asp  Thr  Phe  Glu  Ser  Met  Pro  Asn  Pro  Glu  Gly  Arg
          275                      280                      285

Tyr  Thr  Phe  Gly  Ala  Ser  Cys  Val  Thr  Ala  Cys  Pro  Tyr  Asn  Tyr  Leu
     290                      295                      300

Ser  Thr  Asp  Val  Gly  Ser  Cys  Thr  Leu  Val  Cys  Pro  Leu  His  Asn  Gln
305                      310                      315                      320

Glu  Val  Thr  Ala  Glu  Asp  Gly  Thr  Gln  Arg  Cys  Glu  Lys  Cys  Ser  Lys
                    325                      330                      335

Pro  Cys  Ala  Arg  Val  Cys  Tyr  Gly  Leu  Gly  Met  Glu  His  Leu  Arg  Glu
               340                      345                      350

Val  Arg  Ala  Val  Thr  Ser  Ala  Asn  Ile  Gln  Glu  Phe  Ala  Gly  Cys  Lys
          355                      360                      365

Lys  Ile  Phe  Gly  Ser  Leu  Ala  Phe  Leu  Pro  Glu  Ser  Phe  Asp  Gly  Asp
     370                      375                      380

Pro  Ala  Ser  Asn  Thr  Ala  Pro  Leu  Gln  Pro  Glu  Gln  Leu  Gln  Val  Phe
385                      390                      395                      400

Glu  Thr  Leu  Glu  Glu  Ile  Thr  Gly  Tyr  Leu  Tyr  Ile  Ser  Ala  Trp  Pro
                    405                      410                      415

Asp  Ser  Leu  Pro  Asp  Leu  Ser  Val  Phe  Gln  Asn  Leu  Gln  Val  Ile  Arg
               420                      425                      430

Gly  Arg  Ile  Leu  His  Asn  Gly  Ala  Tyr  Ser  Leu  Thr  Leu  Gln  Gly  Leu
          435                      440                      445

Gly  Ile  Ser  Trp  Leu  Gly  Leu  Arg  Ser  Leu  Arg  Glu  Leu  Gly  Ser  Gly
     450                      455                      460

Leu  Ala  Leu  Ile  His  His  Asn  Thr  His  Leu  Cys  Phe  Val  His  Thr  Val
465                      470                      475                      480

Pro  Trp  Asp  Gln  Leu  Phe  Arg  Asn  Pro  His  Gln  Ala  Leu  Leu  His  Thr
                    485                      490                      495

Ala  Asn  Arg  Pro  Glu  Asp  Glu  Cys  Val  Gly  Glu  Gly  Leu  Ala  Cys  His
               500                      505                      510

Gln  Leu  Cys  Ala  Arg  Cys  His  Cys  Trp  Gly  Pro  Gly  Pro  Thr  Gln  Cys
          515                      520                      525

Val  Asn  Cys  Ser  Gln  Phe  Leu  Arg  Gly  Gln  Glu  Cys  Val  Glu  Glu  Cys
     530                      535                      540

Arg  Val  Leu  Gln  Gly  Leu  Pro  Arg  Glu  Tyr  Val  Asn  Ala  Arg  His  Cys
545                      550                      555                      560

Leu  Pro  Cys  His  Pro  Glu  Cys  Gln  Pro  Gln  Asn  Gly  Ser  Val  Thr  Cys
```

|     |     |     | 565 |     |     |     | 570 |     |     |     | 575 |     |     |
| --- | --- | --- | --- | --- | --- | --- | --- | --- | --- | --- | --- | --- | --- |

Phe Gly Pro Glu Ala Asp Gln Cys Val Ala Cys Ala His Tyr Lys Asp
            580             585             590

Pro Pro Phe Cys Val Ala Arg Cys Pro Ser Gly Val Lys Pro Asp Leu
        595             600             605

Ser Tyr Met Pro Ile Trp Lys Phe Pro Asp Glu Glu Gly Ala Cys Gln
610             615             620

Pro Cys Pro Ile Asn Cys Thr His Ser Cys Val Asp Leu Asp Asp Lys
625             630             635             640

Gly Cys Pro Ala Glu Gln Arg Ala Ser Pro Leu Thr Ser Ile Ile Ser
            645             650             655

Ala Val Val Gly Ile Leu Leu Val Val Val Leu Gly Val Val Phe Gly
            660             665             670

Ile Leu Ile Lys Arg Arg Gln Gln Lys Ile Arg Lys Tyr Thr Met Arg
            675             680             685

Arg Leu Gln Glu Thr Glu Leu Val Glu Pro Leu Thr Pro Ser Gly
    690             695             700

Ala Met Pro Asn Gln Ala Gln Met Arg Ile Leu Lys Glu Thr Glu Leu
705             710             715             720

Arg Lys Val Lys Val Leu Gly Ser Gly Ala Phe Gly Thr Val Tyr Lys
                725             730             735

Gly Ile Trp Ile Pro Asp Gly Glu Asn Val Lys Ile Pro Val Ala Ile
            740             745             750

Lys Val Leu Arg Glu Asn Thr Ser Pro Lys Ala Asn Lys Glu Ile Leu
        755             760             765

Asp Glu Ala Tyr Val Met Ala Gly Val Gly Ser Pro Tyr Val Ser Arg
770             775             780

Leu Leu Gly Ile Cys Leu Thr Ser Thr Val Gln Leu Val Thr Gln Leu
785             790             795             800

Met Pro Tyr Gly Cys Leu Leu Asp His Val Arg Glu Asn Arg Gly Arg
            805             810             815

Leu Gly Ser Gln Asp Leu Leu Asn Trp Cys Met Gln Ile Ala Lys Gly
            820             825             830

Met Ser Tyr Leu Glu Asp Val Arg Leu Val His Arg Asp Leu Ala Ala
        835             840             845

Arg Asn Val Leu Val Lys Ser Pro Asn His Val Lys Ile Thr Asp Phe
850             855             860

Gly Leu Ala Arg Leu Leu Asp Ile Asp Glu Thr Glu Tyr His Ala Asp
865             870             875             880

Gly Gly Lys Val Pro Ile Lys Trp Met Ala Leu Glu Ser Ile Leu Arg
            885             890             895

Arg Arg Phe Thr His Gln Ser Asp Val Trp Ser Tyr Gly Val Thr Val
            900             905             910

Trp Glu Leu Met Thr Phe Gly Ala Lys Pro Tyr Asp Gly Ile Pro Ala
    915             920             925

Arg Glu Ile Pro Asp Leu Leu Glu Lys Gly Glu Arg Leu Pro Gln Pro
    930             935             940

Pro Ile Cys Thr Ile Asp Val Tyr Met Ile Met Val Lys Cys Trp Met
945             950             955             960

Ile Asp Ser Glu Cys Arg Pro Arg Phe Arg Glu Leu Val Ser Glu Phe
            965             970             975

Ser Arg Met Ala Arg Asp Pro Gln Arg Phe Val Val Ile Gln Asn Glu
            980             985             990

```
Asp Leu Gly Pro Ala Ser Pro Leu Asp Ser Thr Phe Tyr Arg Ser Leu
            995                 1000                1005

Leu Glu Asp Asp Met Gly Asp Leu Val Asp Ala Glu Glu Tyr Leu
    1010                1015                1020

Val Pro Gln Gln Gly Phe Phe Cys Pro Asp Ala Pro Gly Ala Gly
1025                1030                1035                1040

Gly Met Val His His Arg His Arg Ser Ser Thr Arg Ser Gly Gly
                1045                1050                1055

Gly Asp Leu Thr Leu Gly Leu Glu Pro Ser Glu Glu Ala Pro Arg
            1060                1065                1070

Ser Pro Leu Ala Pro Ser Glu Gly Ala Gly Ser Asp Val Phe Asp Gly
            1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
            1155                1160                1165

Arg Pro Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
            1235                1240                1245

Leu Gly Leu Asp Val Pro Val
    1250                1255
```

( 2 ) INFORMATION FOR SEQ ID NO:69:

( i ) SEQUENCE CHARACTERISTICS:
        ( A ) LENGTH: 580 amino acids
        ( B ) TYPE: amino acid
        ( C ) STRANDEDNESS:
        ( D ) TOPOLOGY: linear ( x i ) SEQUENCE DESCRIPTION: SEQ ID NO:69:

```
Lys Arg Arg Gln Gln Lys Ile Arg Lys Tyr Thr Met Arg Arg Leu Leu
1               5                   10                  15

Gln Glu Thr Glu Leu Val Glu Pro Leu Thr Pro Ser Gly Ala Met Pro
            20                  25                  30

Asn Gln Ala Gln Met Arg Ile Leu Lys Glu Thr Glu Leu Arg Lys Val
            35                  40                  45

Lys Val Leu Gly Ser Gly Ala Phe Gly Thr Val Tyr Lys Gly Ile Trp
    50                  55                  60

Ile Pro Asp Gly Glu Asn Val Lys Ile Pro Val Ala Ile Lys Val Leu
65                  70                  75                  80

Arg Glu Asn Thr Ser Pro Lys Ala Asn Lys Glu Ile Leu Asp Glu Ala
                85                  90                  95
```

```
Tyr Val Met Ala Gly Val Gly Ser Pro Tyr Val Ser Arg Leu Leu Gly
            100             105                 110
Ile Cys Leu Thr Ser Thr Val Gln Leu Val Thr Gln Leu Met Pro Tyr
        115             120             125
Gly Cys Leu Leu Asp His Val Arg Glu Asn Arg Gly Arg Leu Gly Ser
    130                 135                 140
Gln Asp Leu Leu Asn Trp Cys Met Gln Ile Ala Lys Gly Met Ser Tyr
145                 150             155                     160
Leu Glu Asp Val Arg Leu Val His Arg Asp Leu Ala Ala Arg Asn Val
                165             170             175
Leu Val Lys Ser Pro Asn His Val Lys Ile Thr Asp Phe Gly Leu Ala
            180             185                 190
Arg Leu Leu Asp Ile Asp Glu Thr Glu Tyr His Ala Asp Gly Gly Lys
        195             200             205
Val Pro Ile Lys Trp Met Ala Leu Glu Ser Ile Leu Arg Arg Arg Phe
    210             215             220
Thr His Gln Ser Asp Val Trp Ser Tyr Gly Val Thr Val Trp Glu Leu
225             230             235                     240
Met Thr Phe Gly Ala Lys Pro Tyr Asp Gly Ile Pro Ala Arg Glu Ile
                245             250             255
Pro Asp Leu Leu Glu Lys Gly Glu Arg Leu Pro Gln Pro Pro Ile Cys
            260             265             270
Thr Ile Asp Val Tyr Met Ile Met Val Lys Cys Trp Met Ile Asp Ser
        275             280             285
Glu Cys Arg Pro Arg Phe Arg Glu Leu Val Ser Glu Phe Ser Arg Met
    290             295             300
Ala Arg Asp Pro Gln Arg Phe Val Val Ile Gln Asn Glu Asp Leu Gly
305             310             315                     320
Pro Ala Ser Pro Leu Asp Ser Thr Phe Tyr Arg Ser Leu Leu Glu Asp
                325             330             335
Asp Asp Met Gly Asp Leu Val Asp Ala Glu Glu Tyr Leu Val Pro Gln
            340             345             350
Gln Gly Phe Phe Cys Pro Asp Pro Ala Pro Gly Ala Gly Gly Met Val
        355             360             365
His His Arg His Arg Ser Ser Thr Arg Ser Gly Gly Gly Asp Leu
370             375             380
Thr Leu Gly Leu Glu Pro Ser Glu Glu Glu Ala Pro Arg Ser Pro Leu
385             390             395                     400
Ala Pro Ser Glu Gly Ala Gly Ser Asp Val Phe Asp Gly Asp Leu Gly
                405             410             415
Met Gly Ala Ala Lys Gly Leu Gln Ser Leu Pro Thr His Asp Pro Ser
            420             425             430
Pro Leu Gln Arg Tyr Ser Glu Asp Pro Thr Val Pro Leu Pro Ser Glu
        435             440             445
Thr Asp Gly Tyr Val Ala Pro Leu Thr Cys Ser Pro Gln Pro Glu Tyr
450             455             460
Val Asn Gln Pro Asp Val Arg Pro Gln Pro Pro Ser Pro Arg Glu Gly
465             470             475                     480
Pro Leu Pro Ala Ala Arg Pro Ala Gly Ala Thr Leu Glu Arg Pro Lys
                485             490             495
Thr Leu Ser Pro Gly Lys Asn Gly Val Val Lys Asp Val Phe Ala Phe
            500             505             510
Gly Gly Ala Val Glu Asn Pro Glu Tyr Leu Thr Pro Gln Gly Gly Ala
        515             520             525
```

-continued

| Ala | Pro 530 | Gln | Pro | His | Pro | Pro 535 | Pro | Ala | Phe | Ser | Pro 540 | Ala | Phe | Asp | Asn |
| Leu 545 | Tyr | Tyr | Trp | Asp | Gln 550 | Asp | Pro | Pro | Glu | Arg 555 | Gly | Ala | Pro | Pro | Ser 560 |
| Thr | Phe | Lys | Gly | Thr 565 | Pro | Thr | Ala | Glu | Asn 570 | Pro | Glu | Tyr | Leu | Gly 575 | Leu |
| Asp | Val | Pro | Val 580 | | | | | | | | | | | | |